United States Patent [19]

Ferčej-Temeljotov et al.

[11] Patent Number: 5,519,012
[45] Date of Patent: May 21, 1996

[54] INCLUSION COMPLEXES OF OPTICALLY ACTIVE 1,4-DIHYDROPYRIDINES WITH METHYL-β-CYCLODEXTRIN

[75] Inventors: Darja Ferčej-Temeljotov; Janko Žmitek; Breda Husu-Kovačevic, all of Ljubljana; Sonja Kotnik, Ljubljana-Črnuče; Zdenka Jerala-Štrukelj, Mavčiče, all of Slovenia

[73] Assignee: LEK, tovarna farmacevtskih in kemicnih izdelkov, d.d., Ljubljana, Ljubljana, Slovenia

[21] Appl. No.: 357,790

[22] Filed: Dec. 16, 1994

Related U.S. Application Data

[63] Continuation of Ser. No. 44,509, Apr. 9, 1993, abandoned.

[30] Foreign Application Priority Data

Apr. 16, 1992 [AT] Austria ..................... 795/92

[51] Int. Cl.⁶ ................... A61K 31/72; A61K 31/44; A61K 47/26
[52] U.S. Cl. ............... 514/58; 514/356; 514/778; 536/103; 546/321
[58] Field of Search .................... 514/356, 778, 514/58; 546/321; 536/103

[56] References Cited

U.S. PATENT DOCUMENTS

| | | | |
|---|---|---|---|
| 4,746,734 | 5/1988 | Tsuchiyama et al. | 536/103 |
| 4,879,303 | 11/1989 | Davison et al. | 514/356 |
| 5,064,944 | 11/1991 | Armstrong | 536/1.1 |
| 5,079,237 | 1/1992 | Husu et al. | 514/58 |

FOREIGN PATENT DOCUMENTS

| | | |
|---|---|---|
| 63-135402 | 6/1988 | Japan . |
| 63-218663 | 9/1988 | Japan . |
| 1319502 | 12/1989 | Japan . |

OTHER PUBLICATIONS

Yoshida et al, Chem. Pharm. Bull. 38(1): pp. 176–179 (1990).
Armstrong et al, Science 232: pp. 1132–1135 (1986).
Acartürk et al, Int. J. Pharm. 85: pp. 1–6 (1992).
Uekama et al, J. Pharm. Pharmacol. 44: pp. 73–78 (1992).
Müller, Int. J. of Pharm. 79: pp. 273–288 (1992).
Yoshida et al, Chem. Pharm. Bull. 37(4): pp. 1059–1063 (1989).
Müller, J. of Pharm. Sci. 80(6): pp. 599–604 (1991).

*Primary Examiner*—John W. Rollins
*Assistant Examiner*—Francisco C. Prats
*Attorney, Agent, or Firm*—Pollock, Vande Sande & Priddy

[57] ABSTRACT

Novel inclusion complexes of racemic 1,4-dihydropyridines and enantiomers thereof of the formula $$\begin{array}{c} R \quad H \\ R_3OOC \diagup \diagdown COOR_4 \\ R_1 \diagdown_N \diagup R_2 \\ H \end{array}$$

wherein

R represents a phenyl group, substituted with nitro, trifluoromethyl, difluoromethoxy group or with one or two halo atoms (especially chlorine), $R_1$ and $R_2$, if the same, represent methyl groups and if one of them has the meaning of a 2-aminoethoxymethyl or cyano group, the other represents a methyl group, $R_3$ and $R_4$, if different, stand each time for a hydrogen, linear or branched $C_1$–$C_6$-alkyl, 2-methoxyethyl, 1-(phenylmethyl)-3-piperidinylphenyl, styryl, furyl, piperidino, 4-diphenylmethyl-1-piperazinylethyl, 5-phenyl-3-pirazolyloxy, 1-phenyl-methyl-3-pyrrolidinyl group or a group of the formula $$-CH_2CH_2N\begin{array}{c}CH_3\\CH_2-\text{Ph}\end{array}$$

or, if the same, stand each time $C_1$–$C_4$ alkyl group, and of acid addition salts thereof with methyl-β-cyclodextrin, hydroxy-ethyl-β-cyclodextrin or hydroxypropyl-β-cyclodextrin, with the exception of inclusion complexes of racemic dihydropyridines with HP-β-CD, or, in case of amlodipine and enantiomeric nicardipine, also with β-cyclodextrin, are disclosed.

Whilst inclusion complexes of racemic dihydropyridines with the cites cyclodextrins are prepared in a well-known manner disclosed in the literature, enantiomerically pure dihydropyridines and inclusion complexes thereof with cyclodextrins are prepared in a novel way by means of preparative column chromatography.

The invention also relates to a pharmaceutical formulation containing novel inclusion complexes and to the use thereof as calcium antagonists for the treatment of hypertension, angina pectoris and cerebrovascular disorders.

10 Claims, 42 Drawing Sheets

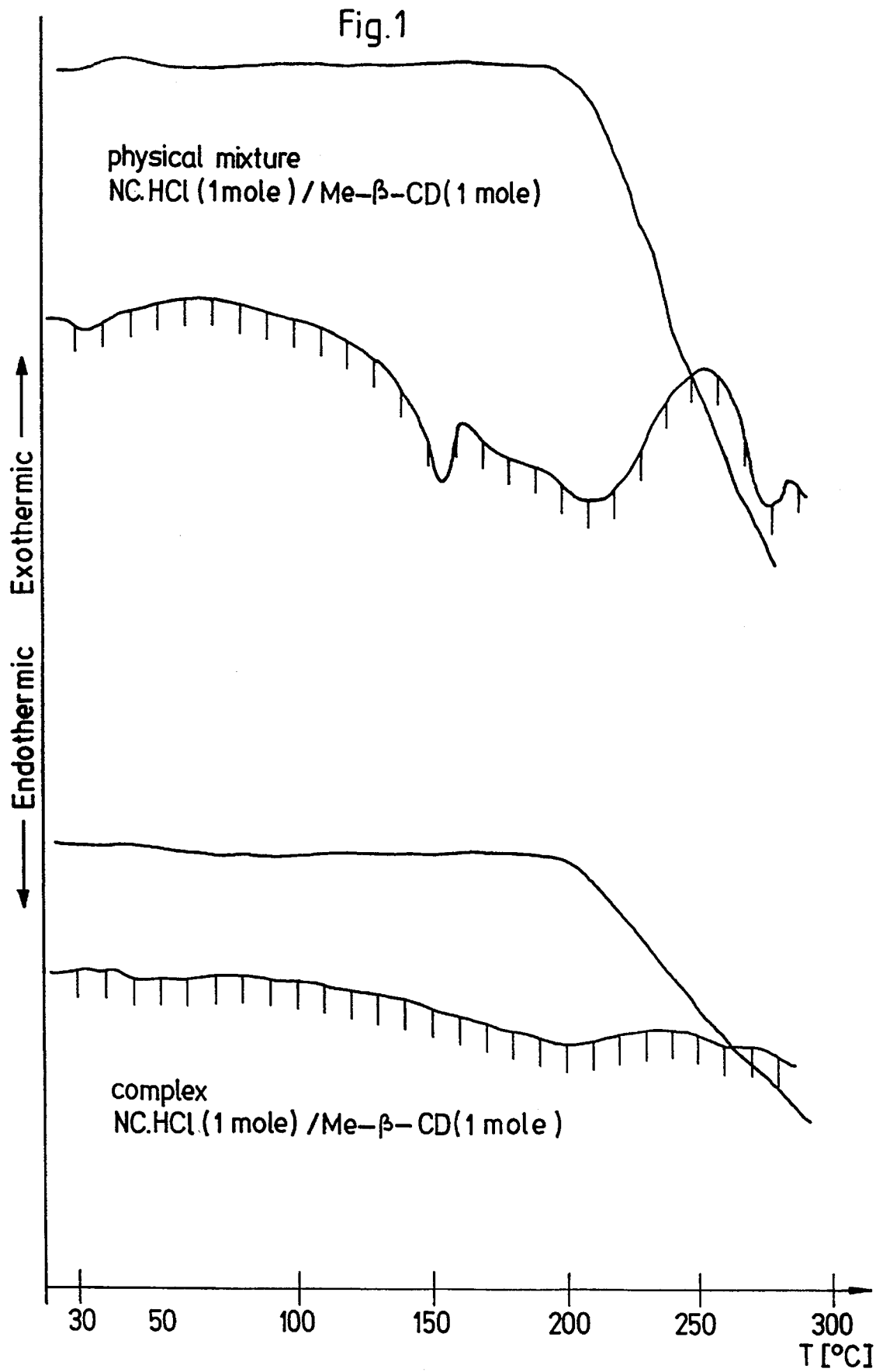

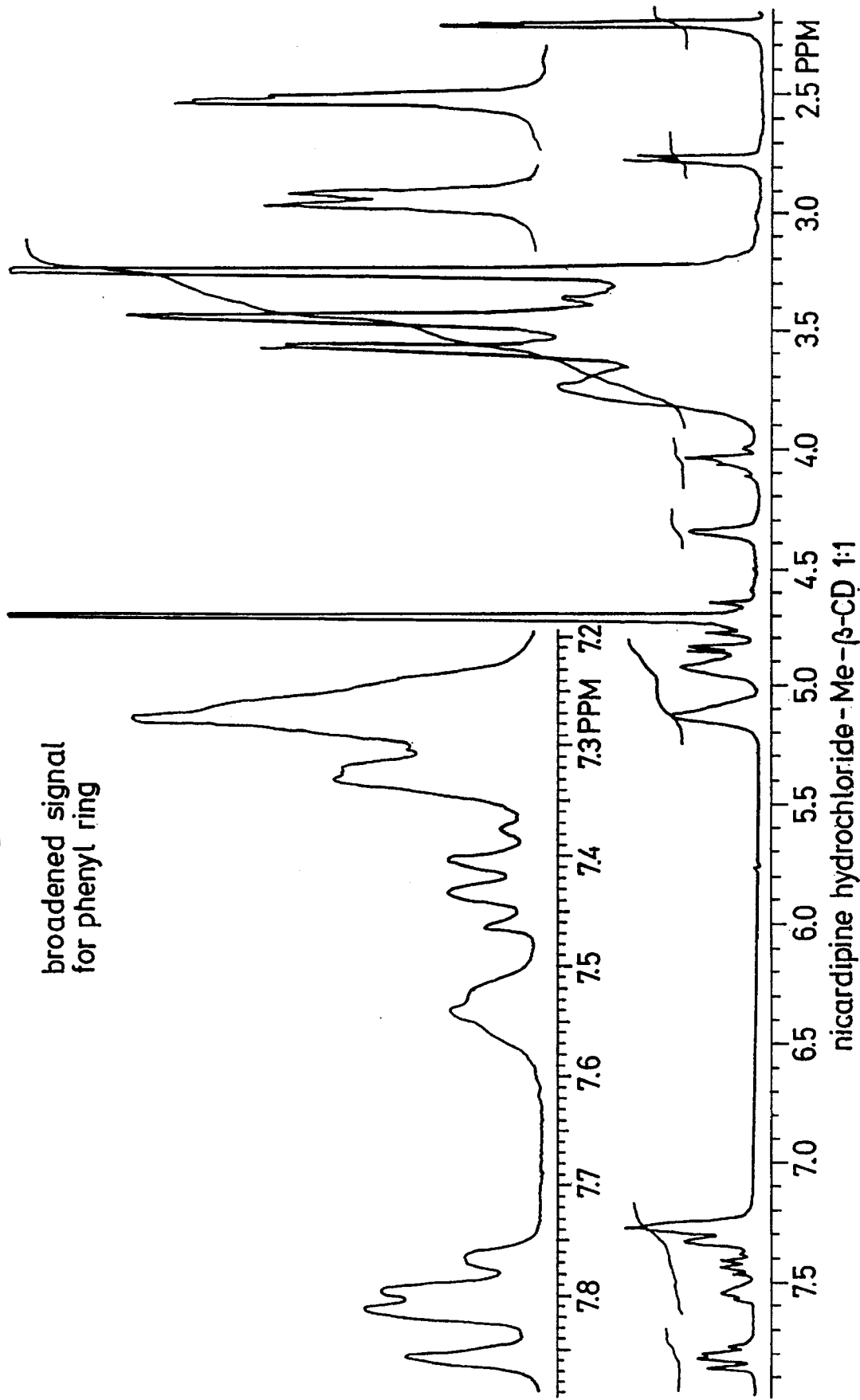

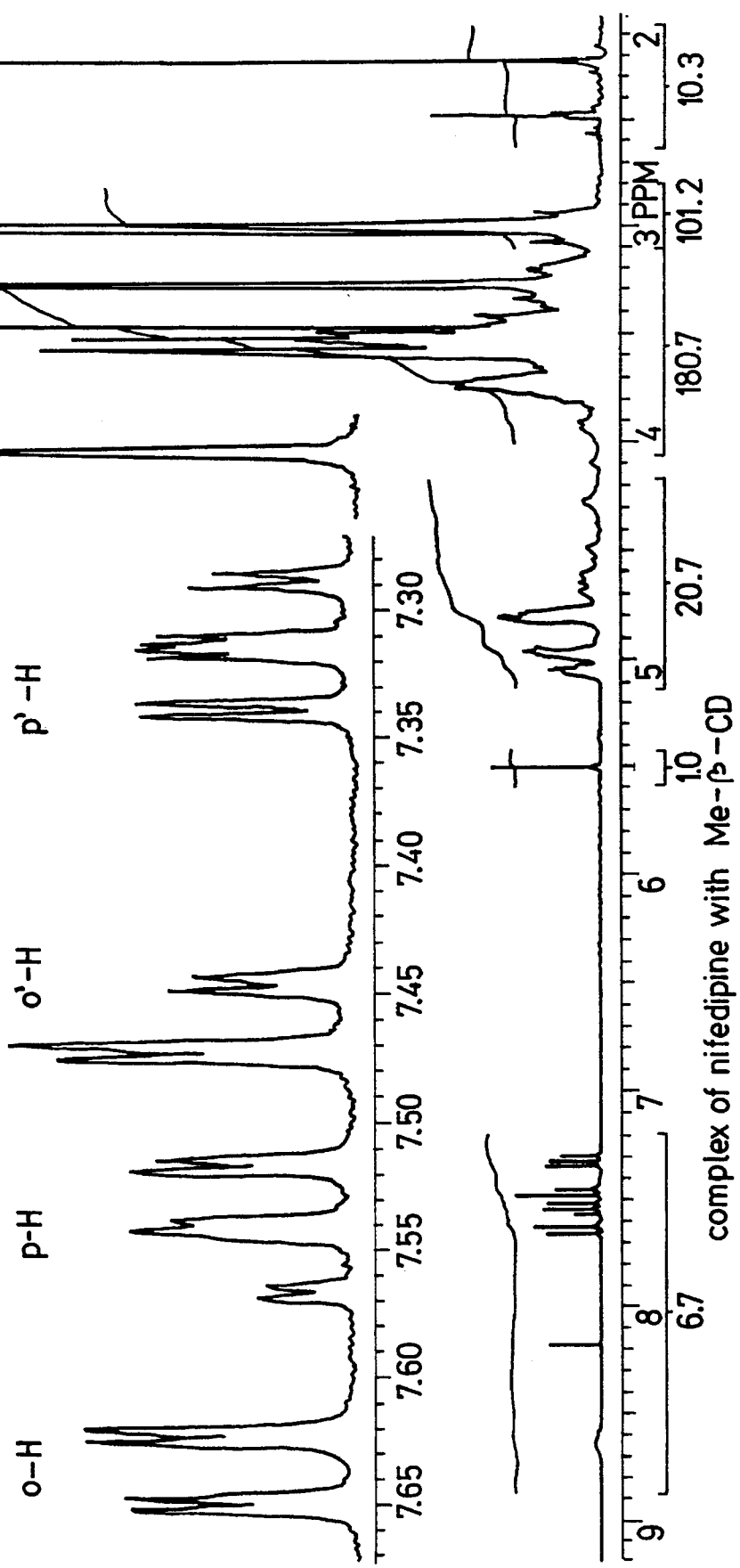
Fig. 5 complex of nifedipine with Me-β-CD

Fig. 8 complex of felodipine with Me-β-CD complex of amlodipine besylate with β—cyclodextrin

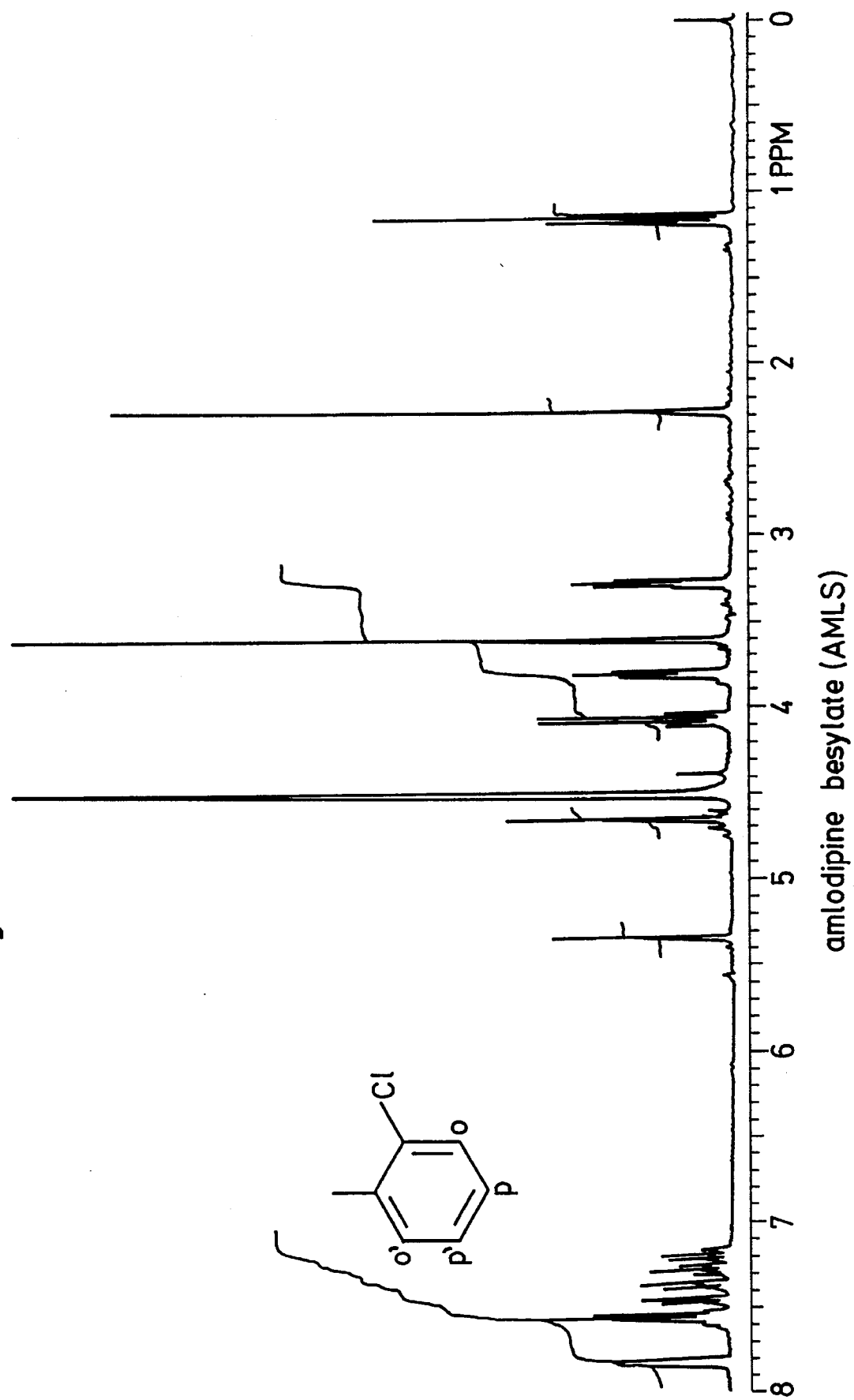
Fig. 12a  amlodipine besylate (AMLS)

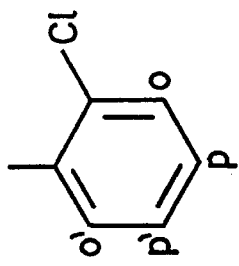
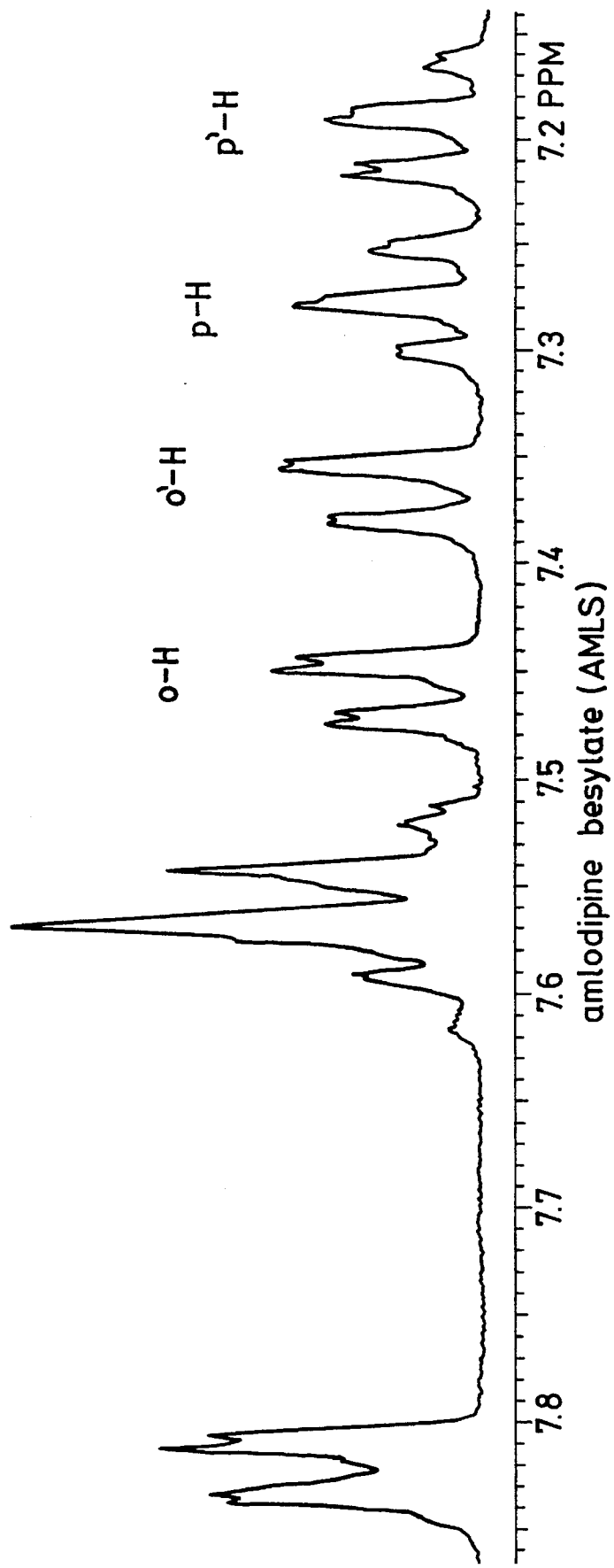
Fig. 12b (−) NC·HCl−HP−β−CD

Fig. 21 (+)-NTP (+)-NTP-Me-β-CD  DSC

Fig. 29 nitrendipine (+)-nitrendipine—Me-β-CD (−)-nitrendipine—Me−ß−CD

Fig. 32 nicardipine hydrochloride

Fig. 33 (−)-nicardipine·HCl−HP−β−CD

Fig. 34  (+)-nicardipine.HCl–HP-β-CD (±)-nicardipine.HCl-HP-β-CD

Fig. 36  (−)-nicardipine.HCl−(HP−β−CD) =1:2

INCLUSION COMPLEXES OF OPTICALLY ACTIVE 1,4-DIHYDROPYRIDINES WITH METHYL-β-CYCLODEXTRIN

This application is a continuation of Ser. No. 08/044,509 filed on Apr. 9, 1993, now abandoned.

The present invention belongs to the field of a pharmaceutical industry and relates to novel inclusion complexes of optically active and racemic 1,4-dihydropyridines with methyl-β-cyclodextrin (abb. Me-β-CD) or other cyclodextrin derivatives such as hydroxylated β-cyclodextrins or, in the case of amlodipine and nicardipine, also with β-cyclodextrin (abb. β-CD), to a process for preparing optically active dihydropyridines and inclusion complexes thereof, to pharmaceutical compositions containing said complexes and to the use of said complexes as calcium antagonists for the treatment of hypertension, angina pectoris and cerebrovascular disorders.

There was a need to convert 1,4-dihydropyridines, which are poorly soluble in water, into a form which is better soluble in water and thus possesses improved pharmaceutical properties such as excellent bioavailability. Thus there would be rendered possible a preparation of improved galenic forms of well-known therapeutically active dihydropyridine derivatives, which are well-known coronary and cerebral vasodilators such as nifedipine, nicardipine hydrochloride, amlodipine besylate, nitrendipine, nimodipine, felodipine etc.

It is well-known that 1,4-dihydropyridine derivatives exhibit interesting pharmacological properties, especially as agents for affecting blood circulation and are disclosed in numerous patents and in the literature such as DE 21 17 571 and DE 24 07 115 and EP 89 167 and EP 7293, resp.

Several 1,4-dihydropyridine derivatives, well-known under common names such as nifedipine, nicardipine hydrochloride, amlodipine, nitrendipine, nimodipine, felodipine etc., are contained in commercial preparations and act as coronary and cerebral vasodilators. As to the action thereof, they are calcium antagonists and are used in the therapy of hypertension and angina pectoris.

Said active substances are used in commercial preparations in the form of racemic compounds, though it is well-known for some of them that one of the enantiomers has a substantially higher activity. Thus R-(-) isomer of amlodipine has a substantially higher activity than S-(+) form (Arrowsmith et al, J. Med. Chem. 1986, 29, 1696).

In T. Shibanuma et al, Chem. Pharm. Bull., 28(9), 2809–2812 (1980) there is disclosed a synthesis of optically active nicardipine, the (+) isomer having a three times higher activity than the (-) isomer.

Also the optically pure (-) isomer of nimodipine has higher activity than the (+) isomer as disclosed in R. Towart et al, Arzneim. Forsch./Drug Res. 32 (I.), Nr.4 (1982), 338–339.

Several optically active 1,4-dihydropyridines (abb. DHP), several processes for the preparation thereof as well as the use thereof as medicines, especially as agents for affecting blood circulation, are well-known from EP-A-0026317.

Inclusion complexes of dihydropyridines with hydroxypropyl-β-cyclodextrin (abb. HP-β-CD) are well-known from JP Kokai 88-218663. In this way there is improved the water solubility of dihydropyridines that are poorly soluble in water, which affects the bioavailability of the active substance.

The use of an inclusion complex of nimodipine with 2-hydroxypropyl-β-cyclodextrin in an intramuscular injectable formulation is disclosed in A. Yoshida, Chem. Pharm. Bull. 38 (1), 176–179 (1990).

An inclusion complex of nicardipine or of hydrochloride thereof with β-cyclodextrin (abb. β-CD) is well-known from EP-A-0324982. Therewith the solubility of the active substance in the intestinal juice is improved. The enhanced scope and rate of dissolution make possible the preparation of a pharmaceutical formulation with sustained release, having an improved bioavailability.

The complexing of novel aromatically substituted dihydropyridine esters with native cyclodextrins and 2-hydroxypropyl-β-cyclodextrin in a solution is disclosed in B. W. Müller and E. Albers, Int. J. of Pharm. 79 (1992), 273–288.

BRIEF DESCRIPTION OF THE DRAWINGS

FIG. 1 depicts a Dynamic scanning calometry (DSC) thermogram of a physical nicardipine hydrochloride (NC.HCl) (1 mole)/methyl-β-cyclodextrin (Me-β-CD) (1 mole) mixture (top) and a NC.HCl (1 mole)/Me-β-CD (1 mole) complex (bottom).

FIG. 2 shows the $^1$H-NMR specter of an inclusion complex of NC.HCl with Me-β-CD (1:1).

FIG. 5 shows the $^1$H-NMR specter of an inclusion complex of nifedipine with Me-β-CD.

FIG. 12a and 12b show the NMR specter of AML.S.

Figure 3A:
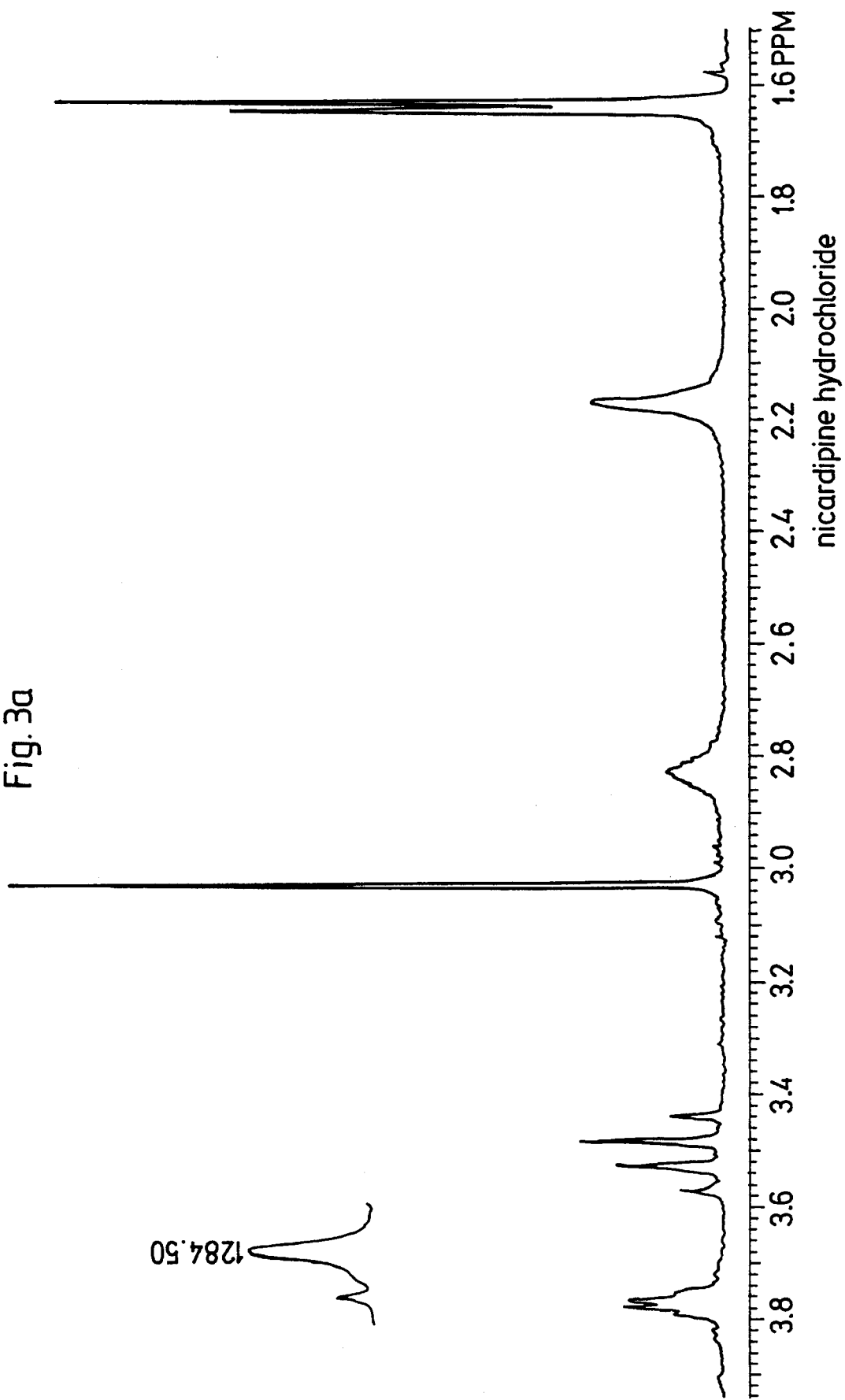
FIGS. 3a and 3b show the NMR specter of nicardipine hydrochloride.

The object of the invention is to convert dihydropyridine compounds, which are excellent coronary and cerebral vasodilators but are very poorly water soluble, into a substantially better water soluble form, whereby the preparation of galenic forms with improved biopharmaceutical properties such as excellent bioavailability is made possible.

This aim is achieved by inclusion of optically active and racemic dihydropyridines into the structure of methyl-β-cyclodextrin or other cyclodextrin derivatives such as hydroxy-alkylated β-cyclodextrins, or in case of amlodipine and nicardipine, also of β-cyclodextrin.

For preparing inclusion complexes there may be used different hydroxy-alkylated β-cyclodextrins, such as 2-hydroxypropyl-β-CD, 3-hydroxypropyl-β-CD, 2-hydroxyethyl-β-CD (abb. HE-β-CD) or 2,3-dihydroxypropyl-β-CD. As cyclodextrin derivatives also glycosyl-β-CD, maltosyl-β-CD or di-maltosyl-β-CD etc. may be used according to the invention.

Dihydropyridine compounds such as nifedipine, nitrendipine, nimodipine, nicardipine-hydrochloride, amlodipine besylate, felodipine, nivaldipine, benidipine etc., used in therapy, are well-known compounds described in the literature.

It is well-known that many active substances are capable to form inclusion complexes with β-cyclodextrins. J. Szejtli reports in I. Int. Symp. on Cyclodextrins, Budapest, 1981 (379) "A Forecast for application of cyclodextrins in the Pharma Industry" that about 10% of orally administered active substances are capable of forming complexes.

Inclusion complexes of several active substances with cyclodextrins are well-known from numerous literature data such as from brochures J. Szejtli, Cyclodextrins and their Inclusion Complexes, Akademiai Kiado, Budapest 1982 or J. Szejtli, Cyclodextrin technology (1988), Kliwer Academic Publishers.

Cyclodextrins are cyclic compounds consisting of 6, 7 or 8 glycopyranose units, bound with α-1,4-glycosidic linkages. They are characterized by cylindrical structure and special arrangement of hydroxyl groups, the outside surface of the cyclodextrin ring being hydrophilic and thus providing water solubility, whereas the inside surface thereof is lipophilic. Thus it is possible that other molecules referred to as "guest molecules" or parts thereof which are less polar than water (hydrophobic molecules) and have suitable dimensions, are included in the lipophilic cavity of the inside part of the cylindrical cyclodextrin molecule and form an inclusion complex. As native cyclodextrins (abb. CD), α-CD, β-CD and γ-CD should be mentioned. Among them β-CD is the most suitable due to its properties and also due to its price.

Because of relatively poor water solubility (1.8 g/100 ml water) of prior art derivatives and also their being unsuitable for parenteral forms, novel derivatives of native cyclodextrins have been prepared and, consequently, a better water solubility of CD alone was achieved and also the quantity of the active substance in a solutions was enhanced.

From DE-A-31 38 218 there are well-known methylated β-CD derivatives, i.e. methyl ethers such as monomethyl derivative containing 7 methoxy groups in the structure of β-CD, especially dimethyl derivative having 14 methoxy groups, namely heptakis-(2,6-di-O-dimethyl)-β-cyclodextrin (abb. DIMEB), which has esterified $C_2$—OH and $C_6$—OH groups in the structure of CD. In this way the water solubility of indometacin was enhanced for 20.4 times by means of DIMEB.

From EP-A-0149197 there are well-known galenic forms containing inclusion complexes of some active substances which are poorly soluble in water or are unstable, with etherified β-CD such as hydroxyethyl, hydroxypropyl or dihydroxypropyl derivatives of β-CD. Hydroxypropyl-β-cyclodextrin (abb. HP-β-CD) is especially suitable for parenteral application because of its good water solubility and outstanding non-toxicity.

The object of the invention are novel inclusion complexes of optically active and racemic 1,4-dihydropyridines of the formula

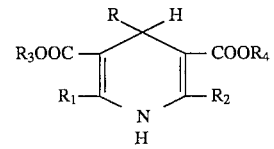

wherein

R represents a phenyl group, substituted with nitro, trifluoromethyl, difluoromethoxy group or with one or two halo atoms (especially chlorine), $R_1$ and $R_2$, if the same, represent methyl groups and if one of them has the meaning of a 2-aminoethoxymethyl or cyano group, the other represents a methyl group, $R_3$ and $R_4$, if different, stand each time for a hydrogen, linear or branched $C_1$–$C_6$-alkyl, 2-methoxyethyl, 1-(phenylmethyl)-3-piperidinylphenyl, styryl, furyl, piperidino, 4-diphenylmethyl-1-piperazinylethyl, 5-phenyl-3-pirazolyloxy, 1-phenyl-methyl-3-pyrrolidinyl group or a group of the formula

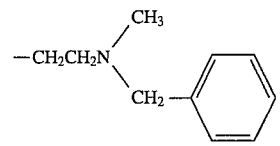

or, if the same, stand each time $C_1$–$C_4$ alkyl group, and of acid addition salts thereof with methyl-β-cyclodextrin (Me-β-CD), hydroxyethyl-β-cyclodextrin (HE-β-CD) or hydroxypropyl-β-cyclodextrin (HP-β-CD), with the exception of inclusion complexes of racemic dihydropyridines with HP-β-CD, or, in case of amlodipine and enantiomeric nicardipine, also with β-cyclodextrin (β-CD).

Examples of compounds of the formula I (racemic compounds and enantiomers) are 3-ethyl-5-methyl-1,4-dihydro-2,6-dimethyl-4-(3-nitrophenyl)-3,5-pyridinedicarboxylate (common name nitrendipine), isopropyl-2-methoxyethyl-1,4-dihydro-2,6-dimethyl-4-(3-nitrophenyl)-3,5-pyridinedicarboxylate (common name nimodipine), ethylmethyl-1,4-dihydro-2,6-dimethyl-4-(2,3-dichlorophenyl)-3,5-pyridinedicarboxylate (common name felodipine), 3-ethyl-5-methyl-2-[(2-aminoethoxy)methyl]-4-(2-chlorophenyl) 1,4-dihydro-6-methyl-3,5-pyridinedicarboxylate-monobenzensulfonate (common name amlodipine-monobenzensulfonate or amlodipine besylate), 5-isopropyl-3-methyl-2-cyano-1,4-dihydro-6-methyl-4-(3-nitrophenyl)-3,5-pyridinedicarboxylate (common name nivaldipine), 2-(N-benzyl-N-methyl-amino)-ethylmethyl-2,6-dimethyl-4-(3-nitrophenyl) -1,4-dihydropyridine-3,5-dicarboxylatehydrochloride (common name nicardipine hydrochloride), methyl-1-(phenylmethyl)-3-piperidinyl-1,4-dihydro-2,6-dimethyl-4 -(3-nitrophenyl)-3,5-pyridinedicarboxylate (common name bendipine).

Dimethyl-1,4-dihydro-2,6-dimethyl-4-(3-nitro-phenyl)-3,5-pyridinedicarboxylate (common name nifedipine) occurs only as a racemic compound.

Partly methylated β-cyclodextrin (Me-β-CD) is used for preparing novel inclusion complexes of dihydropyridines of the formula I, i.e. the methyl derivative of β-cyclodextrin with 7 methyl groups in the structure of β-CD, which is by far the best water soluble CD (80 g/100 ml of water at 25° C.) and, besides, it is also well soluble in organic solvents. It is also well soluble at elevated temperatures in contrast to other higher methylated ethers.

The inclusion complexes of dihydropyridines of the formula I, in the form of racemic compounds as well as in the form of (+) enantiomers and (−) enantiomers, with methyl-β-cyclodextrin (Me-β-CD) are novel compounds hitherto not described in the literature. The inclusions complexes of enantiomeric dihydropyridines with HP-β-CD and HE-β-CD are novel as well.

Inclusion complexes of cyclodextrins with dihydropyridines are hardly disclosed in the literature.

Poor results were achieved or even inability for complexing was established in the processes for preparing inclusion complexes of dihydropyridines such as nifedipine, nimodipine, nitrendipine etc. with native β-cyclodextrin. A rapid and good formation of a complex with β-CD was established in case of nicardipine hydrochloride as disclosed in EP-A-0324982.

There was further surprisingly established an easy and rapid preparation of an inclusion complex of amlodipine or salt thereof such as besylate salt, with β-CD.

In contrast to this easy complexing no complexes are formed with felodipine due to steric hindrances (2,3-dichlorophenyl group) as well as with other dihydropyridines (nitro group at phenyl nucleus).

From JP Kokai 88-218663 there are well-known inclusion complexes of dihydropyridines with hydroxypropyl-β-cyclodextrins and thus there is improved the water solubility of dihydropyridines which are otherwise poorly soluble in water. Inclusion complexes of enantiomeric dihydropyridines, i.e. (+) enantiomers and (−) enantiomers, with hydroxypropyl-β-cyclodextrin are, however, not disclosed in the literature.

Although the solubility of HP-β-CD in water is very high (50 g/100 ml of water at 25° C.), preferably Me-β-CD was used for complexing according to the invention due to its outstanding water solubility.

It has been found that inclusion complexes of dihydropyridines of the formula I in the racemic form as well as in the form of the enantiomers thereof, with Me-β-CD are by far better water soluble than well-known complexes of racemic dihydropyridines with β-CD or HP-β-CD disclosed in literature as evident from Table I. Particular enantiomers such as (−) nicardipine.HCl and (+) nicardipine.HCl also exhibit different water solubilities.

For this reason, according to the invention preferably inclusion complexes of racemic forms or enantiomers of dihydropyridines of the formula I with Me-β-CD were used for preparing galenic forms.

Figure 37:
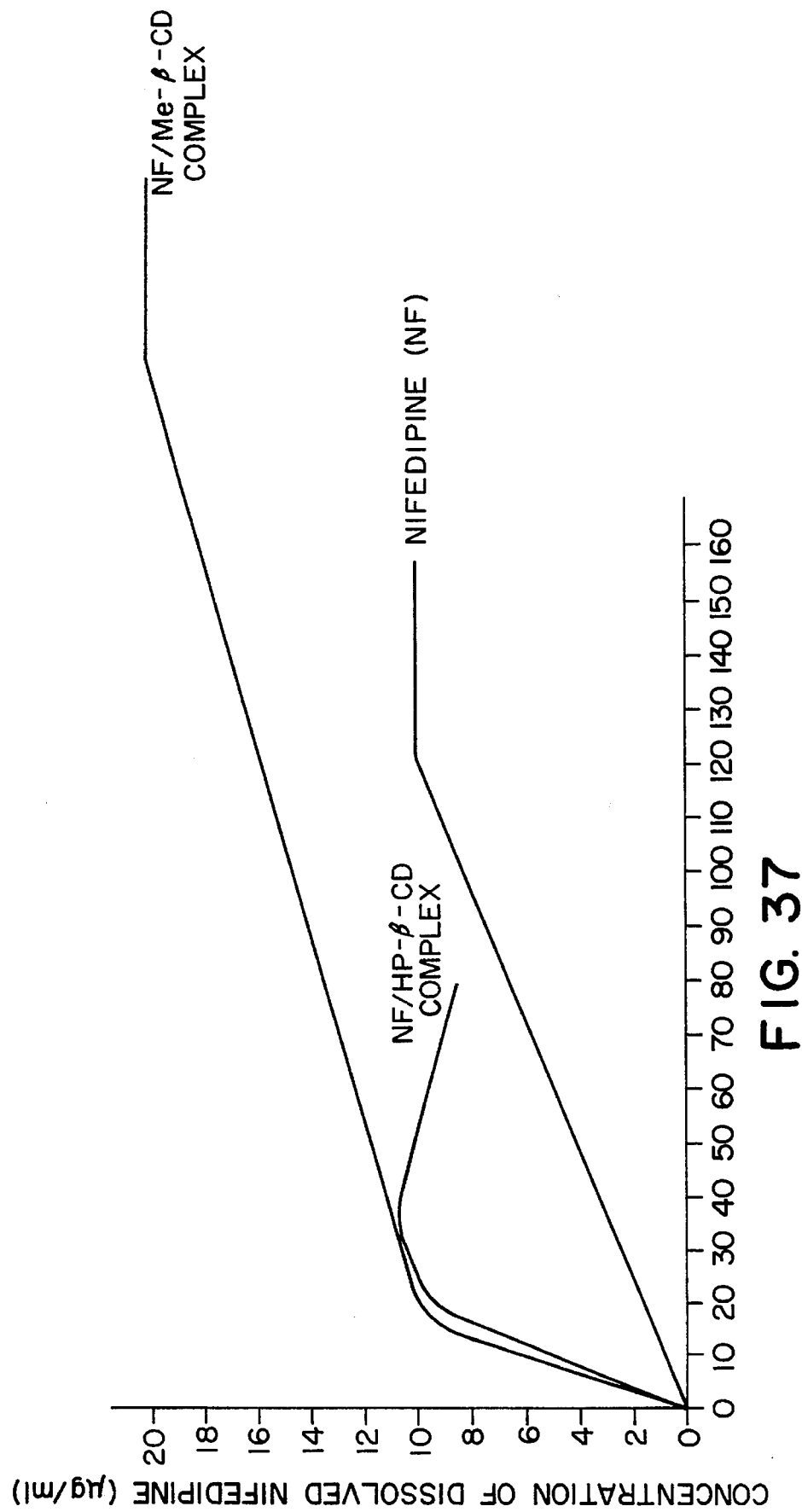
FIG. 37 compares the water solubility of unbound nifedipine (NF) and of nifedipine bound in complex with Me-β-CD (NF/Me-β-CD) and HP-β-CD (NF/HP-β-CD).
Figure 38:
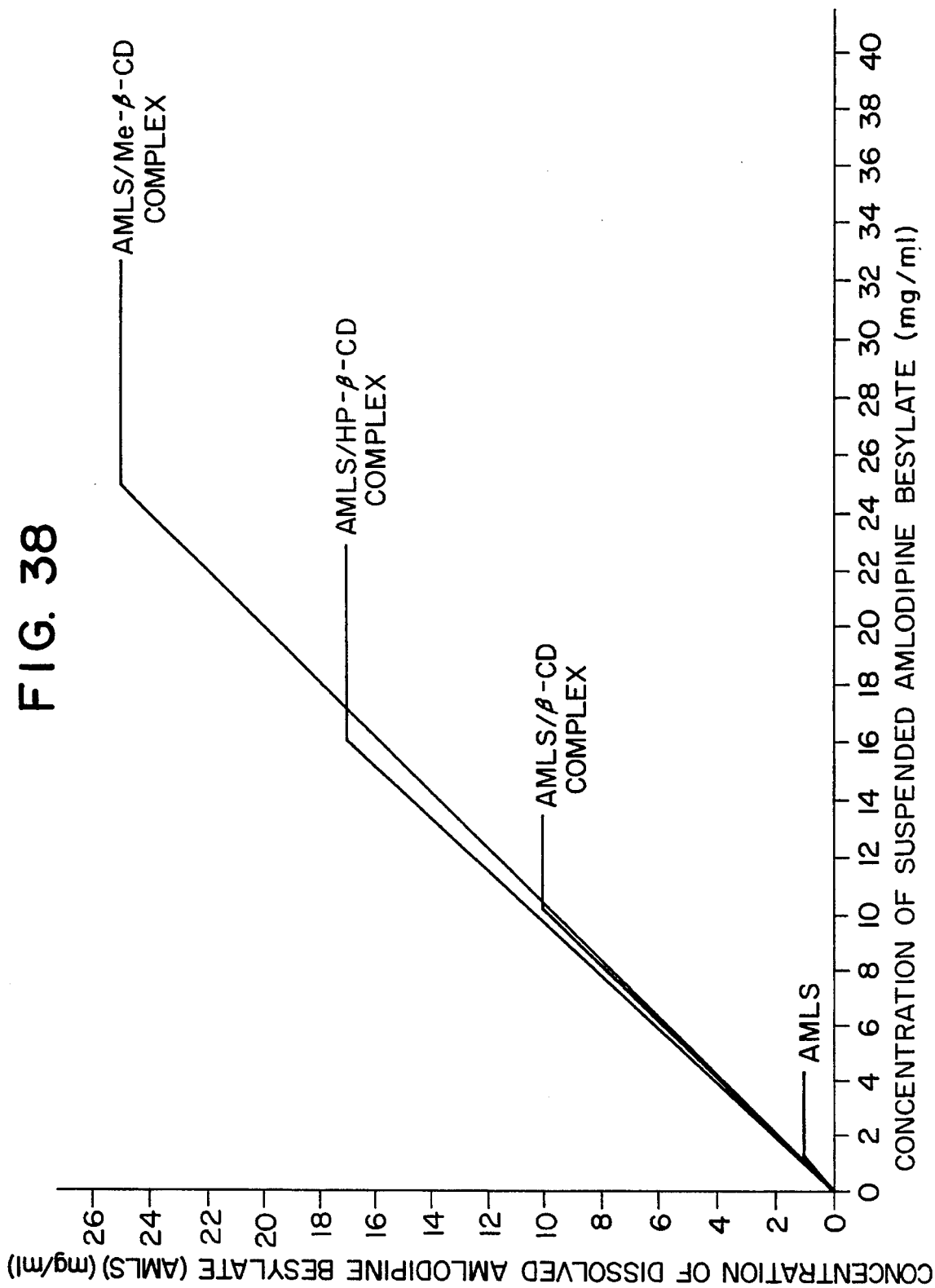
FIG. 38 compares the water solubility of unbound AML.S and of AML.S bound in complex with β-CD (AML.S/β-CD), HP-β-CD (AML.S/HP-β-CD) and Me-β-CD (AML.S/Me-β-CD).

The improved water solubility of inclusion complex of nifedipine and amlodipine besylate with Me-β-CD is evident from FIGS. 37 and 38.

All inclusion complexes of dihydropyridines either in racemic form or in the form of enantiomers with Me-β-CD, HE-β-CD, HP-β-CD or, in case of amlodipine and nicardipine, also with β-CD, are formed in equimolar ratio with complexing structural elements in the molecule of a particular DHP. In case of nicardipine hydrochloride also 2:1 complexes (molar ratio Me-β-CD, HE-β-CD or HP-β-CD:DHP) may be formed in addition to 1:1 complexes since it is complexed by a free phenyl ring in aromatic ester moiety and by a nitrophenyl group in 4-position of DHP ring. In general, also inclusion complexes of Me-β-CD, HE-β-CD, HP-β-CD and other β-CD derivatives or of mixtures of particular CD derivatives may be formed with dihydropyridines in the 2:1 ratio if DHP in its structure also has an aromatic part in the ester moiety in addition to the substituted phenyl ring in the 4-position.

Inventive inclusion complexes of racemic dihydropyridines are prepared according to the methods which are well-known for preparing inclusion complexes of active substances with cyclodextrins as disclosed e.g. in Chem. Pharm. Bull.23(12), 3062–3068/1975. To this effect, dihydropyridines are reacted with cyclodextrins under stirring at a temperature from about room temperature to the boiling point of the reaction mixture in an aqueous or methanolic medium, then cooled and the desired complex is isolated.

The invention further relates to a process for preparing enantiomerically pure dihydropyridines of the formula I and inclusion complexes thereof with Me-β-CD, HE-β-CD, HP-β-CD or, in case of amlodipine and nicardipine, also with β-CD, by means of preparative column chromatography.

Different processes for preparing optically active 1,4-dihydropyridines are disclosed in the literature (EP-A-0026317, EP-B-0166296, EP-A-0273349 and EP-A-0383320).

Racemic DHP or inclusion complexes thereof with β-CD or derivatives thereof are used in the preparation of enantiomerically pure DHP and inclusion complexes thereof with β-CD and derivatives thereof, resp., as starting components and samples, resp., for chromatographic separation. The chiral separation method by means of cyclodextrins as enantioselectors is well-known in the analytic chemistry only, whereas it is hardly known for preparative chromatographic enantioseparation.

The way of preparing enantiomeric complexes of DHP with β-CD and derivatives thereof, resp., as well as the enantioseparation of pure DHP according to the invention have not been disclosed in the literature so far.

According to this method the following four chromatographic systems given below may be used. For preparing each particular enantiomerically pure DHP or inclusion complex thereof there should be established which one of the given chromatographical systems is suitable for the preparation and isolation of the desired enantiomeric component. This necessitates a specific choice of the system for a particular starting DHP and the inclusion complex thereof, resp.

The particular processes are illustrated by means of Examples.

I.
Stationary phase (abb. SP):β-CD, pure or physically bound on an inert carrier such as silicagel (particles of a suitable size were prepared by means of lyophilization).
Mobile phase (abb. MP): water or a mixture of water and aliphatic lower alcohols (methanol, ethanol etc.), saturated with β-CD or β-CD derivatives (Me-β-CD, HP-β-CD etc.).
Sample (abb. PR): inclusion complex of a racemic DHP with different cyclodextrins (β-CD, Me-β-CD, HP-β-CD) or racemic DHP.
II.
SP: copolymer of epichlorohydrin with β-CD
MP: water, a mixture of water and aliphatic lower alcohols or only aliphatic lower alcohols.

PR: racemic DHP or an inclusion complex thereof with β-CD, Me-β-CD or HP-β-CD.

III.

SP: RP-18 (reversed phase silicagel).

MP: water, water-acetonitrile mixture, a mixture of water and aliphatic lower alcohols, phosphate buffer with pH from 6 to 9; mobile phase always contains β-CD, Me-β-CD or HP-β-CD in a concentration from 5 moles to saturation.

PR: racemic DHP or inclusion complex thereof with β-CD, Me-β-CD or HP-β-CD.

IV.

SP: racemic DHP or inclusion complex thereof with β-CD, Me-β-CD or HP-β-CD, vaporized in vacuo on silicagel, which simultaneously represents a sample for enantioseparation.

MP: water, a mixture of water and aliphatic lower alcohols.

PR: racemic DHP, vaporized on a carder of a stationary phase.

For preparing chromatographic systems and for elution glass columns were used for operating at normal, elevated ("$N_2$ flashing") or reduced pressure ("dry flashing");

the stationary phase was charged dry or as a thick suspension into the column in the mobile phase;

the sample was applied onto the stationary phase dry in the pure form or as dry inclusion complex or as a dry physical mixture of the pure dry DHP and of β-CD or derivative thereof or as a saturated solution of the pure DHP or the inclusion complex thereof with β-CD or β-CD derivatives and the ratio of the stationary phase and the sample amounted to from 30:1 to 150:1;

the mobile phase was optionally saturated with a suitable β-CD derivative and the sample was eluted with a constant flow of the mobile phase, which flow was from 0.1 to 1 ml/min.

According to the chromatographic method used, eluates of the following composition were treated:

The eluates obtained were aqueous solutions of inclusion complexes of enantiomeric DHP with a corresponding cyclodextrin such as β-CD, Me-β-CD or HP-β-CD, with the excessive free cyclodextrin from the mobile and/or stationary phase being present.

The HPLC analysis showed that dry substances of the eluates contained 1 to 20% DHP. In $^1$H NMR spectra there were noticeable characteristic shifts for molecule moieties of DHP forming an inclusion complex. Dynamic scanning calorimetry (DSC) of eluates showed no traces of free DHP enantiomers.

From the obtained eluates either an inclusion complex of the enantiomeric DHP with β-CD or a derivative thereof or the free enantiomer of DHP with great purity (not bound in a complex) may be isolated. Therefore for a further isolation only combined eluates were used, which were found in a preliminary HPLC analysis (on the basis of detection upon the principle of the circular dichroism) to contain the desired DHP enantiomer with a satisfactory purity. The isolation process was selected with regard to the product to be isolated. If the inclusion complex of the enantiomeric DHP with β-CD or derivatives thereof (Me-β-CD, HE-β-CD, HP-β-CD) was to be isolated from the eluates, the eluates might be evaporated to dryness or lyophilized. The dry substance was suspended in a solvent, which selectively dissolved either the inclusion complex of the enantiomeric DHP with β-CD or with derivatives thereof or the free (excessive) cyclodextrin; the dry substance of the eluate, however, might also be recrystalized.

Possible cyclodextrin traces might be eliminated from the desired product by means of column chromatography on the conventional or RP-18 derivated silicagel.

If from the eluates free DHP enantiomers were to be isolated, the combined eluates might be evaporated to dryness or lyophilized. The dry substance was suspended in a solvent decomposing the inclusion complexes of the enantiomeric DHP with β-CD or derivatives thereof (Me-β-CD, HE-β-CD, HP-β-CD) and selectively dissolving only one component of the decomposed inclusion complex (only DHP or β-CD or a derivative thereof). Optionally alkalis or acids might be added to the solvent to adjust the pH of the medium if such a manner was necessary for decomposing the complex and for achieving a different solubility of DHP or β-CD or a derivative thereof.

The undissolved component (DHP or β-CD or a derivative thereof) was filtered off and the precipitate was washed with the solvent.

The solvent, either selectively dissolving the inclusion complex of DHP or free cyclodextrin or decomposing inclusion complexes of DHP so that said solvent selectively dissolved only one component of the decomposed inclusion complex, was to be again selected for each starting DHP and that should be established according to the invention. These solvents are given in Examples.

In order to isolate the free enantiomer of DHP present in the precipitate, the precipitate was dried in vacuo and, optionally, the present DHP was converted into a salt thereof or into the desired acid (for formation or for decomposition of salts) and than the desired product was lyophilized.

When the enantiomeric DHP was dissolved in mother liquor, the latter was evaporated to dryness, the product was washed with a solvent dissolving only β-CD or a derivative thereof and not the desired DHP, and dried to constant weight. DHP might be then optionally converted to the acid addition salt thereof and the desired product was finally recrystallized.

The desired enantiomer of DHP was obtained by this process with great purity since the accompanying substances such as cyclodextrins were completely eliminated.

The invention also relates to pharmaceutical formulations having cerebrovascular-vasodilatatory and/or coronary-vasodilatatory effect and containing a therapeutically effective amount of an inclusion complex of racemic DHP or enantiomers thereof of the formula I or acid addition salts thereof with methyl-β-cyclodextrin, hydroxyethyl-β-cyclodextrin or hydroxypropyl-β-cyclodextrin, with the exception of inclusion complexes of racemic DHP with HP-β-CD, or, in case of amlodipine and enantiomeric nicardipine also with β-CD, together with a pharmaceutically acceptable carrier and other conventional auxiliary substances.

Pharmaceutical formulations are suitably present in dosis forms. Therapeutical doses of DHP included in complexes are equivalent to doses present in commercial formulations of racemic DHP.

In addition to already disclosed advantages, cyclodextrins also represent a carrier basis for DHP, nevertheless the therapeutical doses of DHP need not be changed. In contrast to racemic DHP or the inclusion complexes thereof, doses of therapeutically active enantiomers of DHP bound in complexes are significantly lower, corresponding to the activity grade of one enantiomer with respect to the other one. Due to their use, also the weight portions of different cyclodextrins complexed with enantiomeric DHP, are in dose units significantly lower than by using racemic DHP.

When using solid dose units on the basis of inclusion complexes of certain known active substances (especially of those requiring higher doses) with cyclodextrins, excessive weight or size of the galenic form (cca 1 g or more) is inconvenient in certain cases since it may cause application difficulties with patients. The use of lower therapeutical doses of enantiomeric DHP and, consequently, smaller weight or size of solid dose units, which is the result of smaller weight used of the cyclodextrins in complexing, for achieving the same therapeutical effect as in the application of racemic DHP, represents a valuable improvement in the therapy with dihydopyridines. One skilled in the art could further expect that, due to the elimination of a therapeutically inactive or less active enantiomer of DHP, the possibility of undesired parallel effects is reduced if only a therapeutically more active enantiomer is used for therapeutical purposes.

Suitable forms of pharmaceutical formulations are solid dose forms such as tablets with an instant release or sustained release of the active substance, effervescent tablets or dispersion tablets, capsules. The preparation of parenteral forms is possible only with inventive inclusion complexes with HP-β-CD.

These formulations may also contain, in addition to the active substance, conventional pharmaceutically acceptable carriers and auxiliary substances, e.g. diluents such as lactose, dextrose etc., lubricants such as talcum, stearic acid and salts thereof, polyethylene glycole, binders, fillers, colourants etc.

Formulations may be prepared according to well-known methods such as stirring, granulating, dissolving etc.

The invention is illustrated in detail by the following Examples, however not limited thereto.

EXAMPLE 1

Preparation of inclusion complex of nicardipine hydrochloride (NC.HCl) with methyl-β-cyclodextrin (Me-β-CD)

Methyl-β-cyclodextrin (0.510 g; 0.389 mmole) was dissolved in distilled water (20 ml) and nicardipine hydrochloride (0.200 g; 0.387 mmole) was added under stirring. The reaction mixture was then heated to a temperature of 65° C. and stirred for 20 minutes at this temperature. An almost clear solution was slowly cooled down and allowed to stand overnight. Then it was filtered off, the filtrate was frozen and dried to a dry product by lyophilization. A yellow microcrystalline product (0.6 g; 84.5%) with m.p. 145°–152° C. (not sharp) was obtained.

Dynamic scanning calorimetry (DSC thermogram)

In the curve (FIG. 1) no endothermic pass for a physical NC.HCl/Me-β-CD mixture at 160°–170° C. was detectable.

NMR specter

In $^1$H-NMR specter of complex in D$_2$O solution the following changes in nicardipine part were observed:

at 7.2–7.35 ppm a signal for the resonances of protons in free phenyl ring was broadened and shifted to a higher field (FIG. 2).

Figure 3B:
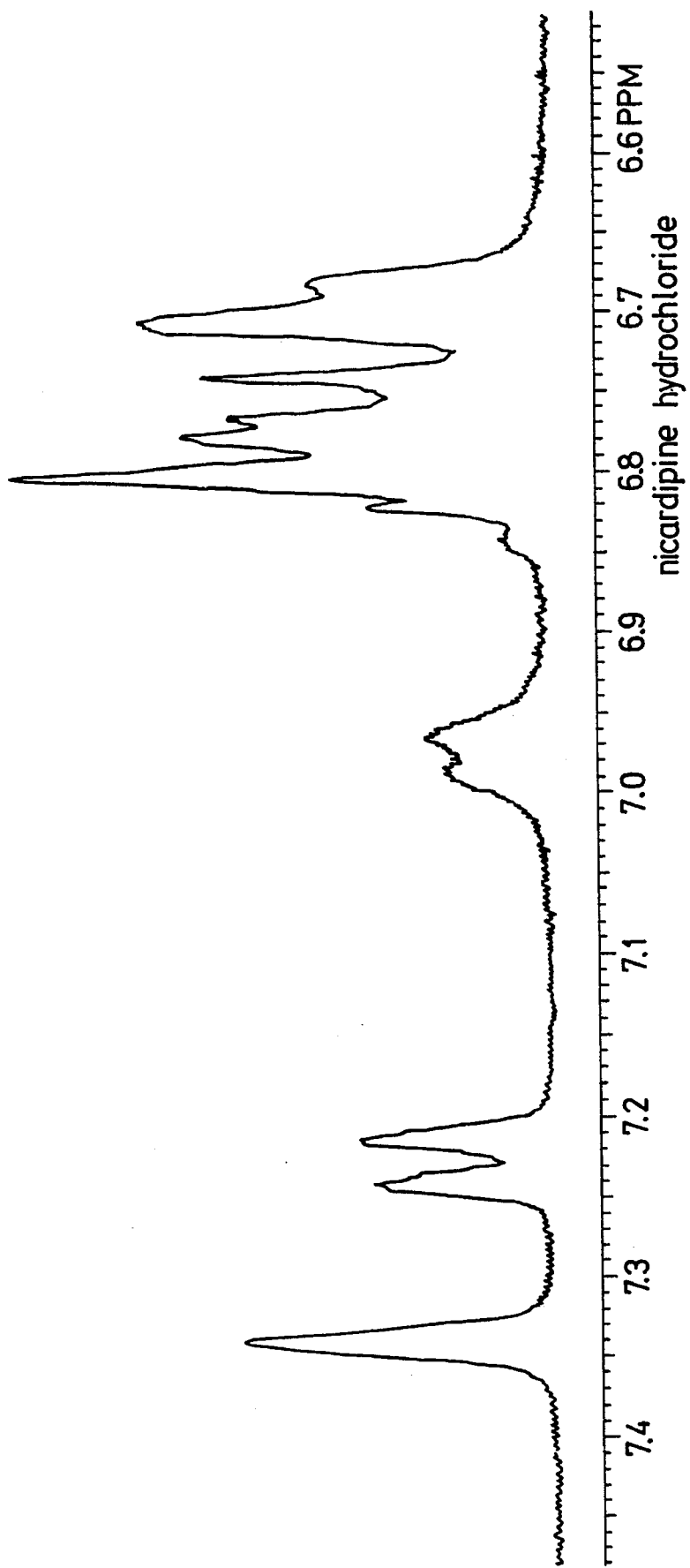

FIG. 3a and 3b illustrate the specter of nicardipine hydrochloride.

EXAMPLE 2

Preparation of inclusion complex of nifedipine with methyl-β-cyclodextrin (Me-β-CD)

a) Procedure in an aqueous medium

Methyl-β-cyclodextrin (0.300 g; 0.229 mmole) was dissolved in distilled water (10 ml) and nifedipine (0.080 g; 0.229 mmole) was added in the dark under stirring. The suspension was heated for 2 hours at the boiling point. The clear solution obtained was slowly cooled down and put into a refrigerator overnight. The small quantity of the precipitate formed was filtered off. The filtrate was evaporated to a dry product in vacuo at 40° C. A yellow microcrystalline product (0.290 g; 76%) with m.p. 135°–145° C. (not sharp) was obtained.

b) Procedure in a methanolic medium

Methyl-β-cyclodextrin (0.300 g; 0.229 mmole) was dissolved in methanol (10 ml) and nifedipine (0.080 g; 0.229 mmole) was added in the dark under stirring. The reaction mixture was heated for 1 hour at the boiling point, then cooled down and put into refrigerator overnight. A still clear solution was evaporated to a dry product in vacuo at 40° C. The desired compound (0.320 g; 84.2%) with m.p. 138°–145° C. (not sharp) was obtained.

Dynamic scanning calorimetry (DSC thermogram)

Figure 4:
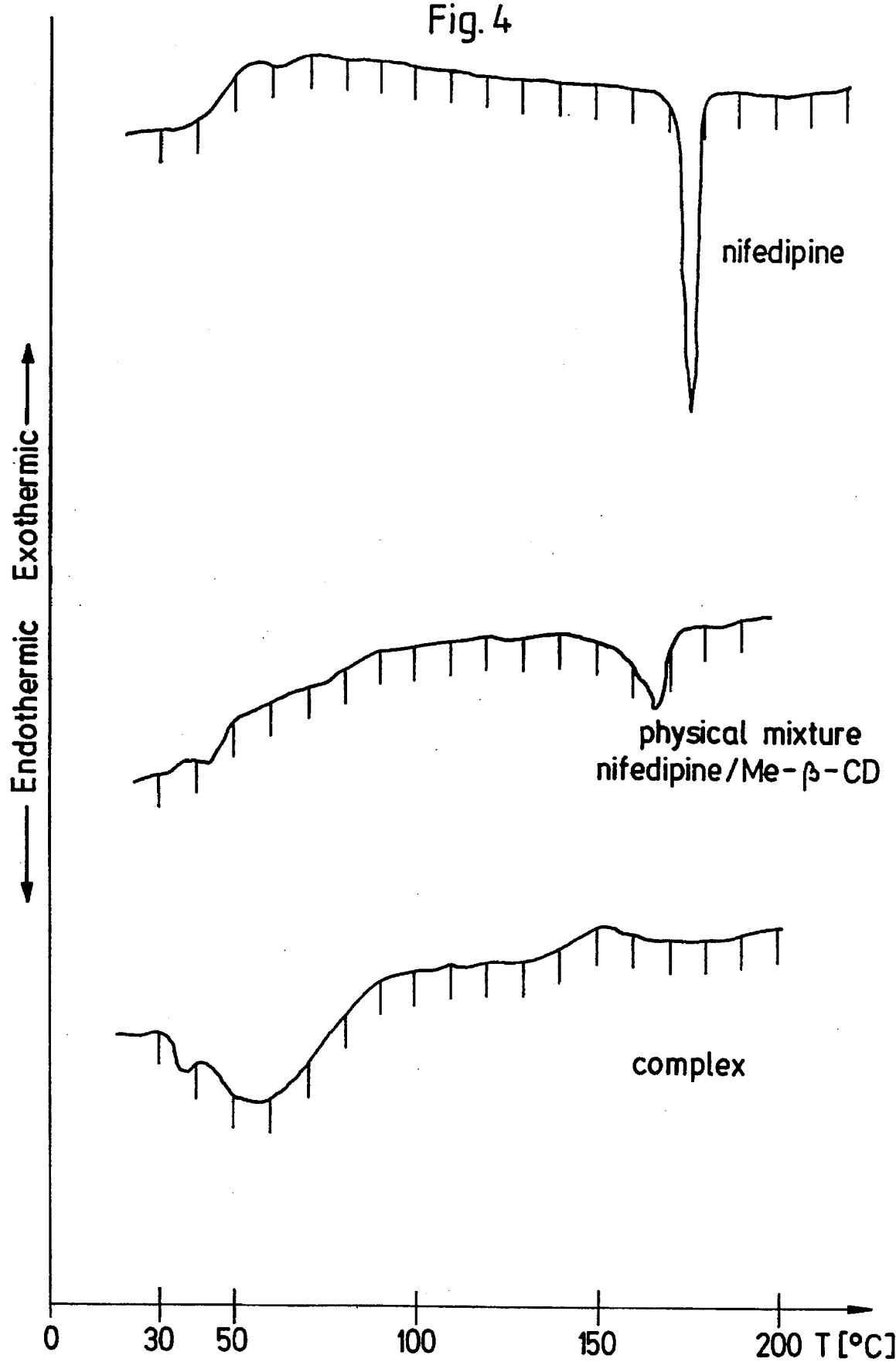
FIG. 4 depicts the DSC thermogram of nifedipine (top), a physical nifedipine/Me-β-CD mixture (center) and a nifedipine/Me-β-CD complex (bottom).

In the curves (FIG. 4) of DSC thermograms of the desired compound prepared by both procedures, no endothermic passes for the m.p. of the physical mixture of nifedipine-Me-β-CD were detectable at 160°–170° C.

Figure 6A:
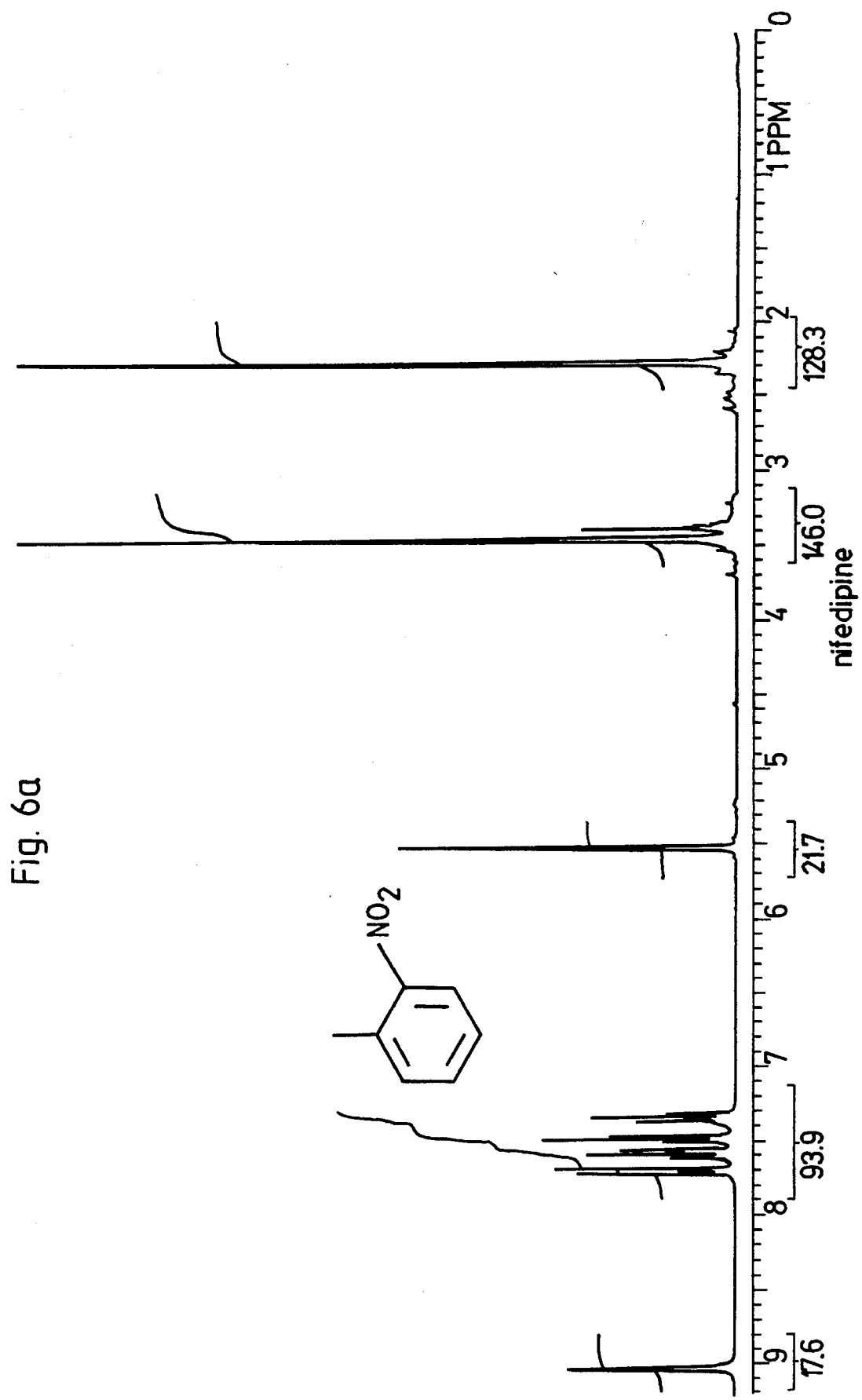
FIGS. 6a and 6b show the NMR specter of nifedipine.
Figure 6B:
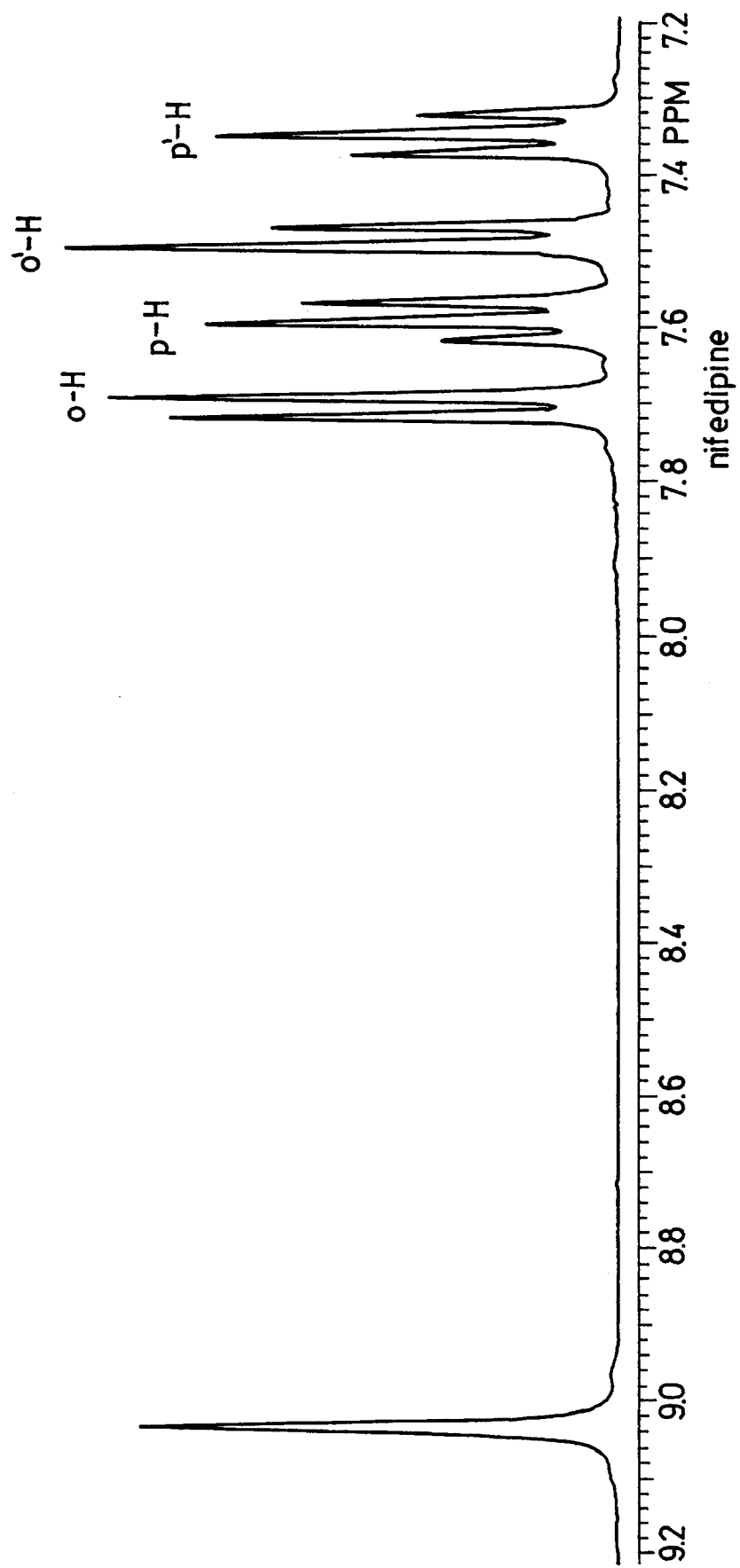

In FIG. 5 $^1$H-NMR specter of the desired complex and in FIG. 6a and 6b of nifedipine alone is represented.

EXAMPLE 3

Preparation of inclusion complex of felodipine with methyl-β-cyclodextrin (Me-β-CD)

To a solution of methyl-β-cyclodextrin (0.655 g; 0.5 mmole) in methanol (10 ml) felodipine (0.192 g; 0.5 mmole) was added. This reaction mixture was heated for 1 hour at the boiling point, then cooled down and put into refrigerator overnight. The slightly clouded solution was filtered and the filtrate was evaporated to a dry product in vacuo. A light yellow microcrystalline desired product (0.750 g; 88.5%) with m.p. 140° C. (not sharp) was obtained.

Dynamic scanning calorimetry (DSC thermogram)

Figure 7:
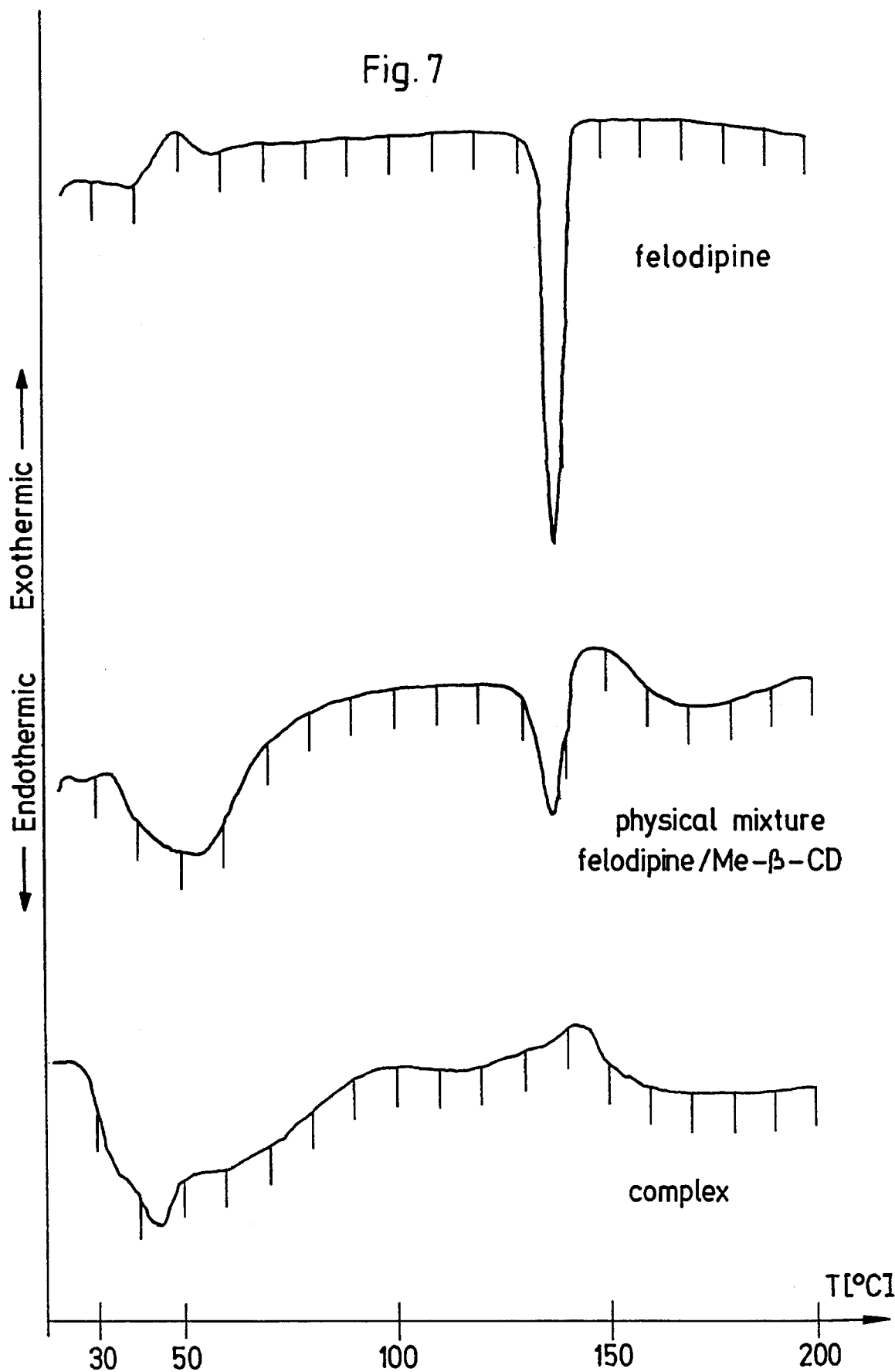
FIG. 7 depicts the DSC thermogram of felodipine (top), a physical felodipine/Me-β-CD mixture (center) and a felodipine/Me-β-CD complex (bottom).

In the curve (FIG. 7) of the desired product no endothermic pass for the m.p. of the physical mixture of felodipine-Me-β-CD at 130°–140° C. was detectable.

NMR specter

Figure 8:
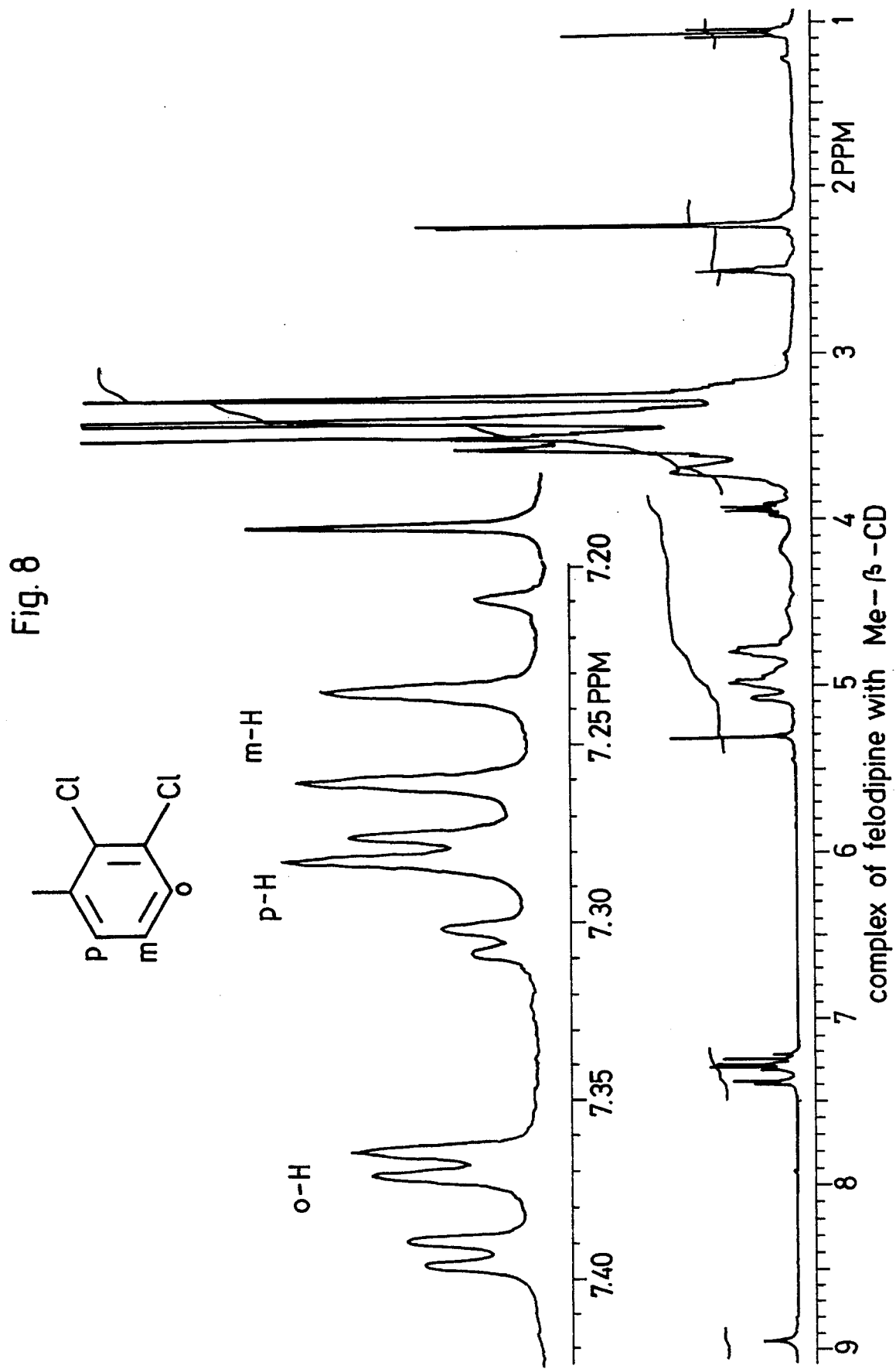
FIG. 8 shows the $^1$H-NMR specter of an inclusion complex of felodipine with Me-β-CD.
Figure 9:
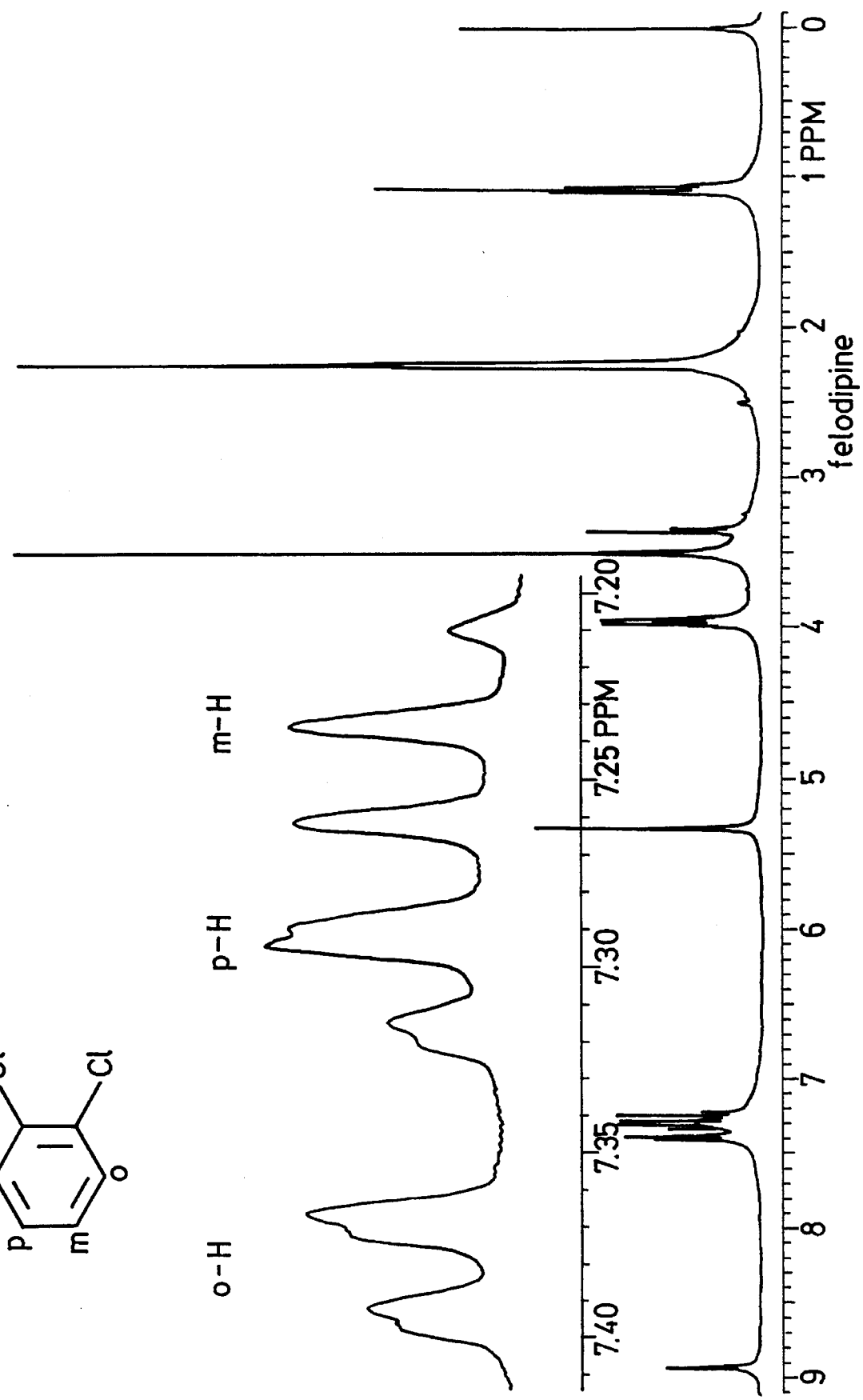
FIG. 9 shows the NMR specter of felodipine.

In $^1$H-NMR specter (FIG. 8) of the title complex in the DMSO solution, the following changes in felodipine moiety were observed:

due to the enantiotropic effect of Me-β-CD, the signals for resonances of hydrogens in the dichlorophenyl ring were doubled:
7.36–7.4 ppm doubled doublet for o—H,
7.27–7.31 ppm doubled doublet of a doublet for p—H.
The specter of felodipine alone is represented in FIG. 9.

EXAMPLE 4

Preparation of inclusion complex of amlodipine maleate (AML.M) with methyl-β-cyclodextrin (Me-β-CD)

Amlodipine maleate (50 mg; 0.095 mmole) was suspended in distilled water (20 ml) and methyl-β-cyclodextrin (200 mg; 0.153 mmole) was slowly added. The reaction mixture was then stirred for 2 hours at the temperature of 60° C. and slowly cooled down. The almost clear solution was filtered. The filtrate was evaporated to a dry product in vacuo. A white microcrystalline desired product (230 mg; 92%) with m.p. 210° C. (dec.) was obtained.

Dynamic scanning calorimetry (DSC thermogram)

In the DSC curve of the desired product, no endothermic pass for the m.p. of the physical mixture of amlodipine maleate/Me-β-CD at 170°–180° C. was detectable.

NMR specter the change of the shift of doublet for C—H ortho from chlorine atom on the chlorophenyl ring—for 0.03 ppm;

the shift of doublet for C—H in 6 position on the chlorophenyl ring for 0.01 ppm;

the shift of a signal for C—H in 4 position in the chlorophenyl ring for 0.01 ppm

EXAMPLE 5

Preparation of inclusion complex of amlodipine besylate (AML.S) with methyl-β-cyclodextrin (Me-β-CD)

Amlodipine besylate (0.55 g; 0.97 mmole) was suspended in distilled water (50 ml) and to the suspension methyl-β-cyclodextrin (1.31 g; 1 mmole) was added under stirring. The reaction mixture was stirred for 2 hours at room temperature and then for another hour at the temperature of 70° C., slowly cooled down and left overnight at room temperature. The precipitate formed was filtered and the filtrate was evaporated to a dry product in vacuo at 50° C. A white microcrystalline desired product (1.79 g; 95.7%) with m.p. 155°–165° C. (dec.) was obtained.

EXAMPLE 6

Preparation of inclusion complex of amlodipine besylate (AML.S) with β-cyclodextrin (β-CD)

Amlodipine besylate (0.55 g; 0.97 mmole) was suspended in distilled water (50 ml) and to the suspension β-cyclodextrin (1.24 g)(1.04 mmole+1.5% water) was added under stirring. The reaction mixture was heated up to 70° C. and then stirred at this temperature for 2 hours. It was slowly cooled down and left at room temperature overnight. The precipitate obtained was filtered and the filtrate was evaporated to a dry product in vacuo at 50° C. A white microcrystalline desired product (1.68 g; 93.8%) with m.p. 203°–206° C. (dec.) was obtained.

Dynamic scanning calorimetry (DSC thermogram)

Figure 10:
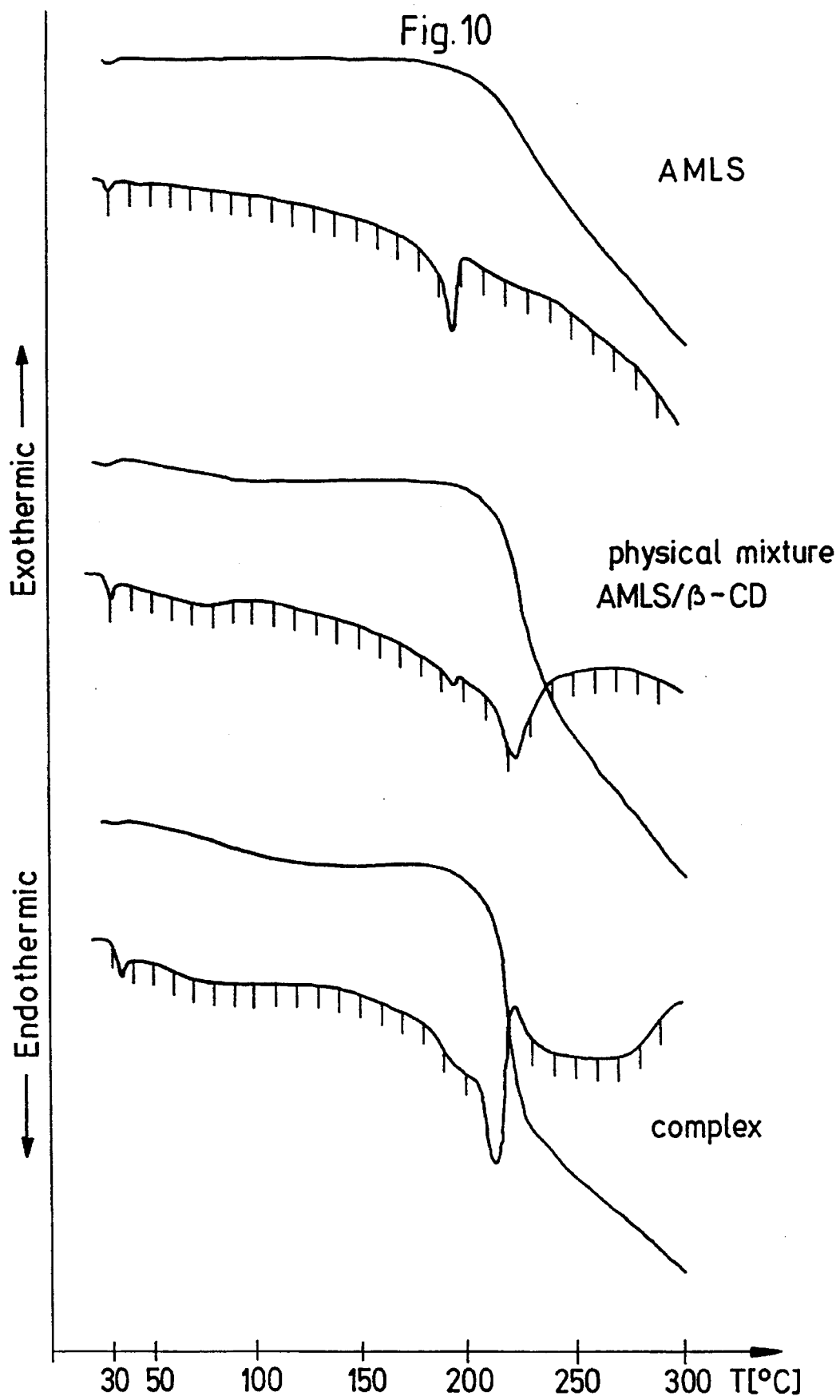
FIG. 10 depicts the DSC thermogram of amlodipine besylate (AML.S) (top), a physical AML.S/β-cyclodextrin (β-CD) mixture (center) and a AML.S/β-CD complex (bottom).

In the DSC curve (FIG. 10) of the desired product, no endothermic pass for the m.p. of the physical mixture of amlodipine besylate/β-CD at 190°–200° C. was detectable. An endothermic pass for the m.p. and a decomposition of a complex occured at 200°–220° C.

$^1$H-NMR spectra

Figure 11A:
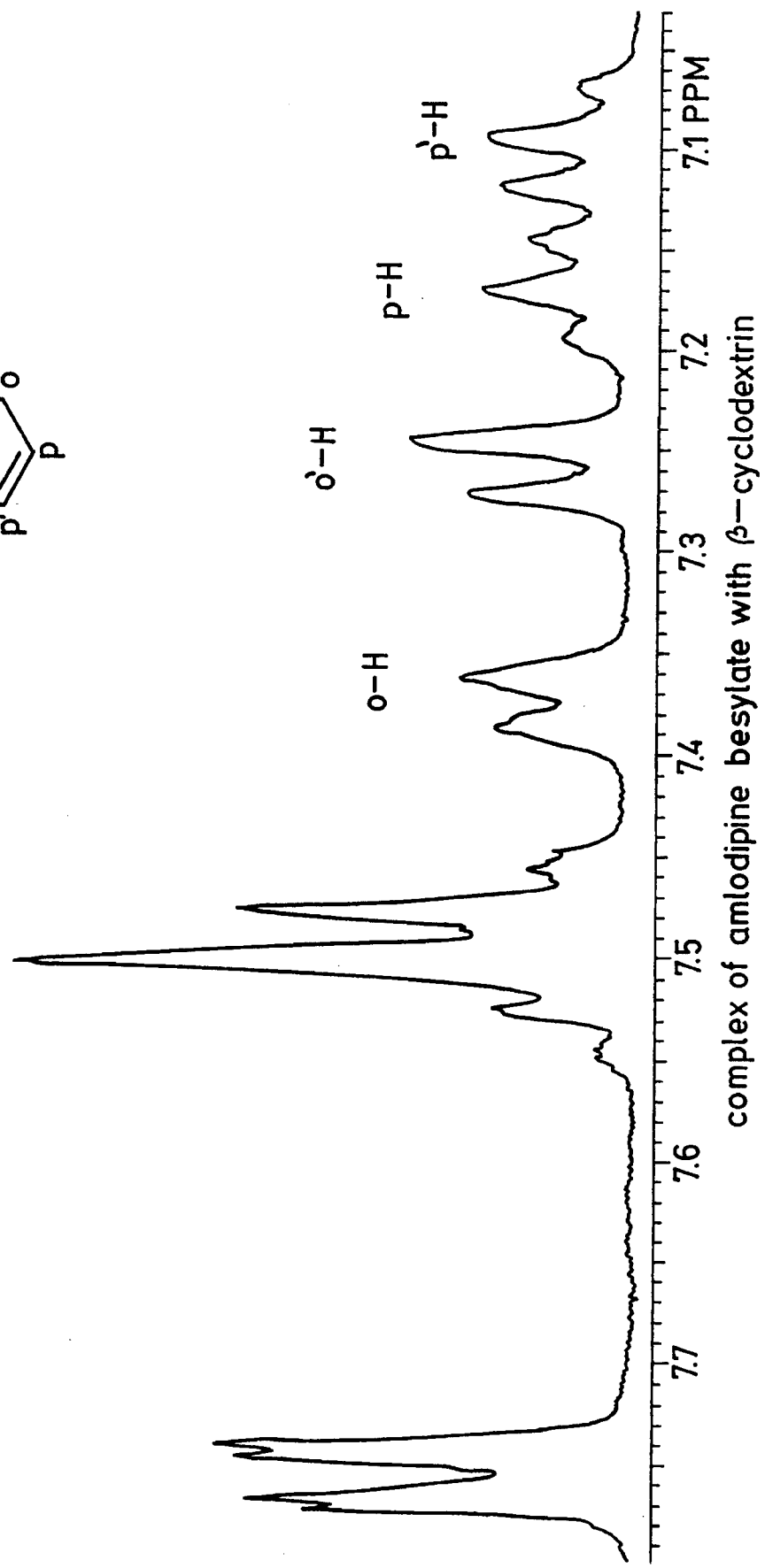
FIG. 11a and 11b show the $^1$H-NMR specter of an inclusion complex of AML.S with β-CD.
Figure 11B:
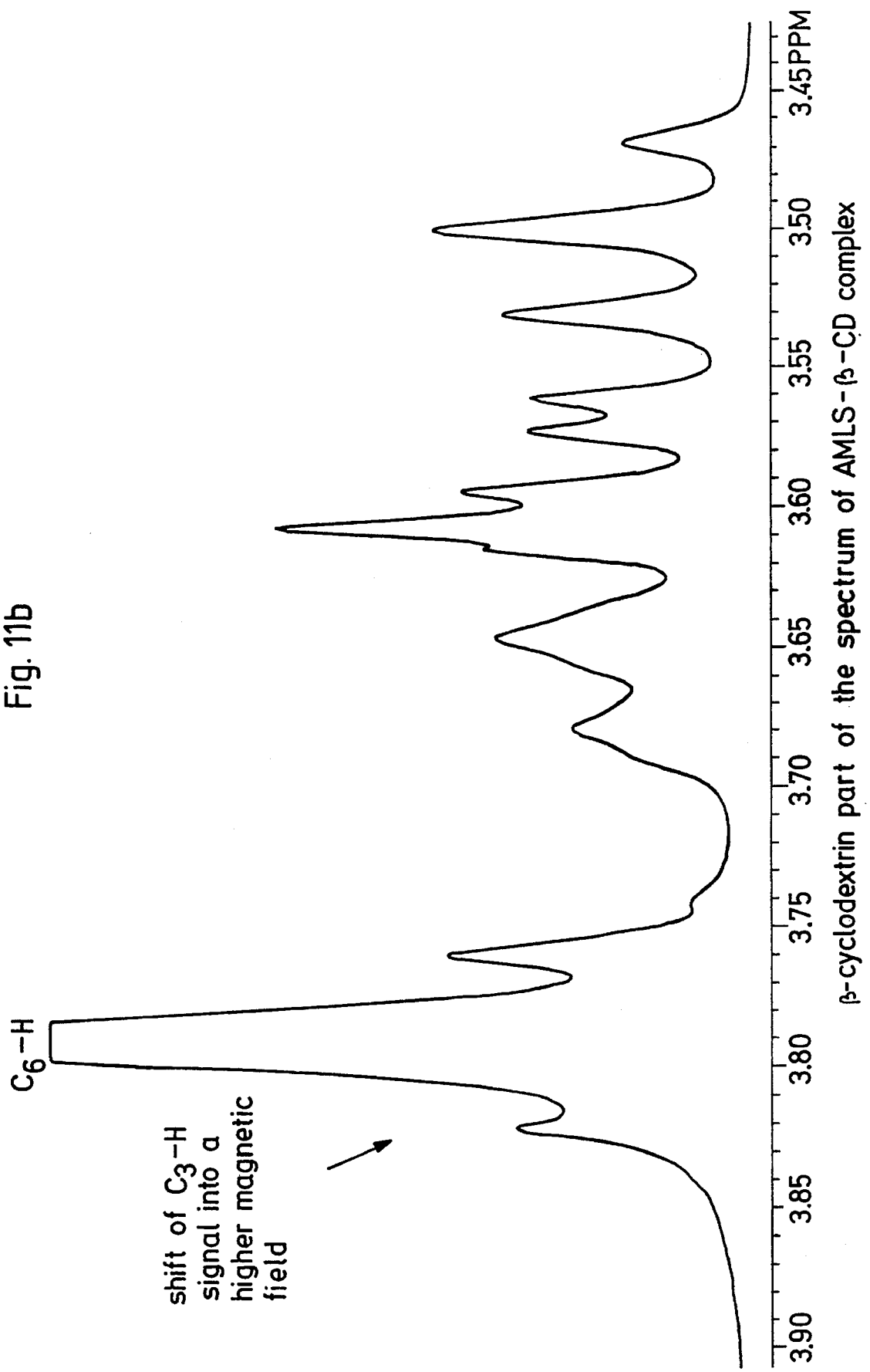
Figure 13:
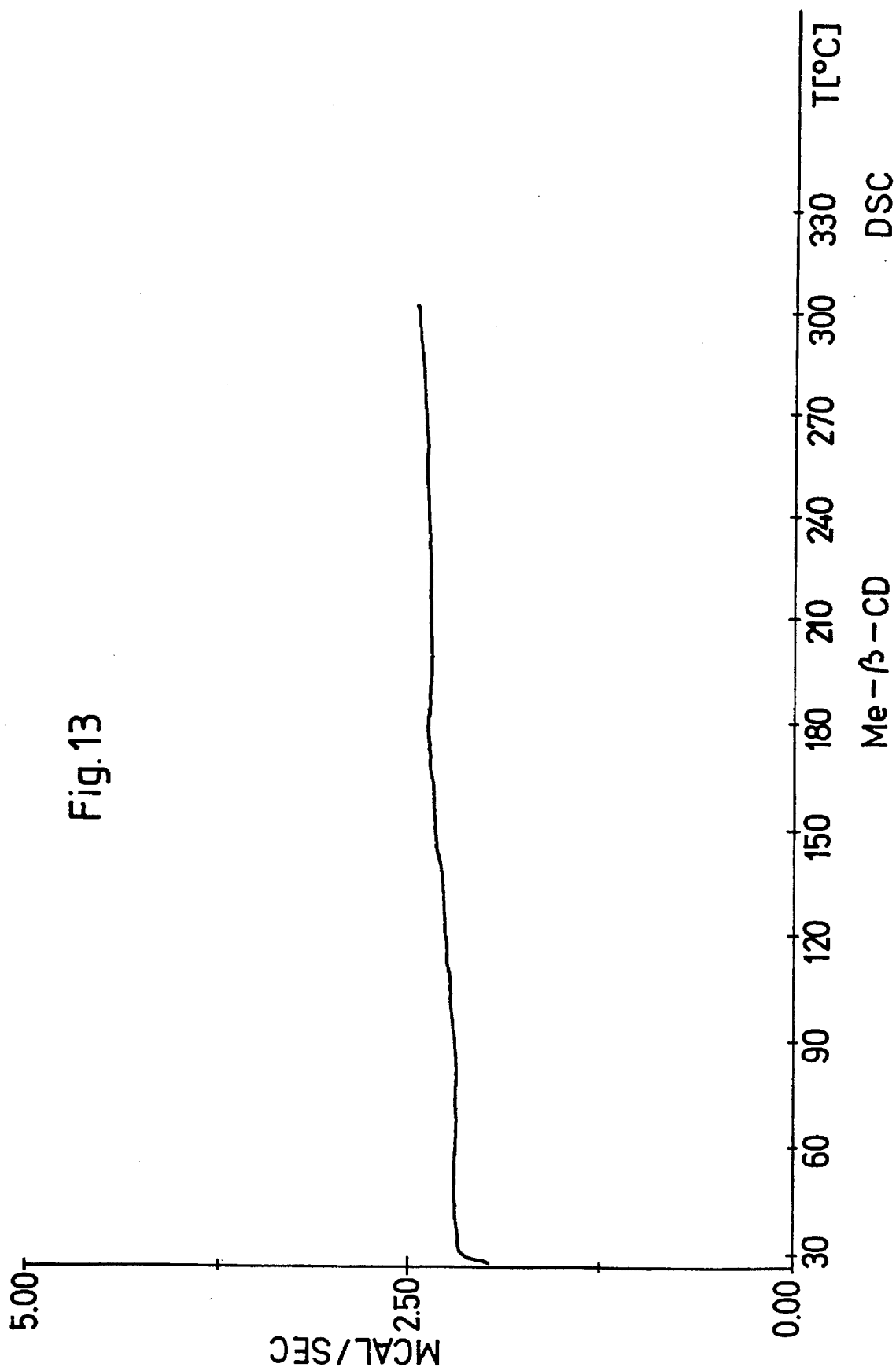
FIGS. 13 to 28 show DSC thermograms of inclusion complexes of enantiomers and racemates of nitredipine and nicardipine hydrochloride with Me-β-CD and hydroxy-propyl-β-cyclodextrin (HP-β-CD), respectively, as well as of the free active substance (enantiomers and racemate).
Figure 14:
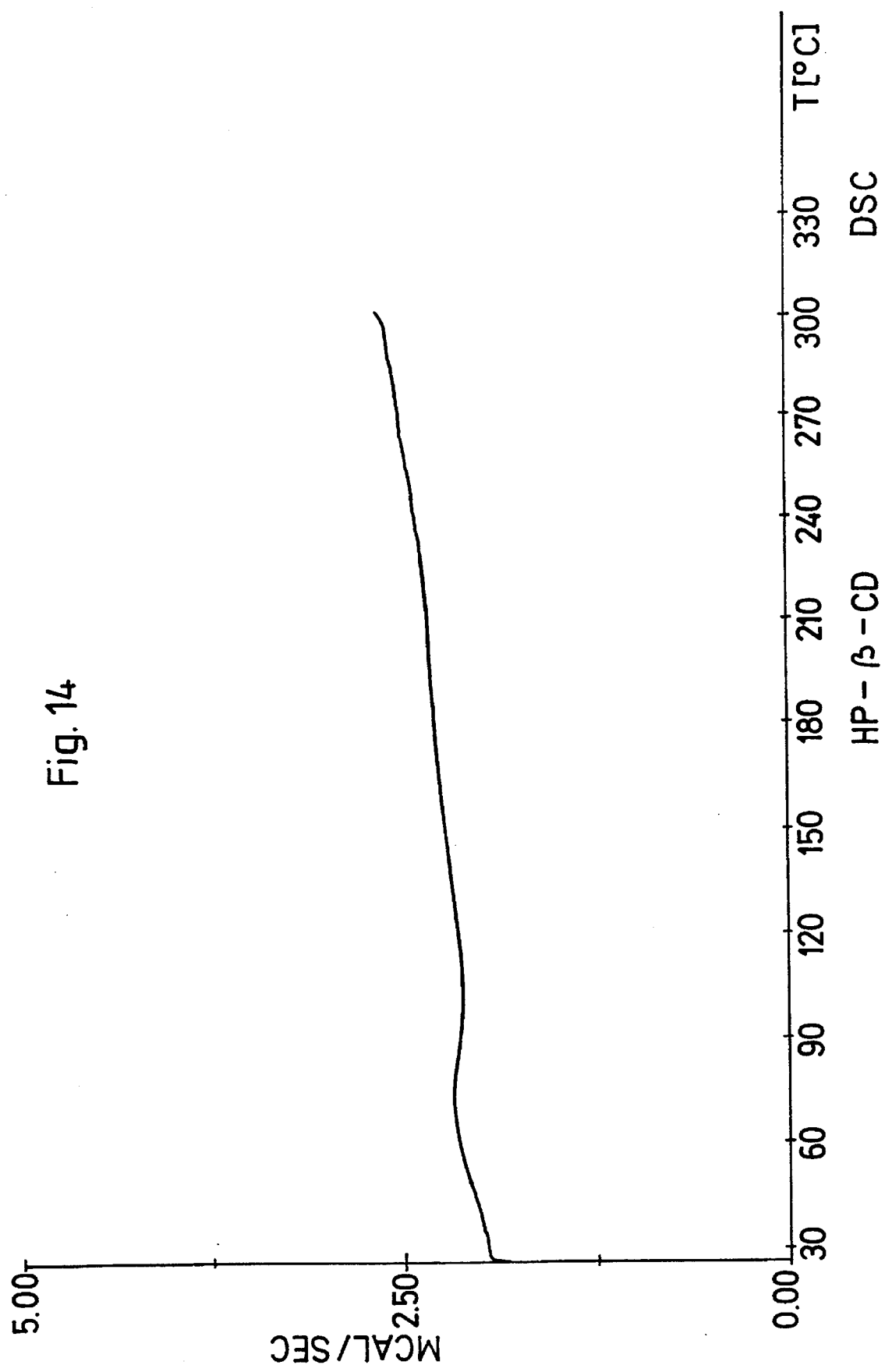
Figure 15:
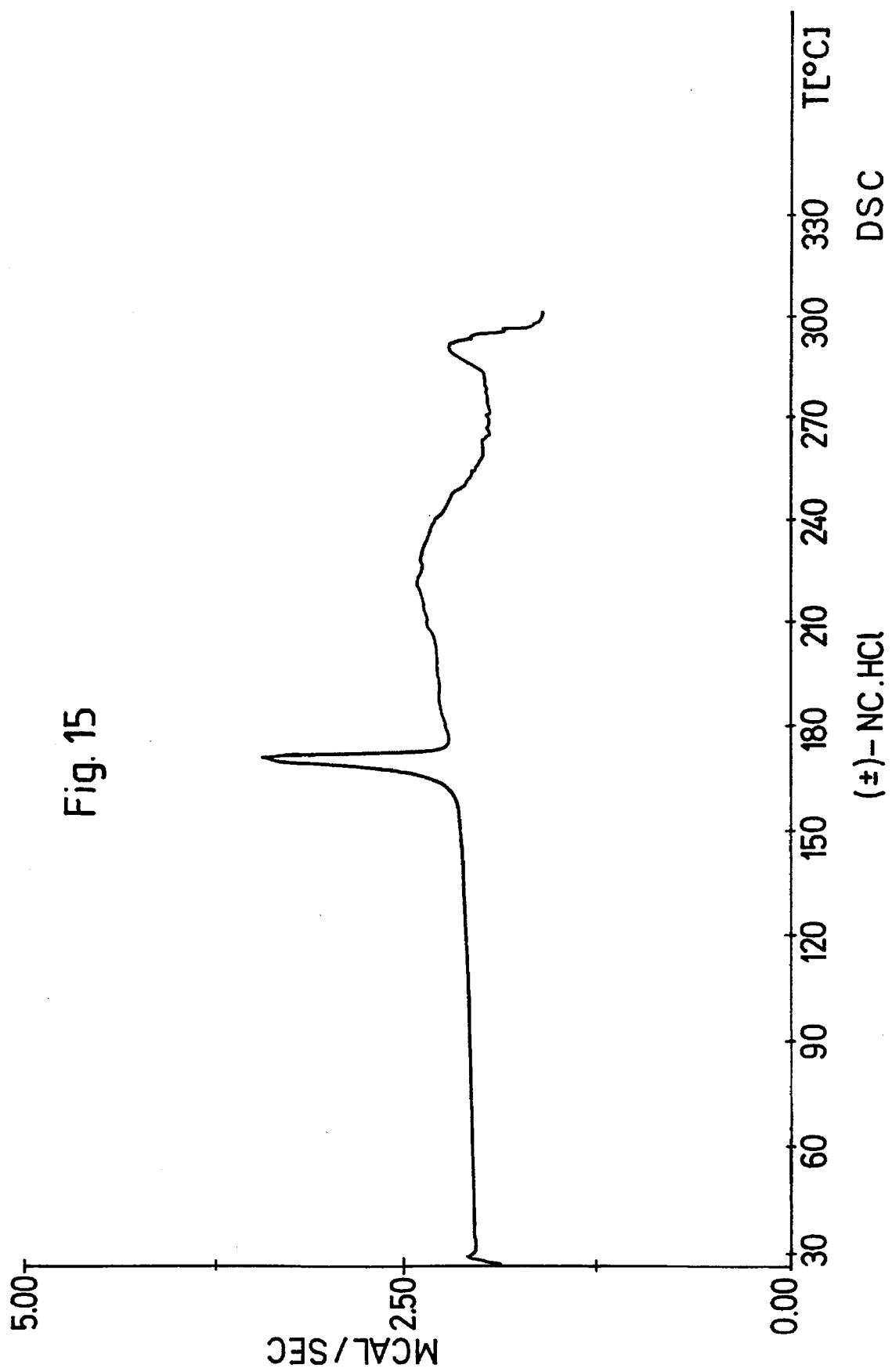
Figure 16:
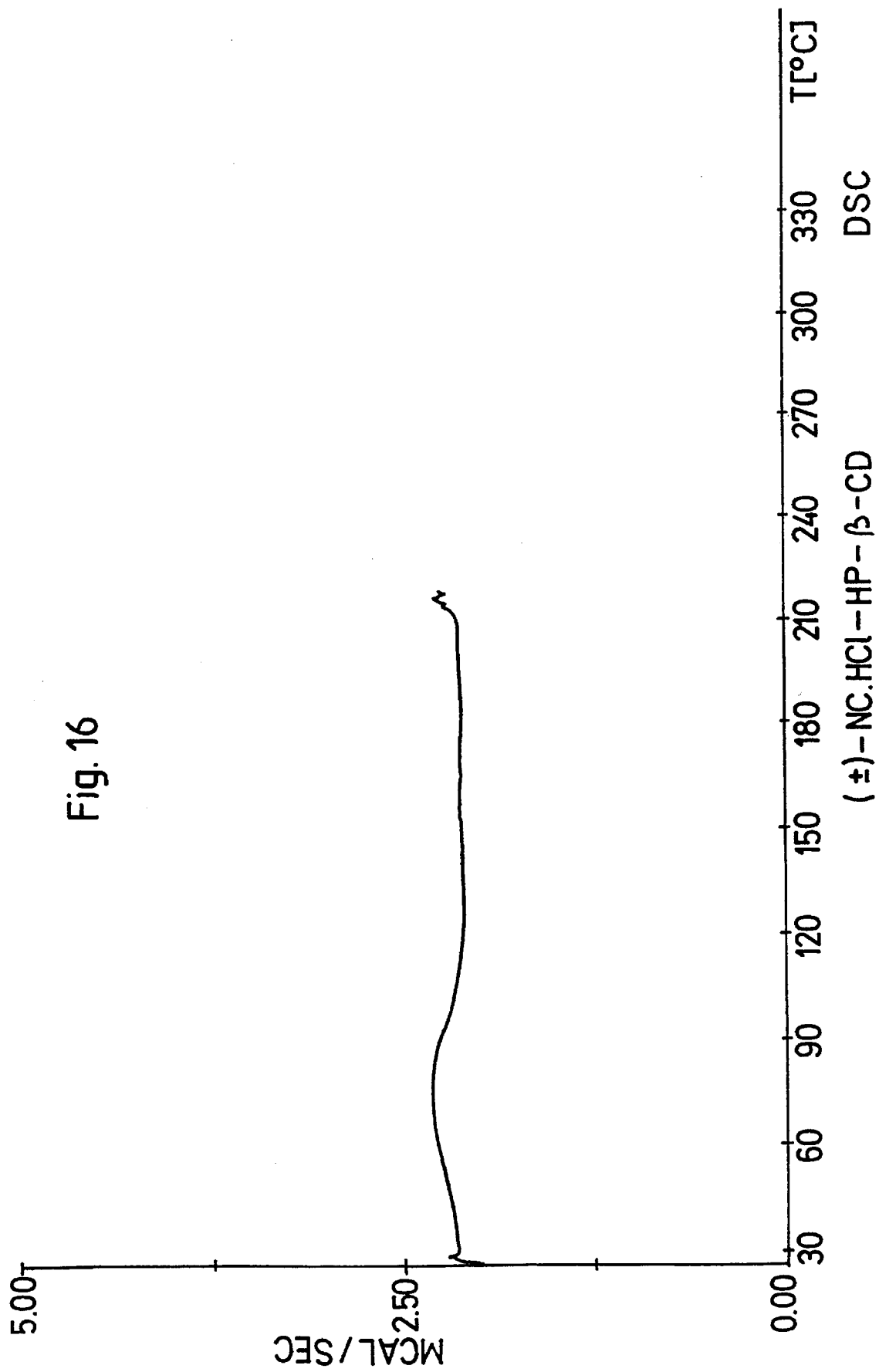
Figure 17:
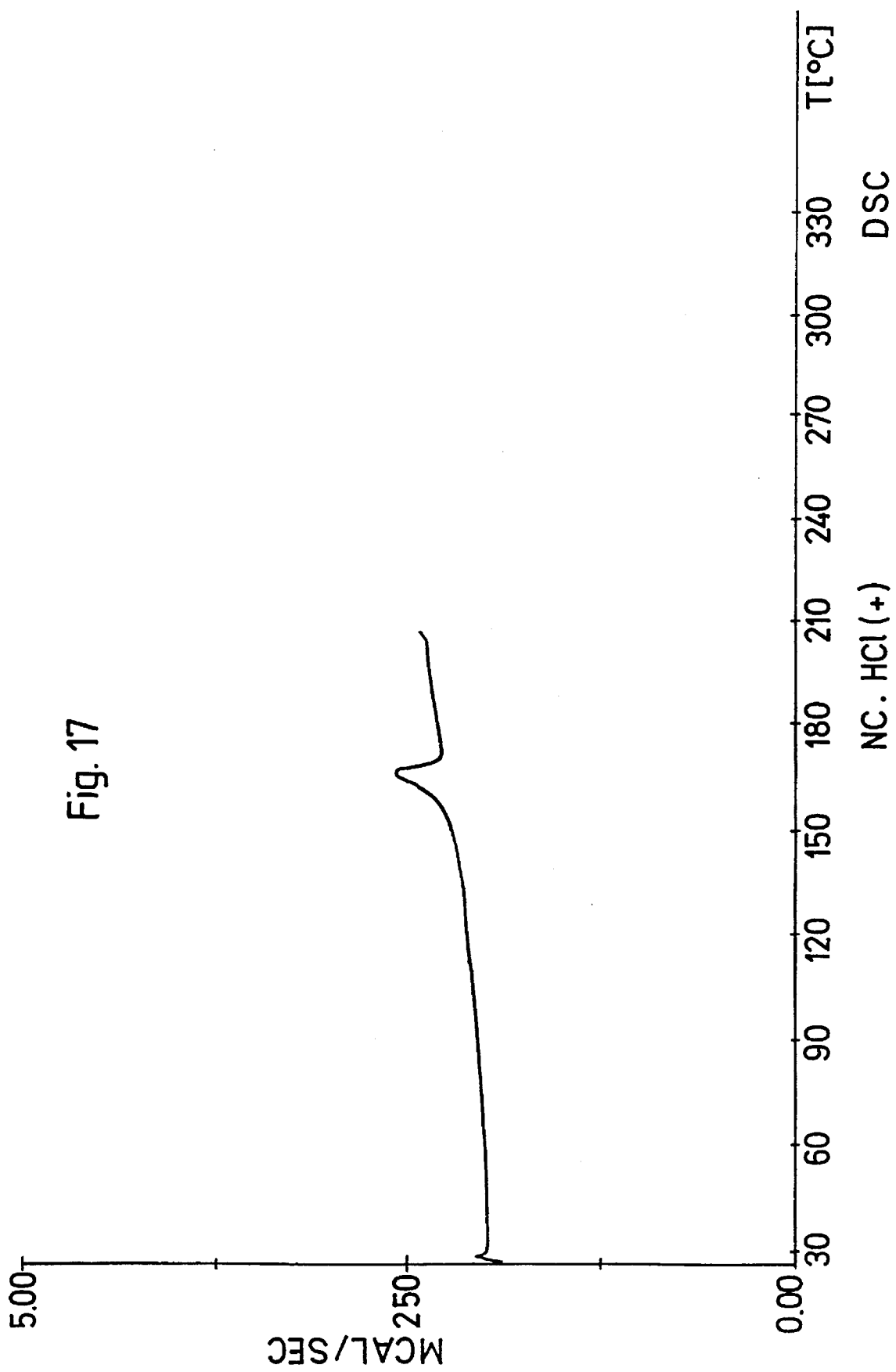
Figure 18:
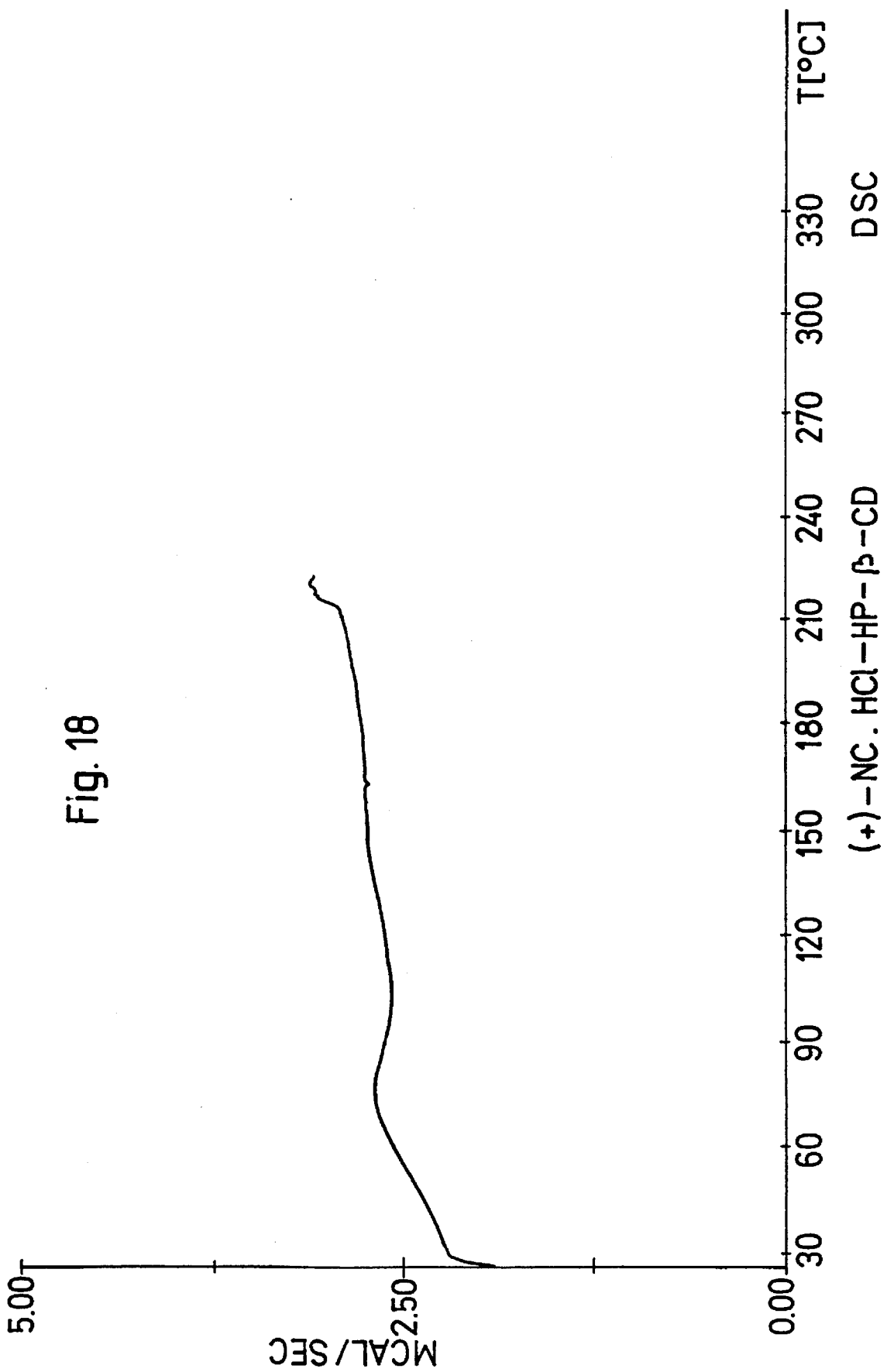
Figure 19:
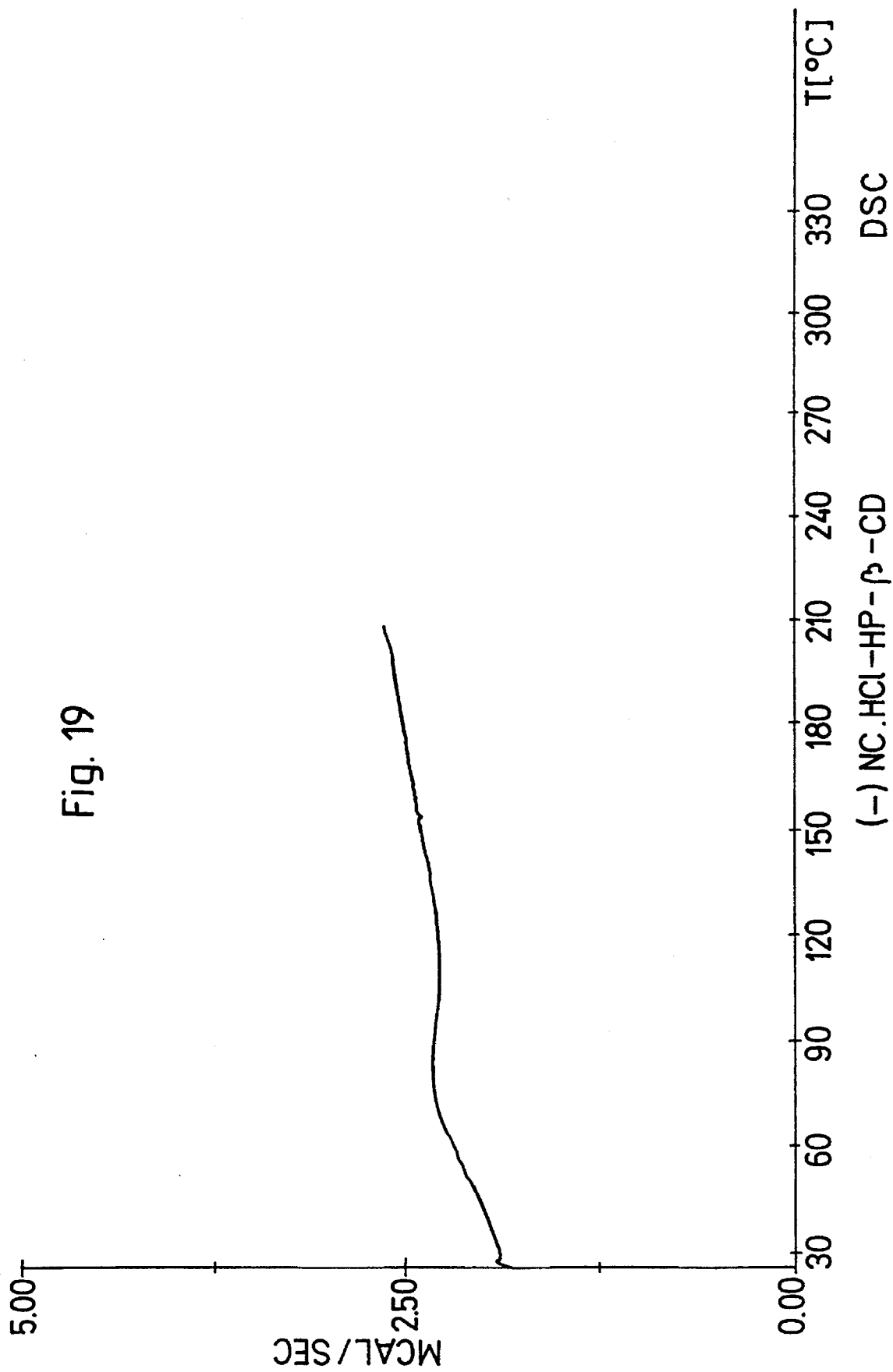
Figure 20:
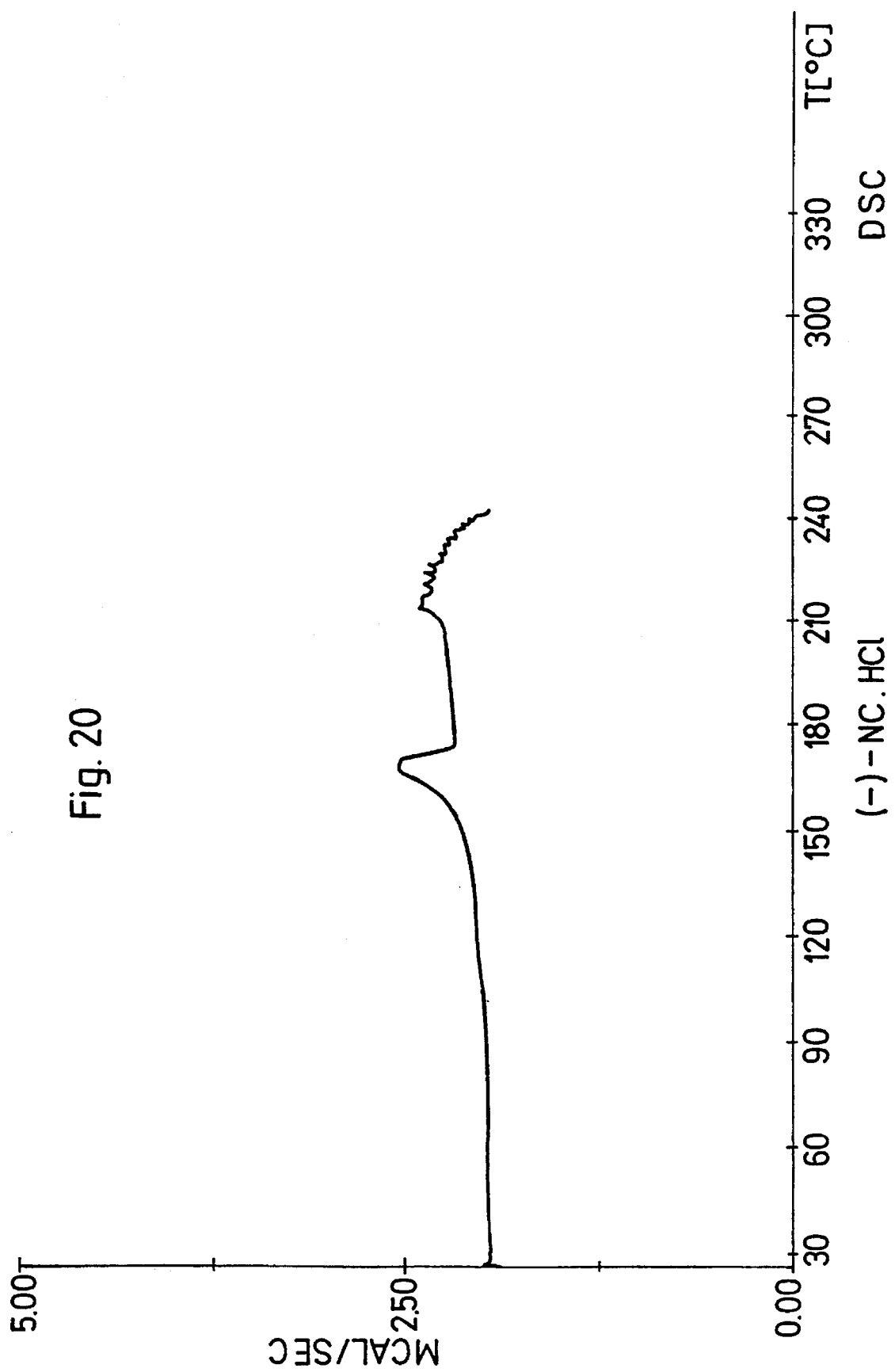
Figure 21:
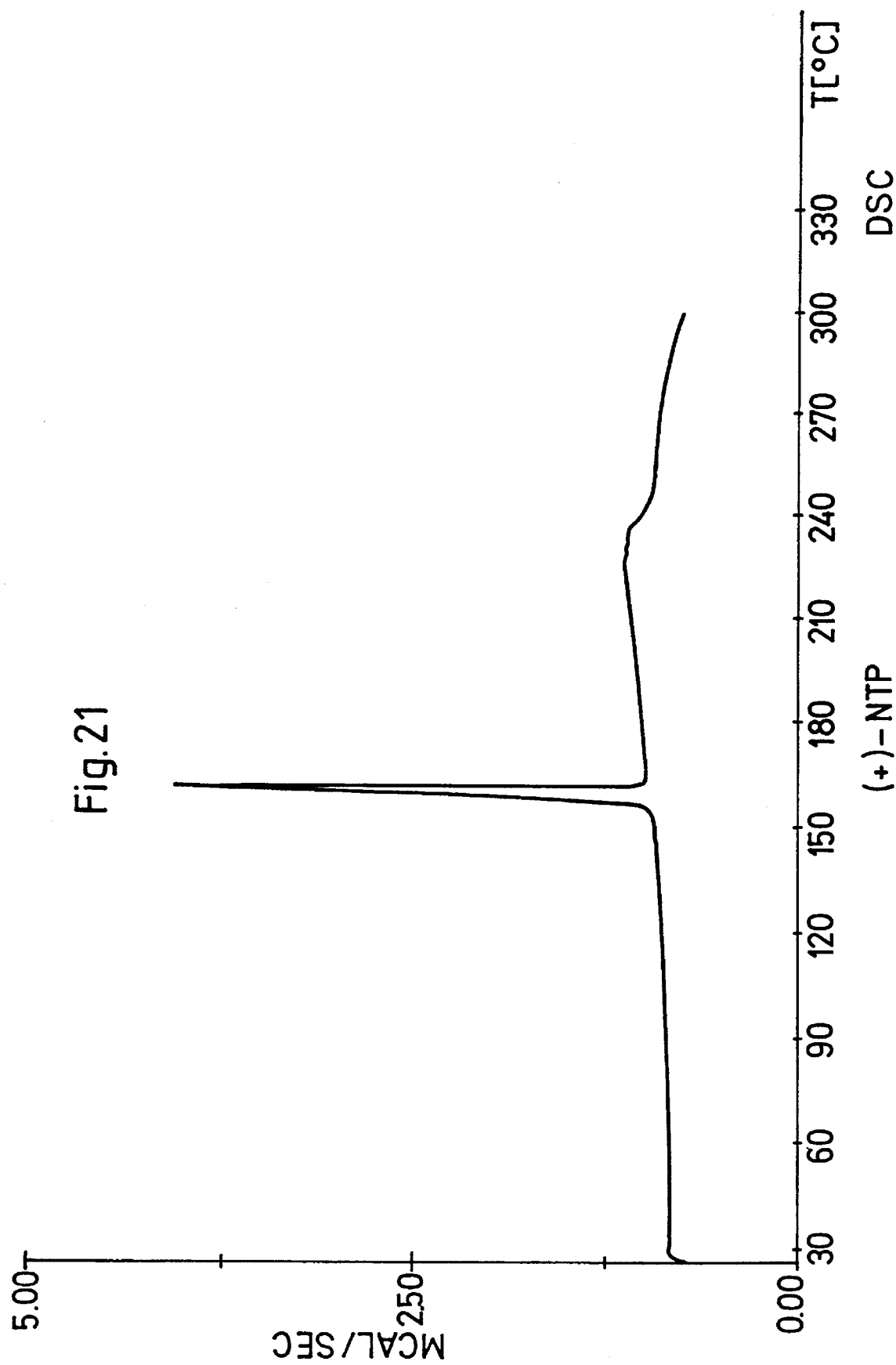
Figure 22:
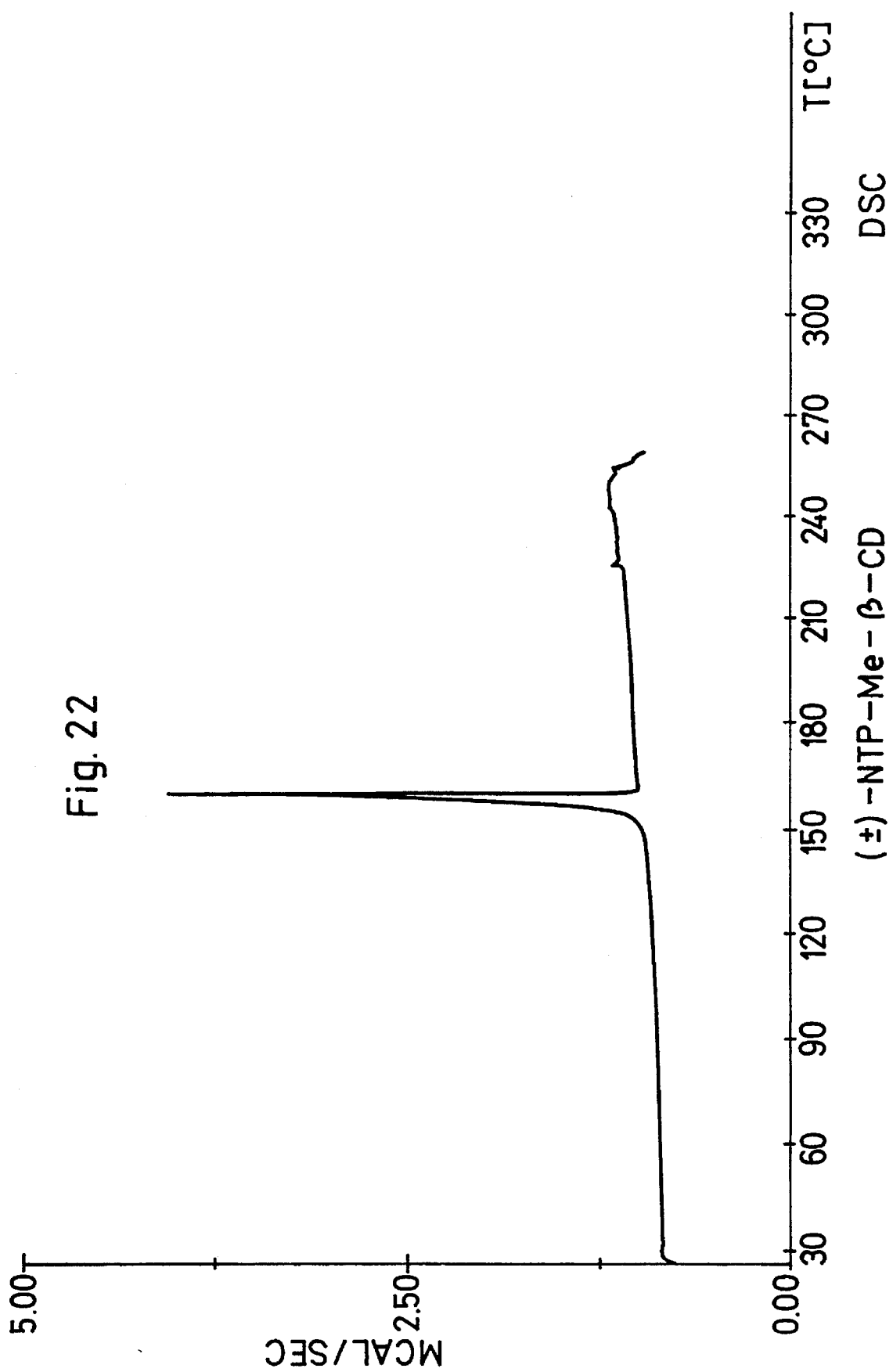
Figure 23:
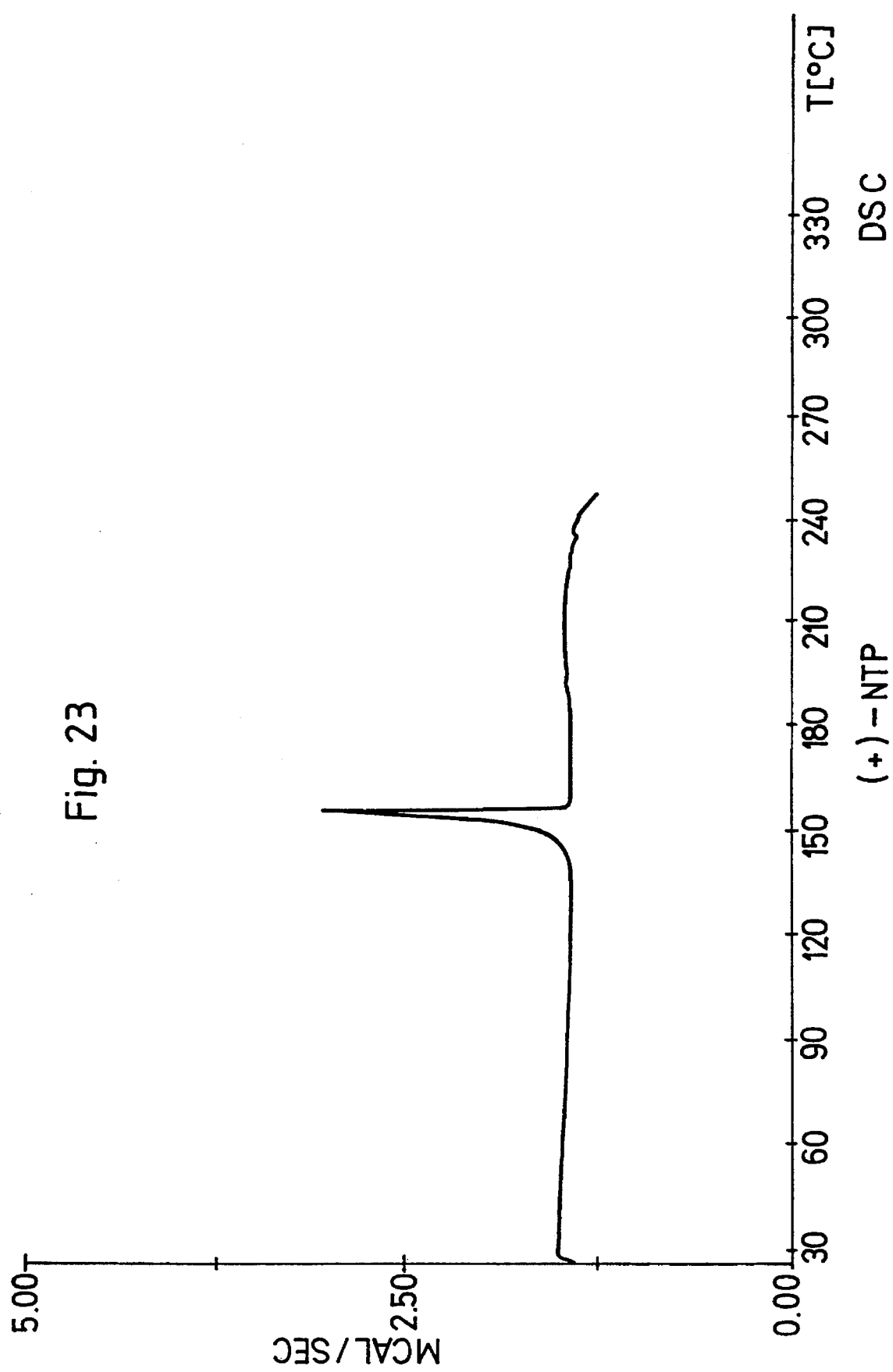
Figure 24:
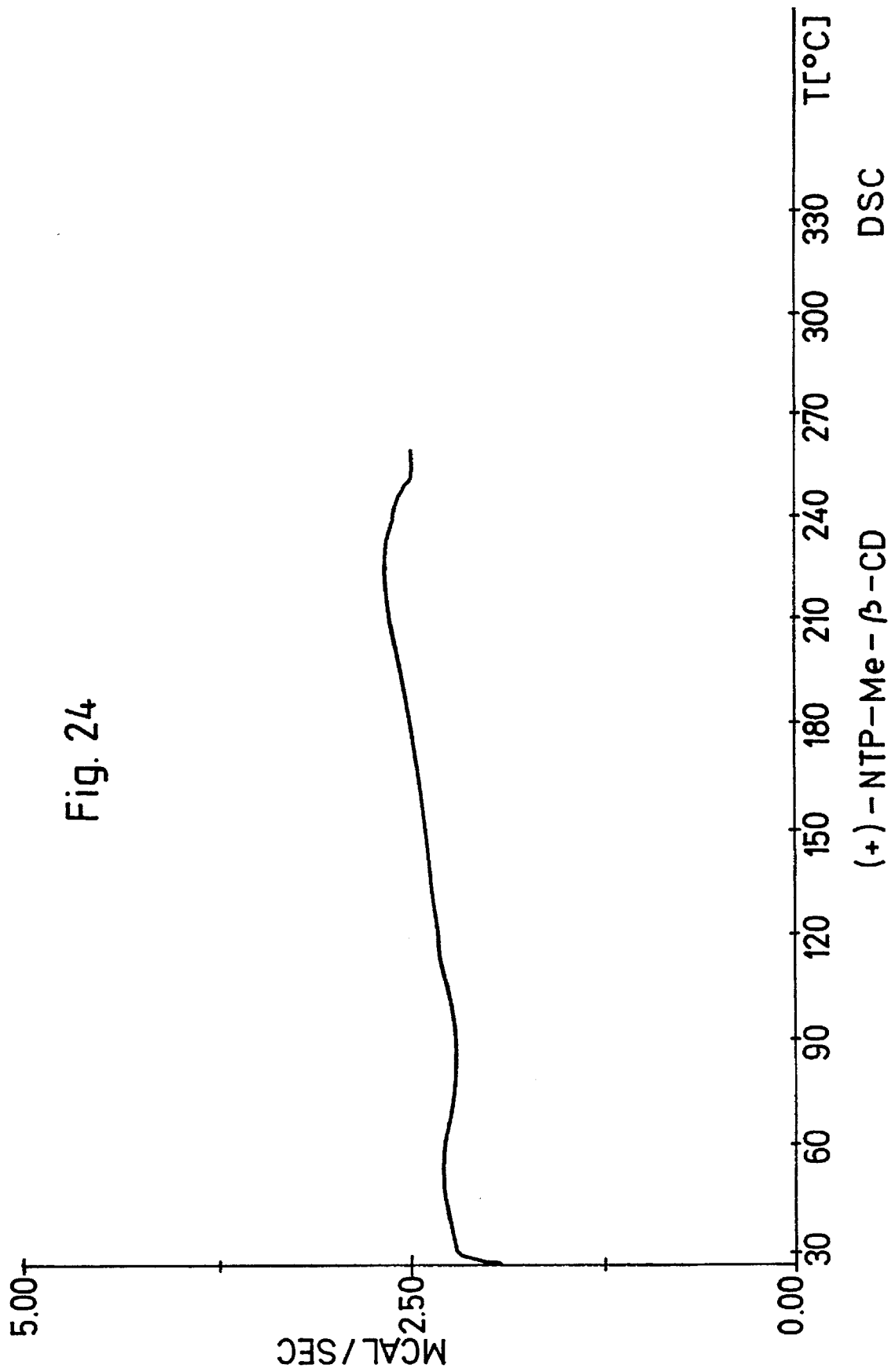
Figure 25:
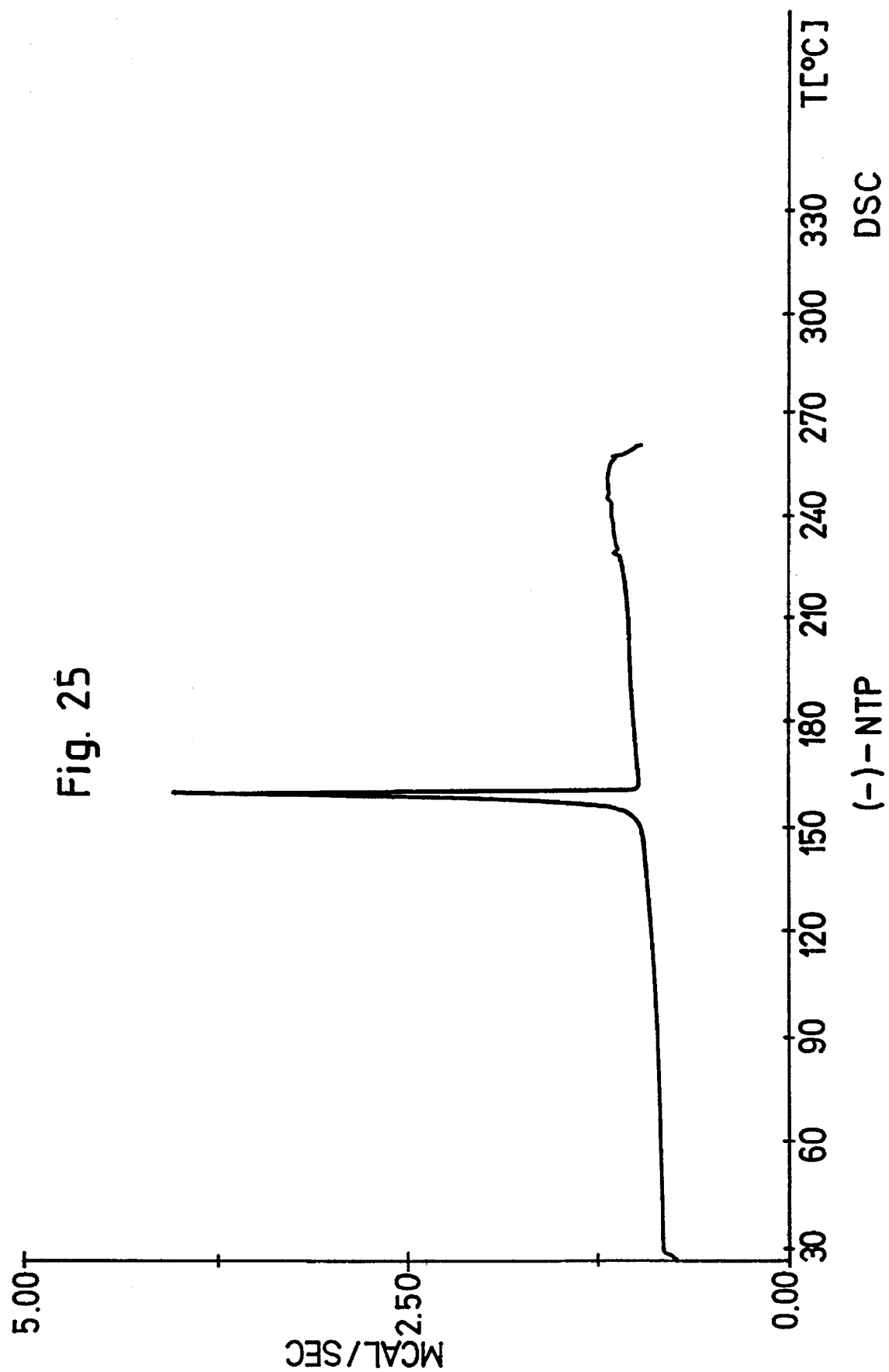
Figure 26:
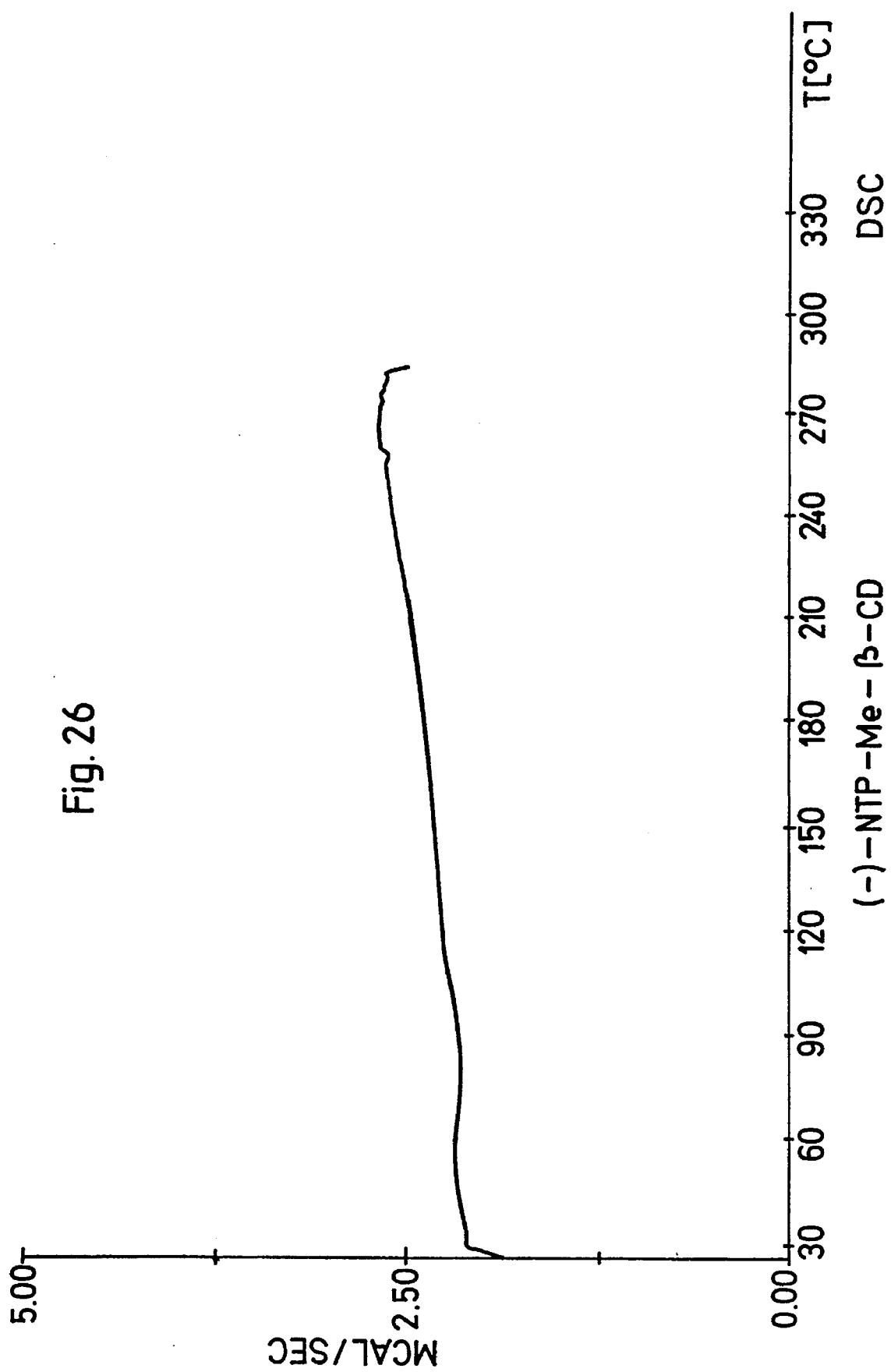
Figure 27:
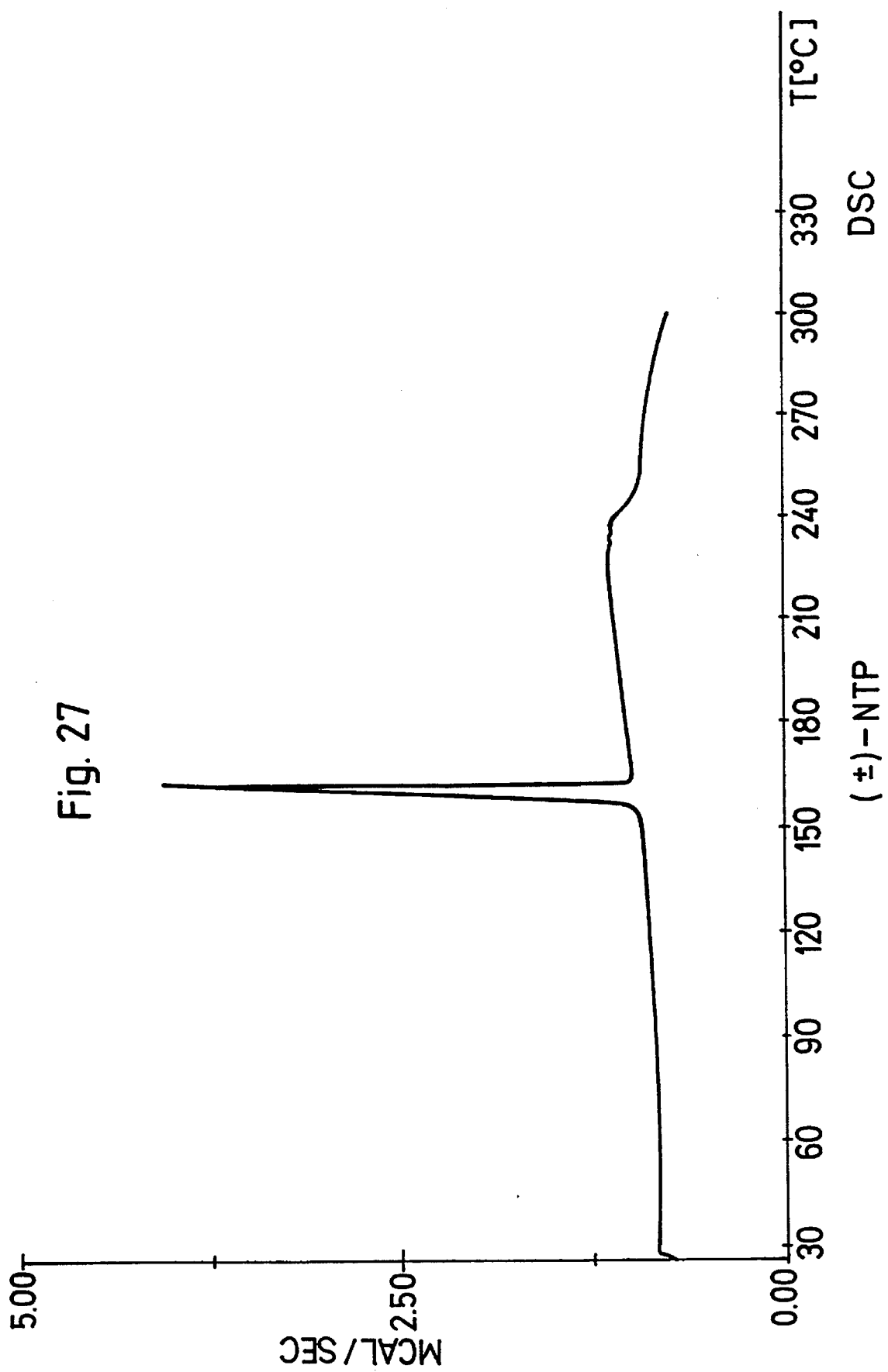
Figure 28:
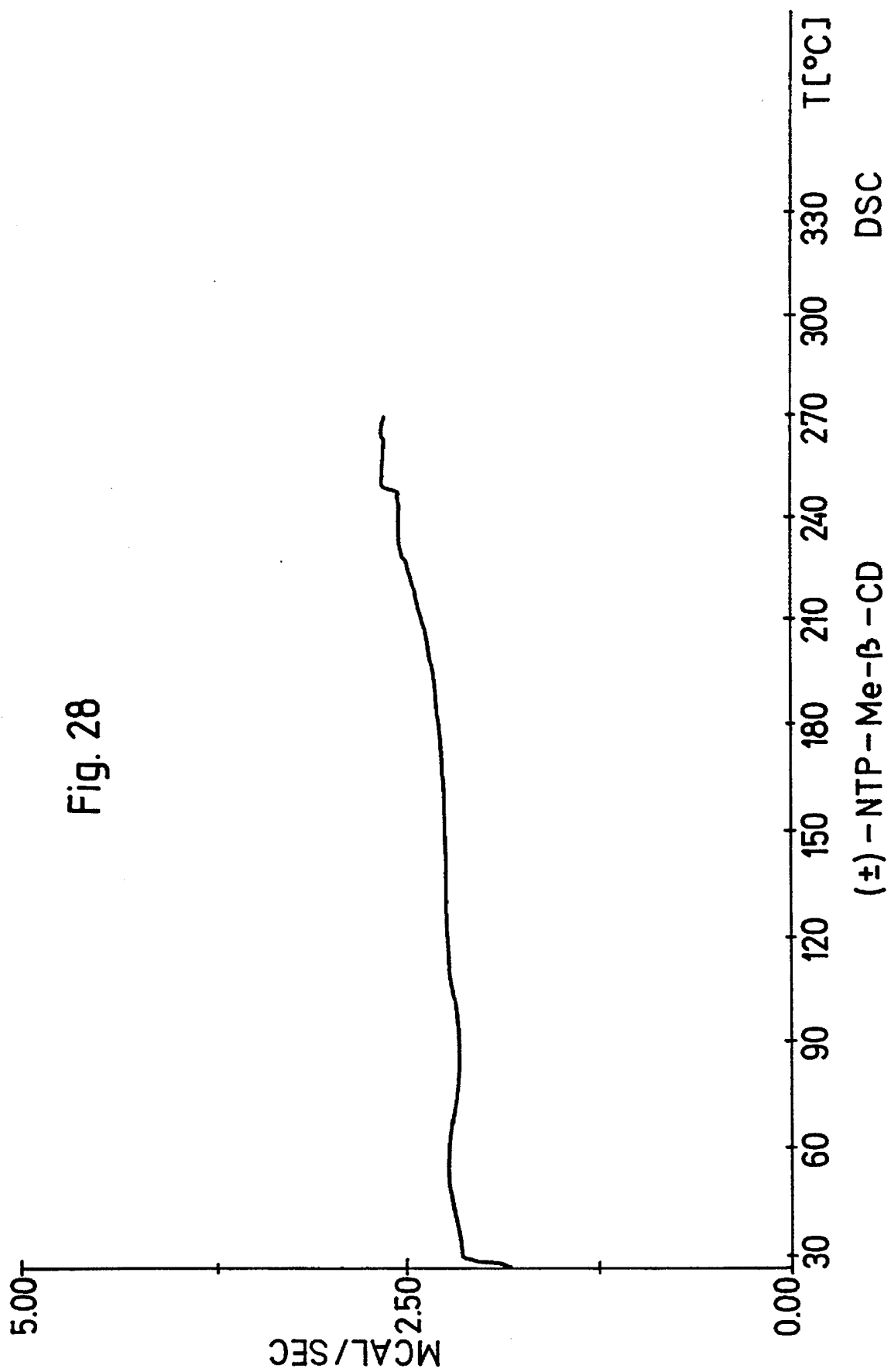
Figure 29:
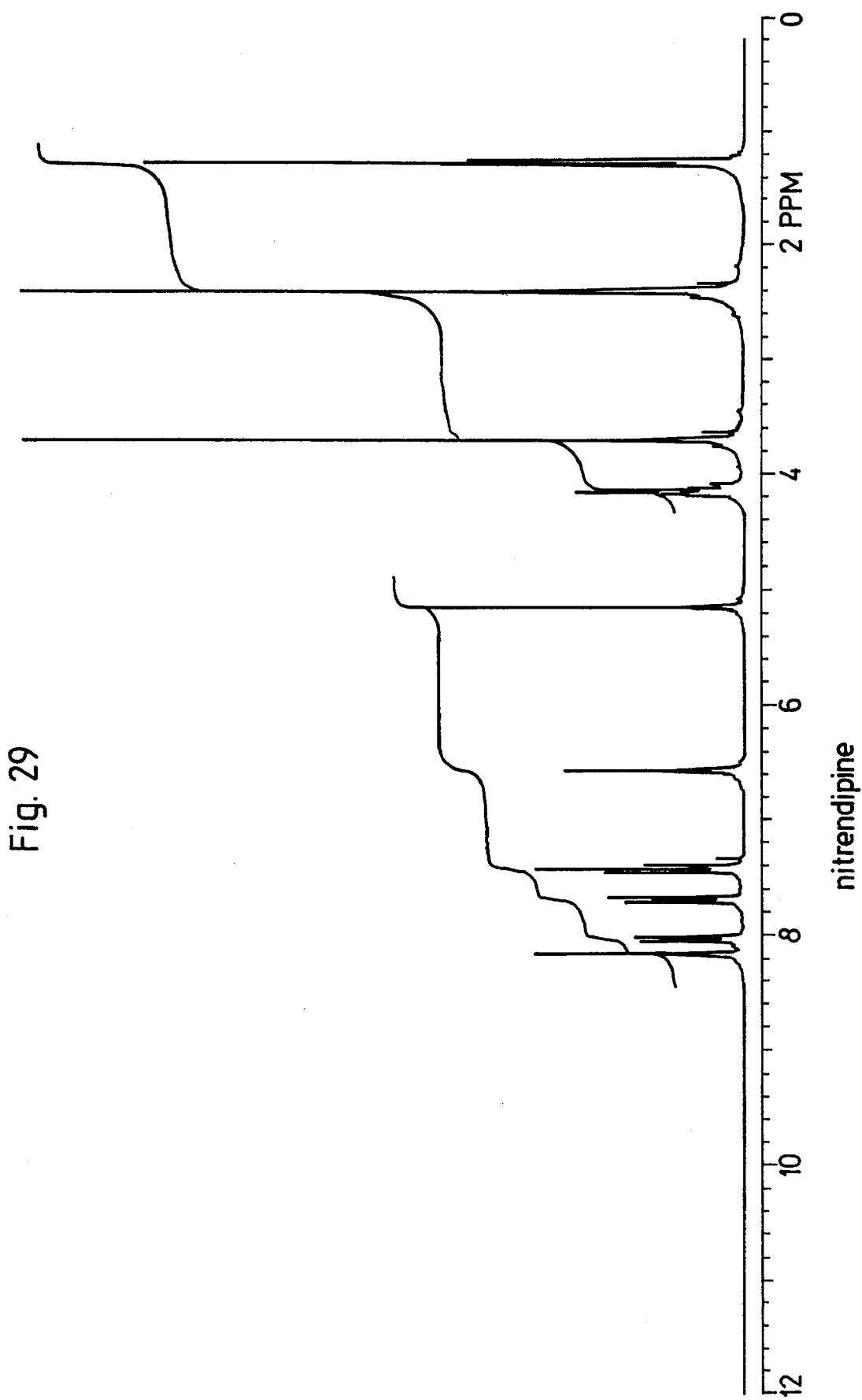
FIGS. 29 to 36 show NMR spectra of inclusion complexes of enantiomers and racemates of nitredipine and nicardipine hydrochloride with Me-β-CD and HP-β-CD, respectively, as well as of the free active substance (enantiomers and racemate).
Figure 30:
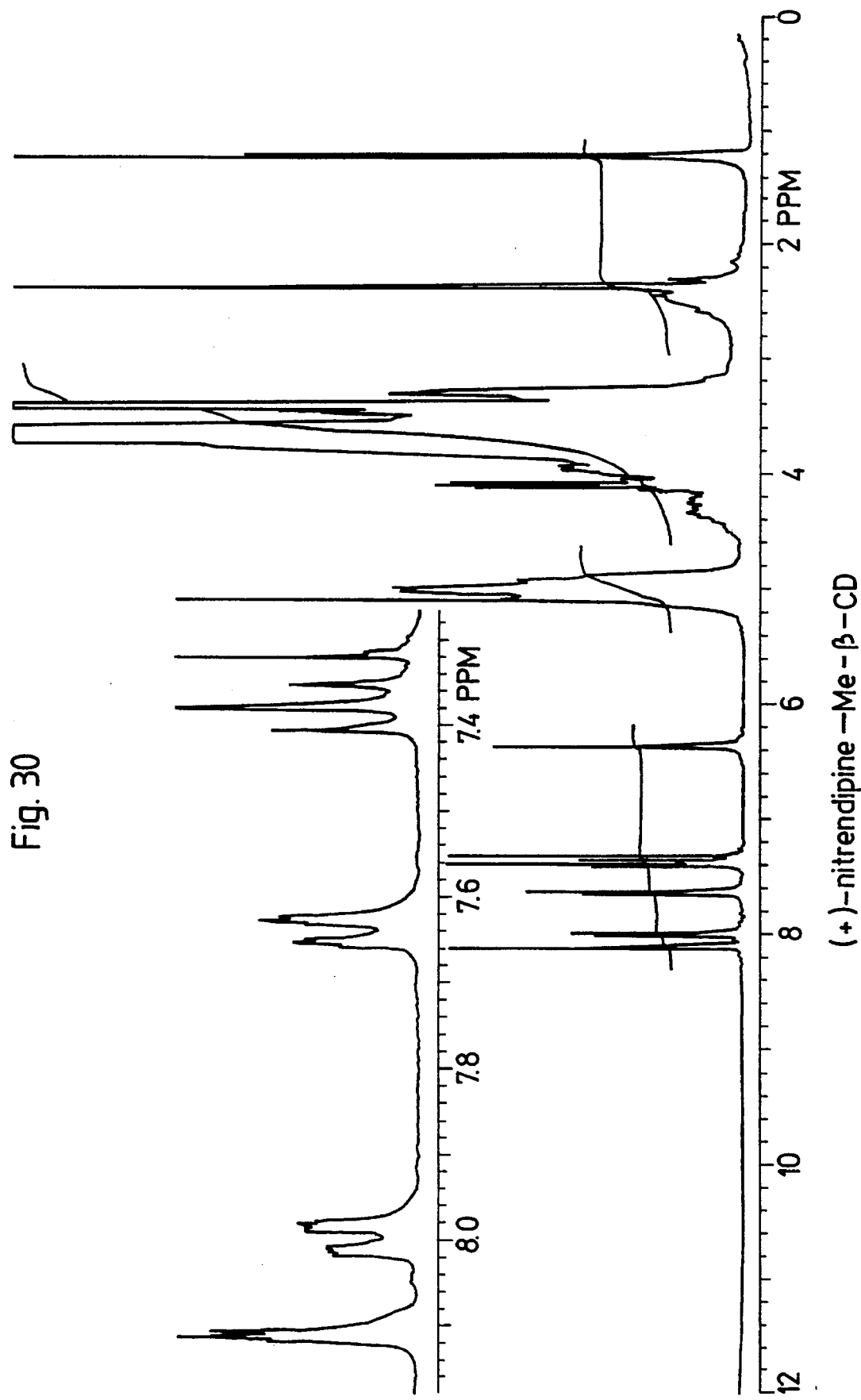
Figure 31:
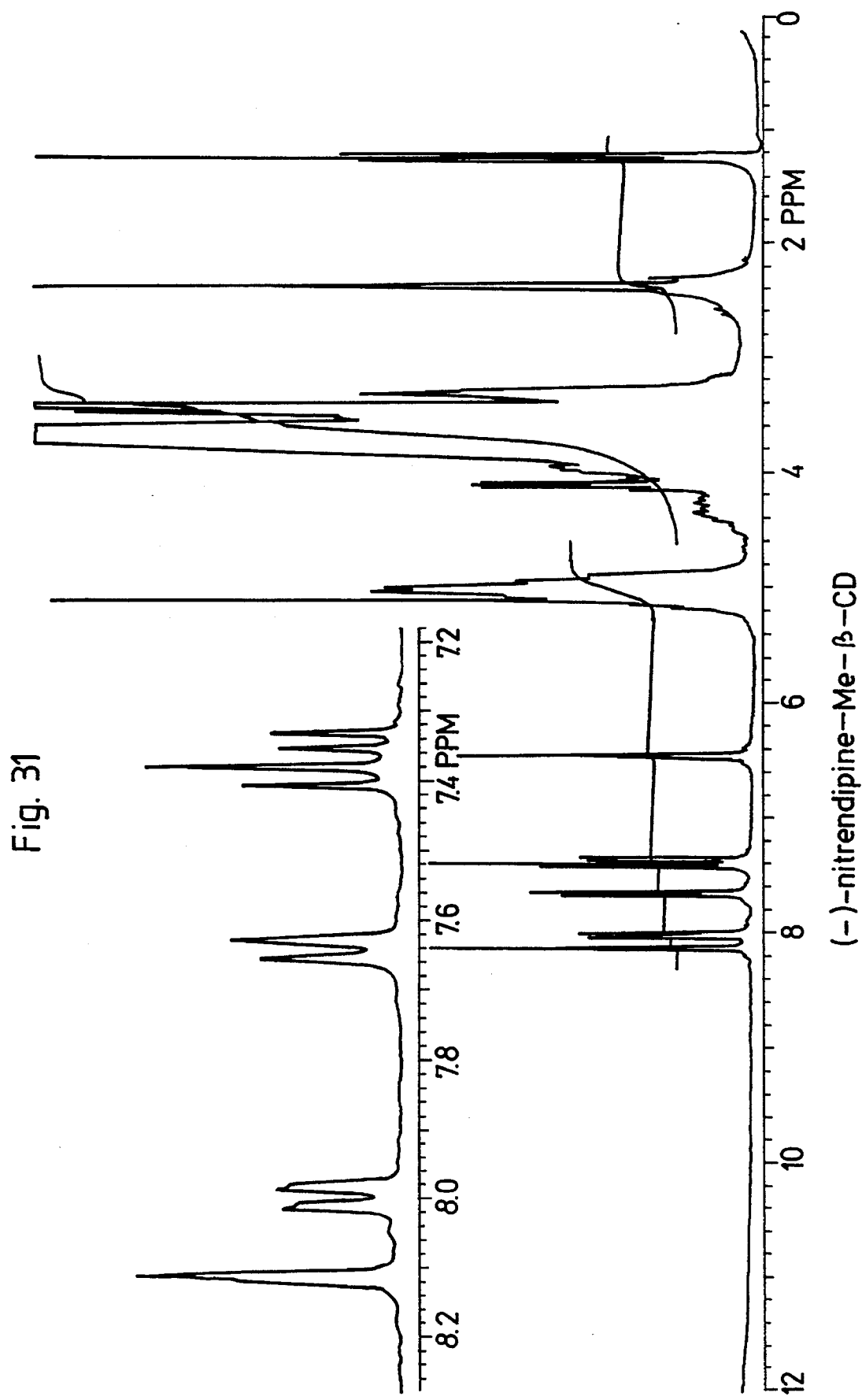
Figure 32:
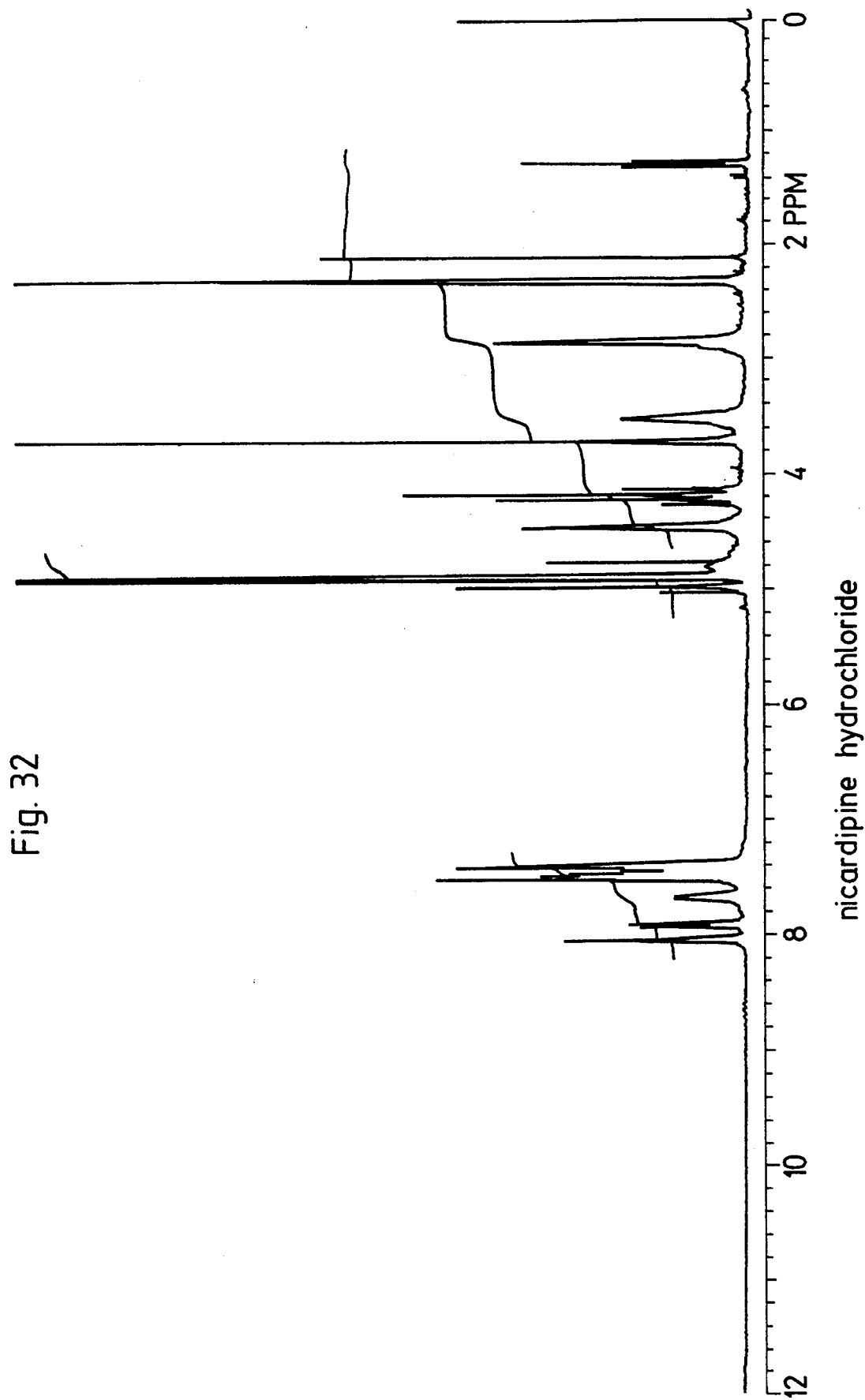
Figure 33:
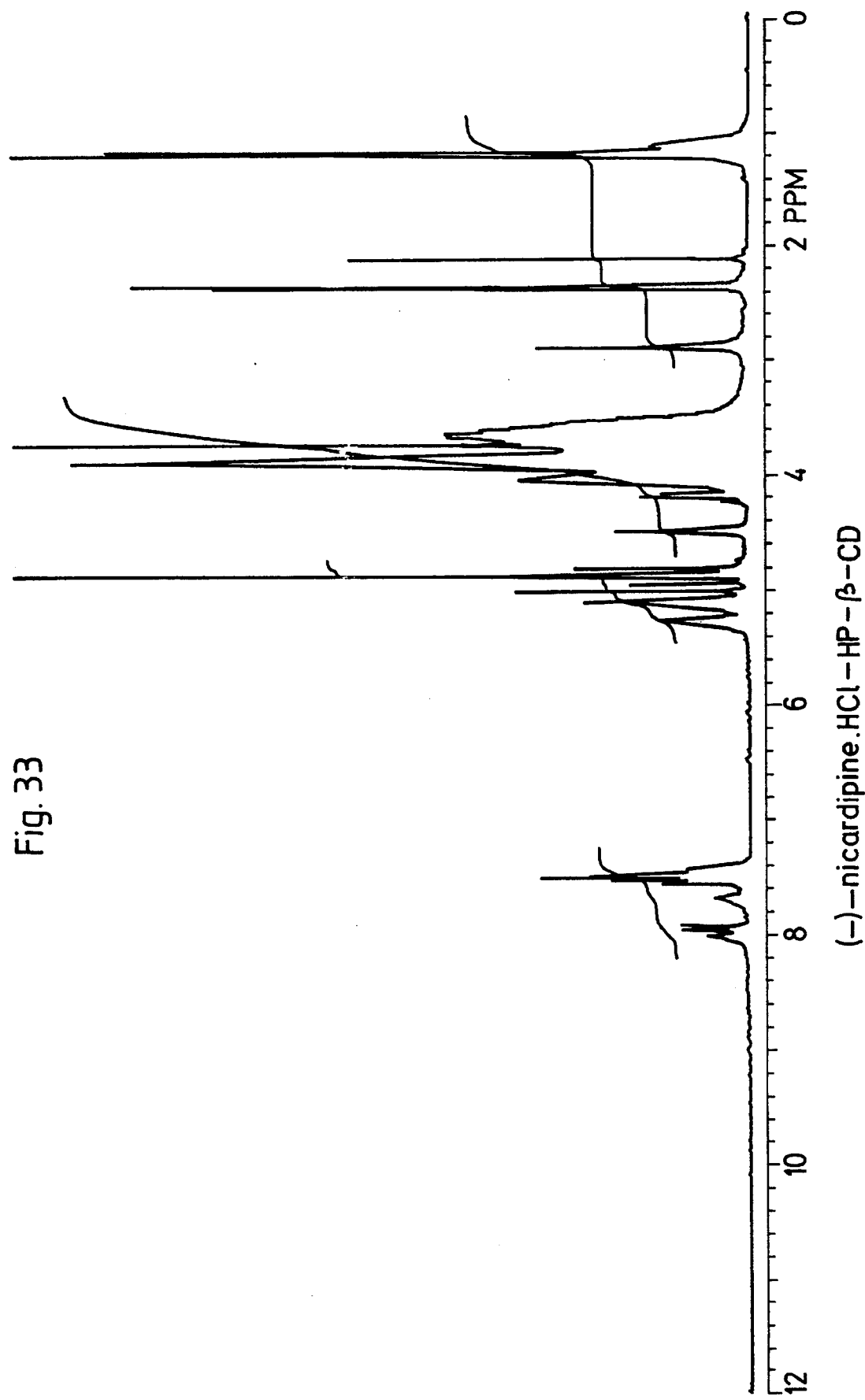
Figure 34:
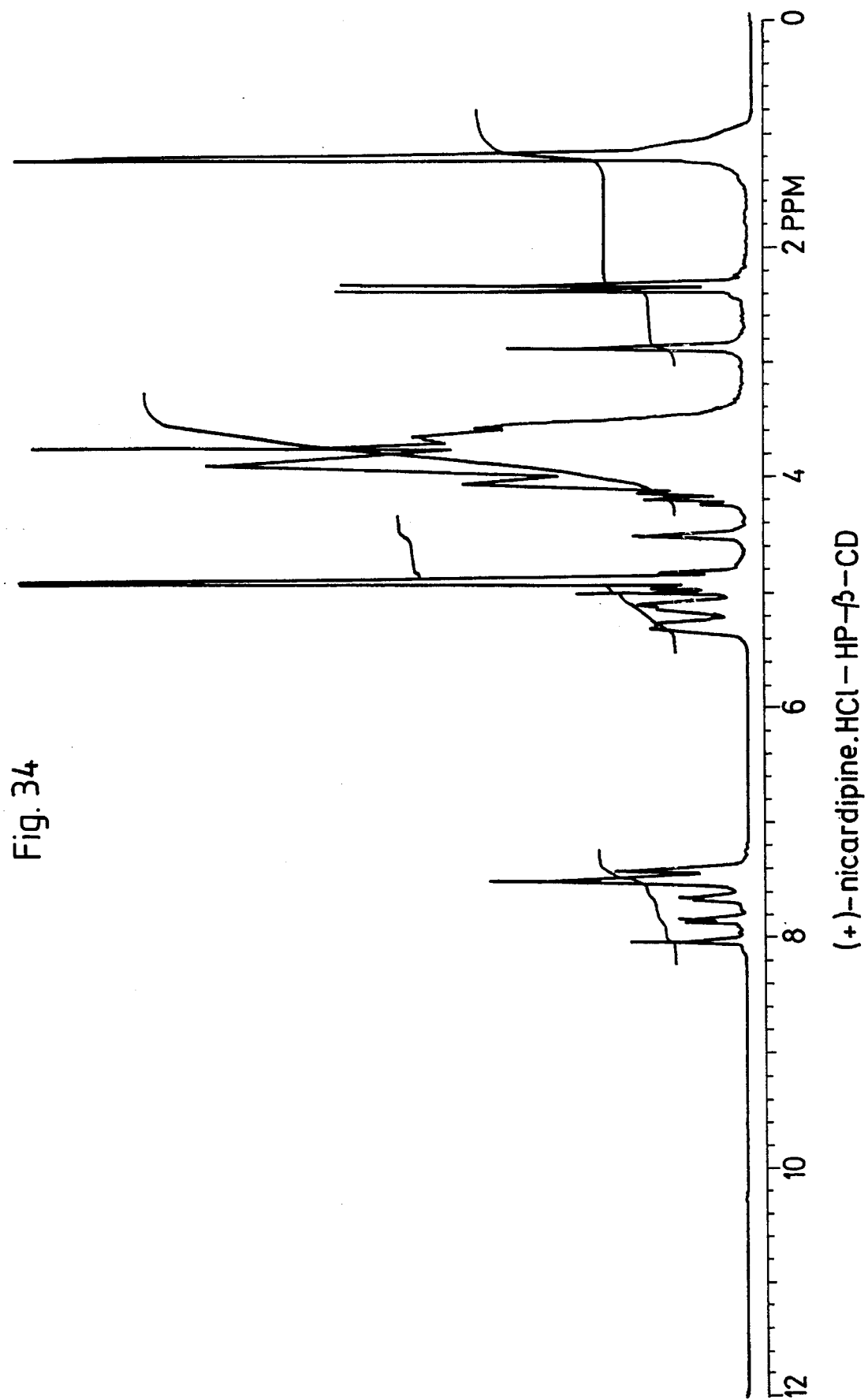
Figure 35:
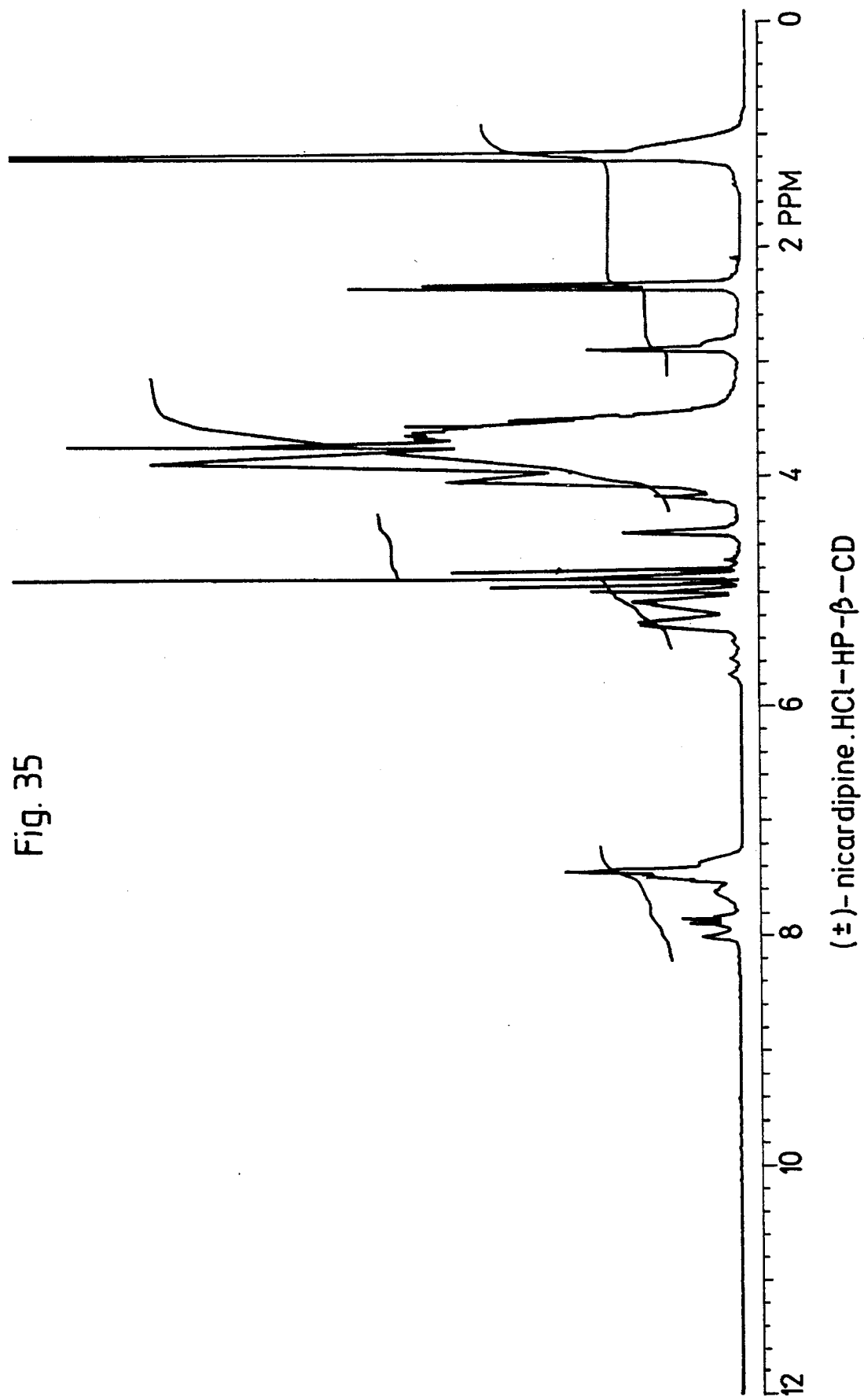
Figure 36:
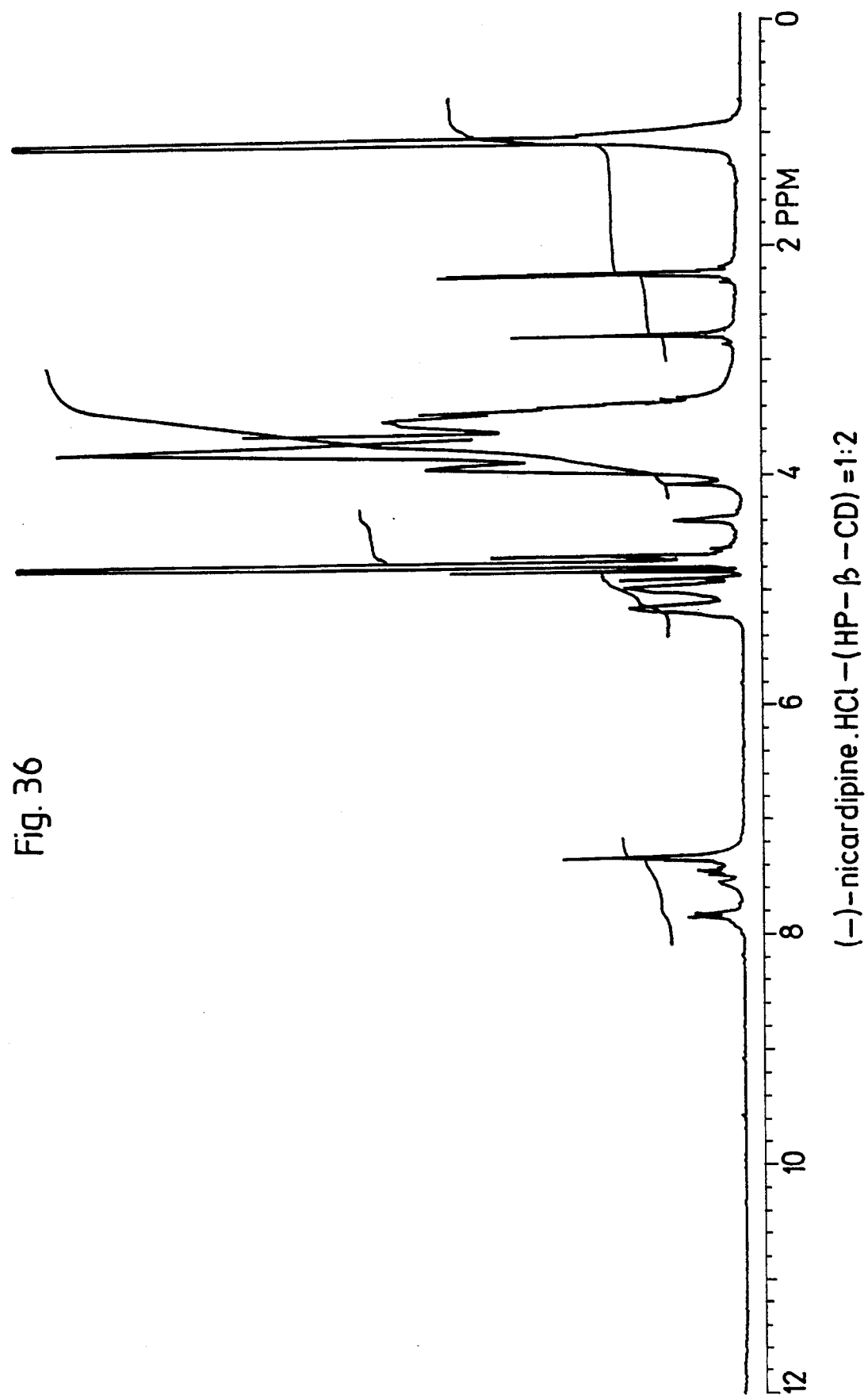

In the $^1$H-NMR specter of the desired product (FIG. 11a and FIG. 11b) in $D_2O$ solution, the following changes were observed:

in amlodipine moiety: the signals for resonances of hydrogens in the chlorophenyl part of the ring were shifted:

7.4–7.34 ppm shift of doublet for o—H for 0.09 ppm,
7.29–7.23 ppm shift of doublet for o'—H for 0.11 ppm,
7.21–7.13 ppm shift of doublet-doublet for p—H for 0.11 ppm,
7.13–7.05 ppm shift of doublet-doublet for p'—H for 0.1 ppm;

in cyclodextrin part: signals for $C_3$—H were shifted to a higher field at 3.85–3.75 ppm.

FIG. 12a and 12b illustrate the spectra of amlodipine besylate.

EXAMPLE 7

Preparation of inclusion complex of amlodipine besylate (AML.S) with 2-hydroxypropyl-β-cyclodextrin (2-HP-β-CD)

Amlodipine besylate (0.63 g; 1.11 mmole) was suspended in distilled water (50 ml) and to the suspension hydroxypropyl-β-cyclodextrin (1.57 g; 1.13 mmole) was added under stirring. The reaction mixture was heated up to 70° C. and then stirred for 1 hour at this temperature. The almost clear solution was slowly cooled down to room temperature without stirring, filtered and the filtrate was evaporated to a dry product in vacuo at 50° C. A white microcrystalline desired product (2.06 g; 93.6%) with m.p. 170°–180° C. (dec.) was obtained.

EXAMPLE 8

Preparation of inclusion complex of (+) nicardipine hydrochloride with β-cyclodextrin and of (+) nicardipine hydrochloride by enantioseparation of the racemic nicardipine hydrochloride by means of a preparative column chromatography For preparing both desired substances the following chromatographic system and elution conditions were employed:
SP: 600 g β-CD, swollen in water, atmospheric pressure
MP: saturated aqueous solution of β-CD
PR: racemic nicardipine hydrochloride (4 g) in a physical mixture with a 5-fold amount of β-CD
Weight ratio SP:PR=150:1
Composition of eluates:

The eluates were aqueous suspensions of the inclusion complex of nicardipine hydrochloride with β-CD with an excess of β-CD. The composition of the eluates was established by means of HPLC, $^1$H-NMR and DSC methods (the content of (+) nicardipine hydrochloride in dry substance of the eluates was 7 to 20%, determined by HPLC).

A) Isolation of the inclusion complex of (+) nicardipine hydrochloride with β-CD [(+)—NC.HCl-β-CD]

Combined eluates (700 ml), which were found by means of HPLC analysis (detection according to the principle of circular dichroism) to contain the inclusion complex of (+) nicardipine hydrochloride with β-CD, were lyophilized. 10 g of the dry substance obtained were suspended in water (50 ml), stirred at room temperature for 3 hours and then cooled overnight at the temperature of 4° C. The precipitate obtained was filtered and the solution was lyophilized. The inclusion complex (4.2 g) of (+) nicardipine hydrochloride with β-CD in the form of a yellow microcrystalline product in a molar ratio of 1:1 was obtained.

Analysis:

The inclusion complex contained 30.5% of (+) nicardipine hydrochloride (31.2% of theory) as determined with HPLC.

$^1$H-NMR: Characteristic shifts for inclusion of nicardipine hydrochloride in β-CD were noticeable.

DSC: No traces of free (+) nicardipine hydrochloride were noticeable.

Optical rotation:
(+)-NC.HCl-β-CD: $[α]_D^{22}$ (CH$_3$OH, 0.5)=+137.6°
(+)-NC.HCl: $[α]_D^{22}$ (CH$_3$OH,0.5)=+72.3°
β-CD: $[α]_D^{22}$ (H$_2$O, 0.5)=+149.4°

B) Isolation of (+) nicardipine hydrochloride

Combined eluates (700 ml), which were found by means of HPLC analysis (detection according to the principle of circular dichroism) to contain (+) nicardipine hydrochloride, were lyophilized. 10 g of the dry substance obtained were suspended in methanol (50 ml), whereby a major part of β-CD precipitated, which was filtered and washed on the filter with methanol (3×5 ml). The mother liquor (50 ml) and washing solution (15 ml) were combined, the combined solution was evaporated to a dry residue at the temperature of 40° C. and at the reduced pressure of 24 mbar and then dried in vacuo to a constant weight (1.4 g).

The dry product obtained was suspended in methylene chloride (75 ml) and thereby the still residual amount of β-CD precipitated from the sample. The precipitate obtained was filtered, the filtrate was evaporated to dryness at reduced pressure and at the temperature of 60° C. and then dried to a constant weight (1.3 g) in vacuo. The raw product was recrystallized from ethylacetate (6 ml) under stirring for 2 hours at room temperature and thus a light yellow crystalline product (1.1 g) precipitated from the solution. It was dissolved in methanol (5 ml) at room temperature, the solution obtained was heated to a temperature of 40° C., the solution was cooled and filtered. The clear filtrate was evaporated to a glassy amorphous residue (1 g)/n vacuo at the temperature of 50° C., which was again dissolved in acetone (5 ml) at the temperature of 0° C. After an hour a light yellow crystalline precipitate was obtained. The reaction mixture was stirred for another hour at the temperature of 0° C. The precipitate was filtered, washed with acetone (3×1.5 ml) and the moist product was dried in vacuo at 80° C. The desired compound (0.7 g) was obtained in the form of a yellow crystalline product with m.p. 175°–176° C.

Analysis:
$[α]_D^{22}$ (CH$_3$OH, 0.5)=+72.3°
HPLC: purity 96 area %

The structure of (+) NC.HCl was confirmed by $^1$H-NMR specter.

EXAMPLE 9

Preparation of racemic and enantiomerically pure inclusion complexes of nicardipine hydrochloride with HP-β-CD It was proceeded as illustrated in the Table IV and as disclosed in Example 13, resp.

In the Table II there are given analytical parameters characterizing the structures of enantiomeric and racemic inclusion complexes of nicardipine hydrochloride with HP-β-CD as well as the free active substance (enantiomers and racemate).

EXAMPLE 10

Enantioseparation of the racemic amlodipine maleate by means of preparative column chromatography and isolation of (−) amlodipine maleate enantiomer The following chromatographic system and eluting conditions were used:

SP: dry β-CD (500 g), chromatographic column for operating at reduced pressure ("dry flash");
MP: saturated aqueous solution of 2-HP-β-CD
PR: racemic inclusion complex (5 g) of amlodipine maleate with β-CD [AML.M-β-CD]
Weight ratio of SP:PR=100:1

Treatment of eluates and isolation of (−) enantiomer of amlodipine maleate

The combined eluates (55 ml) containing an aqueous solution of the inclusion complex of (−) amlodipine maleate with β-cyclodextrin (abb. AML.M-β-CD) and of (−) amlodipine maleate with 2-hydroxypropyl-β-cyclodextrin (abb. AML.M-HP-β-CD) with an excess of cyclodextrins (the composition was determined by means of HPLC, $^1$H-NMR and DSC analyses), were lyophilized to a dry residue. The dry substance obtained (7 g) was pulverized and, under vigorous stirring, slowly suspended in an aqueous sodium hydroxide solution (20 ml; conc.=0.1 mole/l). The precipitate obtained (0.9 g) was filtered and abundantly washed on the filter with a fresh aqueous sodium hydroxide solution (2×5 ml). The precipitate (0.9 g) was dissolved in ethyl acetate (10 ml) and the solution was washed with water (3×10 ml). The obtained ethyl acetate extract was dried with Na$_2$SO$_4$ and than evaporated to a dry residue at a temperature of 40° C. and reduced pressure (23 mbar). The dry product (0.7 g) was then dissolved in methanol (20 ml) and maleic acid (0.2 g) was added. The reaction mixture was heated at the reflux temperature for 15 minutes, the solvent was evaporated at reduced pressure and the product obtained was dried to a constant weight (0.85 g) in vacuo at the temperature of 40° C. The raw product was recrystallized from a hot ethanolic solution saturated with cinchonidine and then also from isopropanol/diisopropylether mixture (4 ml). The desired product was obtained in the form of a beige coloured crystalline product with m.p. 156°–158° C.

Analysis (−)-AML.M:
$[α]_D^{22}$ (CH$_3$OH, 0.5)=−26.1°
purity (HPLC): 98 area %

$^1$H-NMR: The structure of (−) amlodipine maleate was confirmed by specter.

EXAMPLE 11

Enantioseparation of racemic nitrendipine by means of preparative column chromatography and isolation of inclusion complex of (−) nitrendipine with methyl-β-cyclodextrin [abb.(−)-NTP-Me-β-CD]

The following chromatographic system and eluting conditions were used:

SP: 220 g of racemic nitrendipine, vaporized on silicagel in vacuo, weight ratio silicagel/racemic nitrendipine=10:1;
MP: ratio CH$_3$OH:H$_2$O=2:5 with a negative concentration gradient for Me-β-CD
0.05M/l to 0.01M/l;
PR: racemic nitrendipine on silicagel.

The composition of eluates

The eluates were methanolic aqueous solutions of inclusion complexes of NTP-Me-β-CD with the admixtures of Me-β-CD. The content of (−) nitrendipine in the dry substance of the eluates was 12 to 19% determined with HPLC. In $^1$H-NMR specter characteristic shifts for chiral C—H group were noticeable in nitrendipine specter due to the inclusion into a ring of Me-β-CD.DSC showed no traces of free nitrendipine.

Treatment of eluates

The combined eluates (260 ml) were evaporated at reduced pressure at 70° C. and the residue was dried to a constant weight (14 g) in vacuo. The dry product was suspended in water (30 ml), the suspension was stirred for 30 minutes and then filtered. The precipitate obtained was dried to a constant weight (10.3 g) in vacuo. The desired inclusion complex of (−) nitrendipine with methyl-β-cyclodextrin was obtained in the form of a yellow microcrystalline product in a molar ratio of 1:1.

Analysis:

The inclusion complex contained 21.1% of (−) nitrendipine (21.56% of theory) determined by HPLC.

$^1$H-NMR: Characteristic shifts were noticeable in the aryl moiety of nitrendipine which was included in Me-β-CD ring.

DSC: No traces of free (−) nitrendipine were noticeable.

(−)-NTP-ME-β-CD: $[\alpha]_D^{12}$ (CH$_3$OH, 0.5)=+116.0°

(−)-NTP: $[\alpha]_D^{22}$ (CH$_3$OH, 0.5)=−20.1°

Me-β-Cd: $[\alpha]_D^{22}$ (CH$_3$OH, 0.5)=+150.9°

In the Table III analytical parameters characterizing the structures of enantiomeric and racemic inclusion complexes of nitrendipine with Me-β-CD and of a free active substance (enantiomers and racemate) are given.

EXAMPLE 12

Preparation of inclusion complex of (−) nicardipine hydrochloride with 2-hydroxy-propyl-β-CD [abb.(−)-NC.HCl/2-HP-β-CD] in a molar ratio of 1:2

From the Table IV the reaction conditions in complexing racemic DHP or enantiomers thereof with different cyclodextrins are evident. The conditions for preparing the inclusion complex of (−)-NC.HCl with HP-β-CD in a molar ratio of 1:2 were the same as in preparing the corresponding 1:1 complex with a difference that for preparing the title complex 2 moles of HP-β-CD and 1 mole of (−) nicardipine hydrochloride were used.

$^1$H-NMR:

In the specter of the inclusion complex in the D$_2$O solution the following changes in nicardipine moiety were observed:

shifts of signals for methyl groups ortho to dihydropyridine-NH:
  2.2154 ppm 2.231 ppm

EXAMPLE 13

In the Table IV the reaction conditions and ability of preparing inclusion complexes of racemic and optically active DHP with different cyclodextrins are represented schematically.

Otherwise the preparation processes were carried out in such a way as described in the above Examples.

EXAMPLE 14

Water solubility

The comparison of water solubility of optically active and racemic dihydropyridines in a free form or bound into inclusion complexes with β-Cd, Me-β-CD and HP-β-CD The concentration of dissolved active substances at room temperature was established in clear filtrates of saturated solutions with liquid chromatography according to a method with external standard.

In FIG. 37 and 38 there is illustrated a comparison of water solubilities of unbound nifedipine and of nifedipine bound into complexes with Me-β-CD and HP-β-CD, as well as of unbound amlodipine besylate and amlodipine besylate bound into complexes with β-Cd, Me-β-CD and HP-β-CD.

Analysis of enantiomers and racemates of DHP (free and complexed)

Dynamic scanning calorimetry (DSC):

FIGS. 13 to 28 represent thermograms of inclusion complexes of enantiomers and racemates of nitrendipine and nicardipine hydrochloride with Me-β-CD and HP-β-CD, resp., as well as of the free active substance (enantiomers and racemate).

$^1$H-NMR:

FIGS. 29 to 36 represent NMR spectra of inclusion complexes of enantiomers and racemates of nitrendipine and nicardipine hydrochloride with Me-β-CD and HP-β-CD, resp., as well as of the free active substance (enantiomers and racemate).

EXAMPLE 15

Tablets containing 5 mg of amlodipine (in the form of a base) in an inclusion complex of its besylate salt with methyl-β-cyclodextrin (Me-β-CD)

| Ingredients | mg/tablet | % |
|---|---|---|
| inclusion complex of amlodipine besylate with Me-β-CD (content 30% of amlodipinee - as a base - in the complex) | 16.7 | 8.4 |
| lactose | 100.1 | 50.0 |
| microcrystalline cellulose (Vitacel A 300) | 66.8 | 33.4 |
| maize starch | 13.2 | 6.6 |
| colloidal silicon dioxide (Aerosil ® 200) | 1.0 | 0.5 |
| talcum | 1.0 | 0.5 |
| magnesium stearate | 1.2 | 0.6 |
| | 200.0 | |

Process for preparing 500,000 tablets

Inclusion complex of amlodipine besylate with methyl-β-cyclodextrin (8.35 kg) (content 30% of amlodipine—as a base—in the complex), lactose (50.05 kg), microcrystalline cellulose (33.40 kg) and maize starch (6.60 kg) were sieved through an oscillation sieve with the mesh size of 0.8 mm into a granulator and the mixture was stirred. Then colloidal silicon dioxide (0.50 kg), talcum (0.50 kg) and magnesium stearate (0.60 kg), all sieved through the oscillation sieve with the mesh size of 0.5 mm, were added to the mixture and stirred into a homogenous composition. The granulate was processed into tablets on a rotation tableting machine and tablets having a weight of 200.0 mg each were obtained.

EXAMPLE 16

Tablets containing 10 mg of amlodipine (in the form of a base) in an inclusion complex of its besylate salt with methyl-β-cyclodextrin (Me-β-CD)

| Ingredients | mg/tablet | % |
|---|---|---|
| inclusion complex of amlodipine besylate with Me-β-CD (content 30% of amlodipinee - as a base - in the complex) | 33.4 | 8.4 |
| lactose | 200.2 | 50.0 |
| microcrystalline cellulose | 133.6 | 33.4 |
| maize starch | 26.4 | 6.6 |
| colloidal silicon dioxide (Aerosil ® 200) | 2.0 | 0.5 |
| talcum | 2.0 | 0.5 |
| magnesium stearate | 2.4 | 0.6 |
| | 400.0 | |

It is proceeded as in Example 15 except for the amounts of ingredients which are stated in the composition.

EXAMPLE 17

Tablets with a sustained release of an active substance, containing (+) nicardipine hydrochloride (30 mg) in an inclusion complex with β-cyclodextrin (β-CD)

| Ingredients | mg/tablet | % |
|---|---|---|
| inclusion complex of (+) nicardipine hydrochloride with β-cyclodextrin (β-CD) (content 25% of active substance in a complex) | 120.0 | 32.2 |
| sodium alginate | 150.0 | 40.3 |
| microcrystalline cellulose (Avicel PH 101) | 69.3 | 18.6 |
| polyvinyl pyrrolidone | 24.0 | 6.5 |
| stearic acid | 7.6 | 2.0 |
| magnesium stearate | 1.6 | 0.4 |
| | 372.5 | |

Process for preparing 200,000 tablets

Inclusion complex of (+) nicardipine hydrochloride with β-cyclodextrin (24.00 kg), sodium alginate (30.00 kg) and microcrystalline cellulose (13.86 kg) was sieved through an oscillation sieve with the mesh size of 0.8 mm into a granulator and the mixture was stirred. The mixture was granulated with a solution of polyvinyl pyrrolidone (4.80 kg) in ethanol (10.00 kg). The moist granulate was dried and the dried granulate was sieved through a sieve with the mesh size of 1.0 mm. Stearic acid (1.52 kg) and magnesium stearate (0.32 kg), all sieved through the oscillation sieve with the mesh size of 1.0 mm, were added to the dry granulate in a granulator and the mixture was stirred into a homogenous composition. The granulate was processed into tablets on a rotation tableting machine and tablets having a weight of 372.5 mg each were obtained.

EXAMPLE 18

Tablets with sustained release of the active substance, containing (+) nicardipine hydrochloride (30 mg) in an inclusion complex with β-cyclodextrin (β-CD)

It was proceeded in the same way as in Example 17 with the difference that glycerol ditripalmito stearate (Precirol ATO 5) (0.745 kg, 1%) was substituted for microcrystalline cellulose (0.745 kg).

EXAMPLE 19

Tablets with sustained release of the active substance, containing (+) nicardipine hydrochloride (30 mg) in an inclusion complex with β-cyclodextrin (β-CD)

It was proceeded in the same way as in Example 17 with the difference that sodium lauryl sulfate (Texapon K 12)(0.372 kg; 0.5 %) was substituted for microcrystalline cellulose (0.372 kg).

EXAMPLE 20

Capsules with sustained release of the active substance, containing (+) nicardipine hydrochloride (30 mg) in an inclusion complex with β-cyclodextrin (β-CD)

| Ingredients | mg/capsule | % |
|---|---|---|
| inclusion complex of (+) nicardipine hydrochloride with β-cyclodextrin (β-CD) (content 25% of active substance in a complex) | 120.0 | 38.1 |
| sodium alginate | 175.0 | 55.5 |
| polyvinyl pyrrolidone | 18.5 | 5.9 |
| magnesium stearate | 1.5 | 0.5 |
| | 315.0 | |

It was proceeded in the same way as in Example 17 with the difference that the granulate obtained was filled in capsules.

EXAMPLE 21

Tablets with sustained release of the active substance, containing (+) nicardipine hydrochloride (30 mg) in an inclusion complex with β-cyclodextrin (β-CD)

| Ingredients | mg/tablet | % |
|---|---|---|
| inclusion complex of (+) nicardipine hydrochloride with β-cyclodextrin (β-CD) (content 25% of active substance in a complex) | 120.0 | 50.0 |
| hydroxypropyl methylcellulose (Methocel E4MP) | 35.0 | 14.6 |
| microcrystalline cellulose | 73.9 | 30.8 |
| glycerol ditripalmito stearate (Precirol ATO5) | 7.5 | 3.1 |
| colloidal silicon dioxide (Aerosil ® 200) | 2.4 | 1.0 |
| magnesium stearate | 1.2 | 0.5 |
| | 240.0 | |

Process for preparing 300,000 tablets

Inclusion complex of (+) nicardipine hydrochloride with β-cyclodextrin (36.00 kg), hydroxypropyl methylcellulose (10.50 kg) and microcrystalline cellulose (22.17 kg) was sieved through an oscillation sieve with the mesh size of 0.8 mm into a granulator and the mixture was stirred. Glycerol ditripalmito stearate (2.25 kg), colloidal silicon dioxide (0.72 kg) and magnesium stearate (0.36 kg), all sieved through an oscillation sieve with the mesh size of 0.5 mm, were added to the mixture and stirred into a homogenous composition. The granulate was processed into tablets on a rotation tableting machine and tablets having a weight of 240.0 mg each were obtained.

EXAMPLE 22

Capsules with sustained release of the active substance, containing (+) nicardipine hydrochloride (30 mg) in an inclusion complex with β-cyclodextrin (β-CD)

| Ingredients | mg/capsule | % |
|---|---|---|
| inclusion complex of (+) nicardipine hydrochloride with β-cyclodextrin (β-CD) (content 25% of active substance in a complex) | 120.0 | 72.3 |
| hydroxypropyl methylcellulose (Methocel E4MP) | 40.0 | 24.1 |
| glyceral ditripalmito stearate (Precirol ATO5) | 5.0 | 3.0 |
| magnesium stearate | 1.0 | 0.6 |
| | 166.0 | |

It was proceeded in the same way as in Example 21 with the difference that the granulate obtained was filled in capsules.

EXAMPLE 23

Tablets with sustained release of the active substance, containing (+) nicardipine hydrochloride (30 mg) in an inclusion complex with β-cyclodextrin (β-CD)

| Ingredients | mg/tablet | % |
|---|---|---|
| inclusion complex of (+) nicardipine hydrochloride with β-cyclodextrin (β-CD) (content 30% of active substance in a complex) | 100.00 | 52.6 |
| hydroxypropyl methylcellulose (Methocel E4MP) | 30.0 | 15.8 |
| hydroxypropyl cellulose | 15.0 | 7.9 |
| microcrystalline cellulose (Avicel pH 102) | 38.4 | 20.2 |
| glyceral ditripalmito stearate (Precirol ATO5) | 1.9 | 1.0 |
| colloidal silicon dioxide (Aerosil® 200) | 1.5 | 0.8 |
| stearic acid | 1.0 | 0.5 |
| talcum | 2.2 | 1.2 |
| | 190.0 | |

It was proceeded in the same way as in Example 21.

TABLE I

Water solubility of racemic and optically active dihydropyridines in free form or bound in inclusion complexes (in mg/ml)

| dihydropyridine | uncomplex. | complex. Me-β-CD | complex. HP-β-CD | complex. β-CD | complex. HE-β-CD |
|---|---|---|---|---|---|
| nifedipine | 0.01 | 0.20 | 0.13 | | |
| amlodipine besylate | 1.1 | 25.0 | 17.0 | 10.0 | 4.5 |
| felodipine | $0.8 \cdot 10^{-3}$ | $3.1 \cdot 10^{-3}$ | $1.0 \cdot 10^{-3}$ | | $1.0 \cdot 10^{-3}$ |
| (±)nicardipine.HCl | 1.5 | 145.8 | 97.9 | 54.8 | 53.8 |
| (−)nicardipine.HCl | 0.1 | 127.4 | 68.0 | 15.6 | 54.2 |
| (+)nicardipine.HCl | 0.4 | 133.1 | 59.9 | 15.8 | 52.7 |
| (±)nitrendipine | $0.6 \cdot 10^{-3}$ | $1.3 \cdot 10^{-3}$ | | | |
| (−)nitrendipine | $0.3 \cdot 10^{-3}$ | $1.3 \cdot 10^{-3}$ | | | |
| (+)nitrendipine | $0.75 \cdot 10^{-3}$ | $1.3 \cdot 10^{-3}$ | | | |
| (−)nicardipine.HCl* | | | 130.0* | | |

*molar ratio of the complex (−)-NC.HCl:HP-β-CD amounts to 1:2
β-CD = β-cyclodextrin
Me-β-CD = methyl-β-cyclodextrin
HP-β-CD = 2-hydroxypropyl-β-cyclodextrin
HE-β-CD = 2-hydroxyethyl-β-cyclodextrin

TABLE II

Analytical parameters characterizing the structure of enantiomeric and racemic complexes of nicardipine-hydrochloride (NC.HCl) with HP-β-CD as well as of the active substance (enantiomers and racemate)

| | $[\alpha]^{22}_{D(H_2O, 0.5)}$ | DSC/m.p. | NMR shifts $CH_3(O-NH)/ppm/$ | Rtg lattice spacings | (Intensity) | d/Å/ (I) |
|---|---|---|---|---|---|---|
| NC.HCl racemate | 0 | 160–175 | 2.362; 2.338 | 3.9580 (3072); | 4.3877 (2112); | 6.3931 (1422) |
| NC.HCl racemate HP-β-CD | +96.9° | / | 2.354; 2.323; 2.292 | 4.7183 (1362); | 4.8394 (1354); | 4.7601 (1344) |
| (+)NC.HCl | +72.0° | 160–178 | 2.362; 2.338 | 3.8771 (3950); | 6.6575 (1372); | 5.3353 (1324) |
| (+)NC.HCl—HP-β-CD | +105.3° | / | 2.385; 2.323 | 4.7353 (1256); | 4.8054 (1216); | 4.4681 (1214) |
| (−)NC.HCl | −71.5° | 158–172 | 2.362; 2.338 | 3.8828 (3642); | 5.3442 (1390); | 6.6705 (1292) |
| (−)NC.HCl HP-β-CD | +96.2° | / | 2.366; 2.342 | 4.6879 (1408); | 4.6395 (1378); | 4.8851 (1342) |
| HP-β-CD | +127.0° | / | | broad amorphous peaks: 7–5 and 4.5–3.8 Å | | |
| Instrument | Perkin Elmer -MC 341 | Perkin Elmer DSC-4 | Varian YXR 300 | X ray powder difractometer: Phillips PW 1710; | | |

TABLE II-continued

Analytical parameters characterizing the structure of enantiomeric and racemic complexes
of nicardipine-hydrochloride (NC.HCl) with HP-β-CD as well as of the active substance (enantiomers and racemate)

| | /α/²² D(H2O, 0.5) | DSC/m.p. | NMR shifts CH₃(O—NH)/ppm/ | Rtg lattice spacings | (Intensity) | d/Å/ (I) |
|---|---|---|---|---|---|---|
| | | | | =1.5418 Å (CuK$_\alpha$) Al carrier for filling samples | | |

TABLE III

Analytical parameters characterizing the structure of enantiomeric and racemic complexes of
nitrendipine (NTP) with Me-β-CD as well as of the active substance (enantiomers and racemate)

| | /α/²²$_{D, MeOH, 0.5}$ | DSC/m.p./°C./ | NMR shifts CH/ppm/ | Rtg lattice spacings (intensity) | | |
|---|---|---|---|---|---|---|
| NTP racemate | 0 | 175–165 | 6.55 | 8.8372 (21418); | 3.6629 (6156); | 3.7508 (5002) |
| NTP racemate Me-β-CD | +119.5° | / | 6.70 | 4.8851 (1742); | 4.7758 (1710); | 4.8325 (1706) |
| (–)NTP | –20.1° | 155–160 | 6.55 | 9.5414 (8242); | 3.9679 (7610); | 6.4939 (2690) |
| (–)NTP-Me-β-CD | +116.0° | / | 6.42 | 4.6958 (1608); | 4.9858 (1562); | 4.4102 (1488) |
| (+)NTP | +20.6° | 150–158 | 6.55 | 9.5782 (5624); | 65088 (2618); | 3.7116 (2442) |
| (+)NTP Me-β CD | +122.7° | / | 6.38 | 4.6118 (1682); | 5.0420 (1588); | 4.9534 (1586) |
| Me-β-CD | +150.9° | / | | broad amorphous signals between 8.5–7.0 and 5.2–4.4 | | |

TABLE IV

Review of reaction conditions and ability for preparing inclusion complexes of racemic and optically active DHP
with different cyclodextrins

| DHP | Enant. racemate | β-CD | ME-β-CD | HP-β-CD | HE-β-CD | solvent | Konc.DHP,CD (mol/l) | t/h/ | T/°C./ | elimination of solvent |
|---|---|---|---|---|---|---|---|---|---|---|
| MNA | (+), (–), R | / | + | + | + | CH₃OH | 0,05 | 1 | reflux (65° C.) | evaporation |
| NC.HCl | (+), (–), R | + | + | + | + | H₂O | 0,02–0,05 | 0.5–2 | 70° C. | lyophilisation |
| NTP | (+), (–), R | / | + | + | + | CH₃OH | 0,05 | 0.1 | room temp. | evaporation |
| AML.S. | (+), (–), R | + | + | + | + | H₂O | 0,02–0,08 | 1–2 | 70° C. | lyophilisation |
| AML.A | (+), (–), R | / | + | + | + | CH₃OH | 0,05 | 1 | refl. (65° C.) | evaporation |
| KMNA | (+), (–), R | / | + | + | + | CH₃OH | 0,05 | 1 | refl. (65° C.) | evaporation |
| FDP | (+), (–), R | / | + | + | + | CH₃OH | 0,02–0,07 | 1–2 | refl. (65° C.) | evaporation |

MNA = 2-(N-benzyl-N-methyl-amino)ethyl-2,6-dimethyl-4-(3-nitrophenyl)-1,4-dihydropirydine-3,5-carboxylic acid
NH.HCl = nicardipine hydrochloride
NTP = nitrendipine
AML.S = amlodipine besylate
AML.A = ethyl-2-[2-aminoethoxy)methyl]-4-(2-chlorophenyl)-1,4-dihydro-6-methyl-3,5-pyridine-carboxylic acid
KMNA = ethyl-1,4-dihydro-2,6-dimethyl-4-(2,3-dichlorophenyl)-3,5-pyridine-carboxylic acid
FDP = felodipine

We claim:

1. Inclusion complex of (+) enantiomer of nicardipine or (–) enantiomer of nicardipine or acid addition salt thereof with a member selected from the group consisting of methyl-β-cyclodextrin of the molecular weight of about 1311, 2-hydroxyethyl-β-cyclodextrin and 2-hydroxypropyl-β-cyclodextrin, said complexes having a water solubility between about 0.2 mg/ml and about 150.0 mg/ml at 25° C., the molar ratio of (+) or (–) enantiomer of nicardipine or acid addition salt thereof to said member in the inclusion complex being about 1:1.

2. The inclusion complex of claim 1 being of an enantiomer of (+) or (–) nicardipine hydrochloride.

3. The inclusion complex of claim 1 wherein said member is methyl-β-cyclodextrin.

4. The inclusion complex of claim 1 wherein said member is 2-hydroxyethyl-β-cyclodextrin.

5. The inclusion complex of claim 1 wherein said member is 2-hydroxypropyl-β-cyclodextrin.

6. A method for treating a patient in need of a coronary-vasodilatory or cerebral-vasodilatory agent, which comprises administering to said patient an effective amount of an inclusion complex of claim 1 as the coronary-vasodilatory or cerebral-vasodilatory agent.

7. A method for treating a patient in need of a coronary-vasodilatory or cerebral-vasodilatory agent, which comprises administering to said patient an effective amount of an inclusion complex of claim 2 as the coronary-vasodilatory or cerebral-vasodilatory agent.

8. A method for treating a patient in need of a coronary-vasodilatory or cerebral-vasodilatory agent, which comprises administering to said patient an effective amount of an inclusion complex of claim 3 as the coronary-vasodilatory or cerebral-vasodilatory agent.

9. A method for treating a patient in need of a coronary-vasodilatory or cerebral-vasodilatory agent, which comprises administering to said patient an effective amount of an inclusion complex of claim 4 as the coronary-vasodilatory or cerebral-vasodilatory agent.

10. A method for treating a patient in need of a coronary-vasodilatory or cerebral-vasodilatory agent, which comprises administering to said patient an effective amount of an inclusion complex of claim 5 as the coronary-vasodilatory or cerebral-vasodilatory agent.

\* \* \* \* \*